US011633102B2

(12) United States Patent
Joudi

(10) Patent No.: US 11,633,102 B2
(45) Date of Patent: Apr. 25, 2023

(54) APPARATUS AND METHOD FOR PROVIDING IMPROVED HEALTH CARE

(71) Applicant: Luminent Health, LLC, Boston, MA (US)

(72) Inventor: Tony Joudi, Boston, MA (US)

(73) Assignee: Luminent Health, LLC, Boston, MA (US)

( * ) Notice: Subject to any disclaimer, the term of this patent is extended or adjusted under 35 U.S.C. 154(b) by 308 days.

(21) Appl. No.: 16/523,305

(22) Filed: Jul. 26, 2019

(65) Prior Publication Data

US 2020/0029837 A1 Jan. 30, 2020

Related U.S. Application Data

(60) Provisional application No. 62/703,662, filed on Jul. 26, 2018.

(51) Int. Cl.
*G16H 40/67* (2018.01)
*A61B 5/00* (2006.01)
(Continued)

(52) U.S. Cl.
CPC .............. *A61B 5/0022* (2013.01); *A61B 1/04* (2013.01); *A61B 1/06* (2013.01); *A61B 1/07* (2013.01); *A61B 1/227* (2013.01); *A61B 5/0006* (2013.01); *A61B 5/0008* (2013.01); *A61B 5/01* (2013.01); *A61B 5/02055* (2013.01); *A61B 5/14552* (2013.01); *A61B 5/25* (2021.01); *A61B 5/6898* (2013.01); *A61B 7/04* (2013.01);
(Continued)

(58) Field of Classification Search
CPC ..... A61B 5/02055; A61B 5/25; A61B 5/0008; A61B 5/01; A61B 5/14552; A61B 5/6898; A61B 5/02233; A61B 1/04; A61B 1/07; A61B 1/227; A61B 7/04; A61B 8/4472; G16H 40/67; G16H 50/20
See application file for complete search history.

(56) References Cited

U.S. PATENT DOCUMENTS

D664,258 S 7/2012 Harkin et al.
D745,167 S 12/2015 Canas et al.
(Continued)

FOREIGN PATENT DOCUMENTS

WO WO 2014/105649 7/2014

OTHER PUBLICATIONS

Facebook Post to Boston University School of Medicine Class of 2020, 2019.
(Continued)

*Primary Examiner* — Ankit D Tejani
*Assistant Examiner* — Joshua Brendon Solomon
(74) *Attorney, Agent, or Firm* — Pandiscio & Pandiscio

(57) ABSTRACT

A system for acquiring physiological data from a patient, the system comprising: a smartphone configured for wireless communication; an adapter for releasably mounting to the smartphone; a sensor module for releasably mounting to the adapter, the sensor module comprising at least one sensor for acquiring physiological data from the patient; and a software app running on the smartphone for (i) wirelessly controlling operation of the sensor module and wirelessly receiving the physiological data from the sensor module, and (ii) wirelessly communicating with a remote location.

13 Claims, 53 Drawing Sheets

(51) Int. Cl.

| | |
|---|---|
| *A61B 5/0205* | (2006.01) |
| *A61B 5/01* | (2006.01) |
| *A61B 7/04* | (2006.01) |
| *A61B 8/00* | (2006.01) |
| *A61B 5/1455* | (2006.01) |
| *A61B 1/227* | (2006.01) |
| *A61B 1/04* | (2006.01) |
| *A61B 1/07* | (2006.01) |
| *G16H 50/20* | (2018.01) |
| *A61B 5/25* | (2021.01) |
| *A61B 1/06* | (2006.01) |
| *A61B 5/022* | (2006.01) |

(52) U.S. Cl.
CPC .......... *A61B 8/4472* (2013.01); *G16H 40/67* (2018.01); *G16H 50/20* (2018.01); *A61B 5/02233* (2013.01)

(56) References Cited

U.S. PATENT DOCUMENTS

| | | | |
|---|---|---|---|
| D767,485 S | 9/2016 | To et al. | |
| D784,541 S | 4/2017 | Hilbig et al. | |
| D796,363 S | 9/2017 | Ross et al. | |
| D874,007 S | 1/2020 | Chang et al. | |
| D883,488 S | 5/2020 | Moss et al. | |
| D902,413 S | 11/2020 | Laurino et al. | |
| D914,896 S | 3/2021 | Hoshino et al. | |
| D917,704 S | 4/2021 | Al-Ali et al. | |
| D919,100 S | 5/2021 | Al-Ali et al. | |
| D919,819 S | 5/2021 | Nair et al. | |
| D921,204 S | 6/2021 | Golda et al. | |
| D928,329 S | 8/2021 | Huang et al. | |
| 2008/0146277 A1 | 6/2008 | Anglin et al. | |
| 2013/0300919 A1* | 11/2013 | Fletcher | H04N 5/2254 348/360 |
| 2014/0066798 A1* | 3/2014 | Albert | A61B 5/6823 600/513 |
| 2015/0065803 A1* | 3/2015 | Douglas | A61B 1/00045 600/200 |
| 2015/0073285 A1* | 3/2015 | Albert | H04B 5/0043 600/509 |
| 2017/0014079 A1* | 1/2017 | Lee | A61B 7/02 |
| 2017/0105700 A1 | 4/2017 | Bar-zion et al. | |
| 2017/0280996 A1 | 10/2017 | Myung et al. | |
| 2018/0014743 A1 | 1/2018 | Fecteau et al. | |
| 2018/0168440 A1* | 6/2018 | Das | G06T 7/50 |
| 2020/0253474 A1 | 8/2020 | Muhsin et al. | |
| 2020/0315583 A1* | 10/2020 | Baumann | A61B 5/0053 |

OTHER PUBLICATIONS

Https://www.tigermedical.com/Products/iPhone-Otoscope---Clinicians-Oto_BIO1455.aspx, Cellscopr 1455 iphone Otoscope—Clinician's Oto *Discontinued*, 2014, Tiger Medical, Inc.

https://www.getilluminate.com/ the-illuminate, "The Illuminate", 2021, Illuminate.

https://www.getilluminate.com/otoscope, "The Otoscope", 2021, Illuminate.

www.my-homedoc.com, "Primary care exams in the palm of your hand", 2018, MyHomeDoc.

Zakrzewski et al., Real-Time Blood Pressure Estimation From Force-Measured Ultrasound,IEEE Transactions on Biomedical Engineering, vol. 65, No. 11, Nov. 2018.

* cited by examiner

| Color | Dark Blue | Magenta | Cyan | Orange |
|-------|-----------|---------|-------|--------|
| Hex   | 010063    | 9f0ff0  | 28c0f0 | F29a2f |

FIG. 2

| SELECTED SYMPTOM | SENSOR(S) TRIGGERED | FOLLOW UP PERIOD | RATIONALE |
|---|---|---|---|
| SORE THROAT | Throat imaging<br>Nasal imaging<br>Thermometer | 12 hours<br>12 hours<br>4 hours | Imaging reveals potential inflammation, swelling, and color of oropharynx. |
| FEVER | Thermometer<br>Ear imaging<br>Nose imaging<br>Throat imaging<br>Blood pressure | 4 hours<br>12 hours<br>12 hours<br>12 hours<br>4 hours | Assessment of temperature to monitor trends until other symptoms present. |
| HEADACHE | Blood Pressure<br>Temperature<br>Pulse oximeter | 4 hours<br>4 hours<br>4 hours | If only headache, assess blood pressure and temperature. Monitor to see if worsening. |
| COUGH | Stethoscope<br>Temperature | 6 hours<br>6 hours | Normally URI, but follow up period assesses potential other sources of infectious disease |
| RUNNY NOSE/CONGESTION | Throat imaging<br>Nasal imaging | 12 hours<br>12 hours | Evaluation of sinus congestion over time and progression graphically |
| RACING HEART/TACHYCARDIA | ECG<br>Pulse oximeter<br>Blood Pressure | -<br>-<br>- | Evaluation if single symptom – assess for arrhythmia, otherwise assess as symptom of infectious disease |
| DIZZINESS | Blood Pressure<br>Pulse oximeter | 2 hours<br>2 hours | Evaluate if single symptom – low blood pressure, otherwise assess as symptom of infectious disease |
| FATIGUE/TIREDNESS | Blood Pressure<br>Pulse oximeter<br>ECG | 24 hours<br>24 hours<br>24 hours | Assessment of fatigue over time allows useful prognostic forecast of recovery |
| LOSS OF APPETITE | - | - | Evaluate in context of symptoms concordant with GI infection |
| SWEATING AT NIGHT | - | - | Evaluate in context of infectious disease |
| BODY ACHES/MUSCLE ACHES | Thermometer | 4 hours | Assessment of malaise over time allows useful prognostic forecast of recovery |
| ABDOMINAL PAIN | Stethoscope<br>Blood Pressure<br>Temperature | 2 hours<br>2 hours<br>2 hours | Assessment takes into account potentially serious GI issues, otherwise evaluate as ID |

* For any symptoms that trigger a test that has a higher frequency of testing in the follow up period, the higher frequency one takes priority over the lower one. Symptoms that have overlapping tests should only perform that test once in a cycle of testing. For symptoms listed in bold, perform the tests at the follow up period frequency ONLY if the symptom chosen is the ONLY symptom the patient complains about.

FIG. 15

| Test | Sensor Activated | Result |
| --- | --- | --- |
| Lung Sounds | Stethoscope | Audio file and filtered waveform |
| Heart Sounds | Stethoscope | Audio file and filtered waveform |
| Blood Pressure | Blood pressure cuff | mmHg |
| Ear Imaging | iPhone X Camera | Macro lens image |
| Nose Imaging | iPhone X Camera | Macro lens image |
| Throat Imaging | iPhone X Camera | Macro lens image |
| Temperature | Thermometer | Degrees C or F |
| Heart Rhythm | ECG | Filtered ECG waveform |
| Oxygen Saturation | Pulse oximeter | Pulse rate and oxygen saturation |

FIG. 26

| Head and Neck | Common Name | notes |
| --- | --- | --- |
| Pharyngitis | Sore Throat | - |
| Flu | - | - |
| Cold | - | - |
| Otitis media | Ear Infection | - |
| Conjunctivitis | Pink Eye | - |
| Dermatitis | Rash | - |
| Bronchitis | - | - |
| Sinusitis | - | - |
| Cellulitis | - | - |
| Arrhythmia | Skipped Beat or Flutter | - |
| FUO | Fever of Unknown Origin | - |
| Insect Bites | - | - |
| Asthma | - | - |
| Myocardial Infarct | Heart Attack | As a rule-out in emergency situations only |

FIG. 44

| Condition | Common Name | notes |
|---|---|---|
| Hypertension | High Blood Pressure | - |
| Atrial Fibrillation | A-fib, arrhythmia | - |

FIG. 45

| SHOWN TO PATIENT | SHOWN TO PROVIDER IN "OF NOTE" | NOTES |
|---|---|---|
| HAVE YOU LOST ANY WEIGHT? | Unexplained weight loss | |
| HAVE YOU HAD ANY NIGHT SWEATS? | Night sweats | |
| ARE YOU FATIGUED? | Fatigue | |
| ANY CHANGES IN SLEEPING PATTERNS? | Somnipathy | |
| ANY CHANGE IN APPETITE? | Appetite changes | |
| ANY UNEXPLAINED FEVERS? | FUO | |
| ANY LUMPS OR BUMPS? | New lump/bump | |
| ANY RECENT FALLS? | Unexplained fall | |
| ANY ITCHES OR RASHES? | Pruritis/Dermatitis | |
| ANY VISUAL CHANGES? | Visual field changes | |
| ANY HEADACHES? | Recurrent headaches | |
| HOW ABOUT EYE PAIN? | Eye pain | |
| DOUBLE VISION? | Diplopia | |
| BLIND SPOTS? | Scotoma | |
| ANY SUDDEN VISUAL FLOATERS/SPARKLES? | Retinal hemorrhage | Notify patient to get immediate emergency treatment. |
| FEELING LIKE A CURTAIN GOT PULLED DOWN OVER EYES? | Amaurosis fugax | |
| ANY TOOTH ACHES? | Tooth pain | |
| RINGING IN EARS? | Tinnitus | |
| PAINFUL SWALLOWING? | Odynophagia | |
| ANY CHEST PAIN? | Chest pain | Notify patient to get immediate emergency treatment. |
| SHORTNESS OF BREATH? | Dyspnea | |
| DOES IT OCCUR AT NIGHT? | Paroxysmal nocturnal dyspnea | |
| EXERCISE INTOLERANCE? | Exercise intolerance | |
| DIFFICULTY BREATHING? | Dyspnea | |
| HEART RACING? | Palpitations | |
| IRREGULAR HEART BEATS? | Palpitations | |
| ANY FAINTNESS OR LOSS OF CONSCIOUSNESS? | Presyncope/Syncope | |
| ANY PAIN/NUMBNESS IN YOUR LEGS? | Claudication | |
| ANY PERSISTENT COUGH? | Persistent cough | |
| IF YES TO THE ABOVE: ANY BLOOD IN SPIT UP? | Hemoptysis | |

FIG. 46 (continued on next page)

| | |
|---|---|
| WHAT ABOUT WHEEZING? | Wheezing |
| ANY ABDOMINAL PAIN? | Abdominal pain |
| INDIGESTION? | Indigestion |
| BLOATING OR CRAMPING? | Bloating |
| LOSS OF APPETITE? | Anorexia |
| NAUSEA OR VOMITING? | Nausea/vomiting |
| IF YES TO ABOVE: ANY BLOOD IN SPIT UP? | Hematemesis |
| ANY BLOOD IN STOOL? | Hematochezia |
| ANY BLACK, TARRY STOOLS? | Melena |
| ANY FEELING THAT YOU CAN'T EMPTY YOUR BOWELS? | Tenesmus |
| ANY PROBLEMS WITH YOUR BLADDER OR URINATION? IF NO, SKIP – OTHERWISE, CONTINUE | |
| ANY DIFFICULTY PEEING? | Micturition incontinence |
| IF MALE, SKIP - OTHERWISE, CONTINUE | |
| ANY VAGINAL DISCHARGE OR PAIN? | Vaginal pain |
| ANY ISSUES WITH YOUR PERIOD? | Menstrual issues |
| DO YOU FEEL LIKE YOU USE A LOT OF TAMPONS OR LINERS? | Heavy menses |
| DID YOU HAVE A PAP SMEAR WITHIN THE LAST YEAR? | Pap Smear Up to Date |
| ANY ISSUES WITH CONCEPTION? | Conception and fertilization Issues |

FIG. 46 (continued from preceding page)

APPARATUS AND METHOD FOR PROVIDING IMPROVED HEALTH CARE

REFERENCE TO PENDING PRIOR PATENT APPLICATION

This patent application claims benefit of prior U.S. Provisional Patent Application Ser. No. 62/703,662, filed Jul. 26, 2018 by Luminent Health LLC and Tony Joudi for APPARATUS AND METHOD FOR PROVIDING IMPROVED HEALTH CARE, which patent application is hereby incorporated herein by reference.

FIELD OF THE INVENTION

This invention relates to methods and apparatus for measuring physiological characteristics in general, and more particularly to methods and apparatus for measuring physiological characteristics using a handheld device, and communicating measured data with other parties using the handheld device.

BACKGROUND OF THE INVENTION

With the development and spread of the Internet, it is now possible for healthcare providers who are physically remote from their patients to use technology to make a remote diagnosis of a patient without physically contacting the patient. In practice, a healthcare provider typically speaks to a patient by telephone, obtains information verbally about the patient's condition, and views images or video concerning the patient's condition sent to the healthcare provider wirelessly (e.g., via the Internet). Such "remote diagnoses" traditionally rely on a combination of voice (i.e., telephone) and video/images (e.g., streamed video images of the patient, a photograph taken by the patient of a suspected malady, etc.). In some cases, a diagnosis is made by the healthcare provider after engaging the patient in a video-based conference call (e.g., via Facetime, Skype, etc.).

However, traditional voice and/or video approaches for making a diagnosis remotely suffer from a lack of data concerning the patient's physiological characteristics. By way of example but not limitation, a remote patient may report feeling hot or cold, however, a remote healthcare provider lacks a way to verify that the patient's temperature actually departs from a normal temperature. Similarly, and by way of further example but not limitation, a remote patient may report sinus pain or an earache, however, a healthcare provider generally cannot see inside the remote patient's ear without an otoscope (or similar device) and cameras typically used for videoconferencing lack the optics for looking inside the remote patient's ear.

While it may be possible for a patient to be provided with thermometers, otoscopes, stethoscopes, etc., and for the patient to report the data obtained by the thermometers, otoscopes, stethoscopes, etc., a healthcare provider may not wish to rely on patient-read data, since this has the potential to introduce error (e.g., if the patient misreads a thermometer, incorrectly reports data, etc.). Furthermore, certain data (e.g., the sound of a beating human heart as reported by a stethoscope) requires training and experience to interpret, and such training and experience is unlikely to be possessed by a remote.

Thus there is a need for a new and improved method and apparatus for remotely measuring/inspecting physiological characteristics, wherein the apparatus comprises at least one sensor that is configured to collect data and wirelessly transmit that data to a remote healthcare provider so as to assist the healthcare provider in making a remote diagnosis. There is also a need for new and improved software for prompting the user to report their symptoms in a systematic fashion so that appropriate physiological data can be obtained for making a diagnosis, and for prompting the patient to use one or more sensors to collect the desired physiological data (and for providing instructions and/or prompts for doing so), and for storing, analyzing, and facilitating the transfer of data to the healthcare provider.

SUMMARY OF THE INVENTION

The present invention comprises the provision and use of a new and improved method and apparatus for remotely measuring/inspecting physiological characteristics, wherein the apparatus comprises at least one sensor that is configured to collect data and wirelessly transmit that data to a remote healthcare provider so as to assist the healthcare provider in making a remote diagnosis. The present invention also comprises new and improved software for prompting the user to report their symptoms in a systematic fashion so that appropriate physiological data can be obtained for making a diagnosis, and for prompting the patient to use one or more sensors to collect the desired physiological data (and for providing instructions and/or prompts for doing so), and for storing, analyzing, and facilitating the transfer of data to the healthcare provider.

In accordance with the present invention, and as will hereinafter be discussed in further detail, there is provided a novel device, which is sometimes hereinafter referred to as the Illuminate™ device, which comprises a plurality of modules which are physically mounted to a smartphone and which wirelessly communicate with the smartphone. The smartphone runs a smartphone app which controls operation of the smartphone, and which controls the plurality of modules connected to the smartphone, so as to provide the functionality of the Illuminate™ device as described herein. In this way, the modules can acquire data from the patient, and the smartphone can transmit that data to a remote healthcare provider or healthcare database. Data processing can be conducted at the modules, and/or at the smartphone, and/or at a remote healthcare site. The smartphone also provides teleconferencing capability with a remote healthcare provider using the smartphone's onboard cellular telephone unit, camera, speaker, etc.

Thus, the complete Illuminate™ device essentially comprises the plurality of modules for gathering patient data, and the smartphone for transmitting that patient data to a healthcare provider and for enabling teleconferencing with the healthcare provider, with the various components all working in combination with one another through the Illuminate™ smartphone app which is running on the smartphone.

In one preferred form of the invention, the plurality of modules of the Illuminate™ device preferably comprise:

(i) a sensor module equipped with an IR thermometer, a single lead ECG, a stethoscope, and a pulse oximeter unit;

(ii) an otoscope module equipped with a 3D printed macro lens holder (containing appropriate optics) for providing otoscope functionality to the camera of the smartphone; and (iii) a Bluetooth™ blood pressure cuff.

The plurality of modules of the Illuminate™ device are intended to work with various components and features of smartphone. It will be appreciated that the smartphone typically comprises a CPU, memory containing the software app, a display screen, a speaker/microphone, a cellular telephone unit/WiFi unit, a camera and flashlight unit, a Bluetooth unit and a charger.

In one preferred form of the invention, there is provided a system for acquiring physiological data from a patient, the system comprising:

a smartphone configured for wireless communication;
an adapter for releasably mounting to the smartphone;
a sensor module for releasably mounting to the adapter, the sensor module comprising at least one sensor for acquiring physiological data from the patient; and
a software app running on the smartphone for (i) wirelessly controlling operation of the sensor module and wirelessly receiving the physiological data from the sensor module, and (ii) wirelessly communicating with a remote location.

In another preferred form of the invention, there is provided a system for acquiring physiological data from a patient, the system comprising:

an adapter for releasably mounting to a smartphone;
a sensor module for releasably mounting to the adapter, the sensor module comprising at least one sensor for acquiring physiological data from the patient; and
a software app running on a smartphone for (i) wirelessly controlling operation of the sensor module and wirelessly receiving the physiological data from the sensor module, and (ii) wirelessly communicating with a remote location.

In another preferred form of the invention, there is provided a system for acquiring physiological data from a patient, the system comprising:

a smartphone comprising a light source and a camera; and
an otoscope module for releasably mounting to the smartphone, the otoscope module comprising optics for use in transmitting light from the light source of the smartphone to an anatomical site and for use in capturing an image of the anatomical site with the camera.

In another preferred form of the invention, there is provided a system for acquiring blood pressure data from a patient, the system comprising:

a smartphone;
an ultrasound unit for releasably mounting to the smartphone and for imaging vasculature of the patient;
a pressure transducer unit for measuring the pressure applied by the ultrasound unit against patient; and
a software app running on a smartphone for calculating the blood pressure of the patient based on images acquired by the ultrasound unit and pressure measured by the pressure transducer unit.

In another preferred form of the invention, there is provided a method for acquiring physiological data from a patient, the method comprising:

providing a system comprising:
a smartphone configured for wireless communication;
an adapter for releasably mounting to the smartphone;
a sensor module for releasably mounting to the adapter,
  the sensor module comprising at least one sensor for acquiring physiological data from the patient; and
a software app running on the smartphone for (i) wirelessly controlling operation of the sensor module and wirelessly receiving the physiological data from the sensor module, and (ii) wirelessly communicating with a remote location;
using the software app to control operation of the sensor module so as to acquire physiological data from the patient and transfer the physiological data from the sensor module to the smartphone.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 2 is a schematic view showing a color theme of the Illuminate™ smartphone app;

FIG. 15 is a schematic view showing an exemplary pre-defined list of tests which is generated when a given symptom is selected using the EasyAnalyze™ feature of the Illuminate™ smartphone app;

FIG. 26 is a schematic view showing exemplary single test parameters for the Illuminate™ device;

FIG. 44 is a table showing exemplary acute conditions assessable by the Illuminate™ device;

FIG. 45 is a table showing exemplary chronic conditions assessable by the Illuminate™ device; and FIG. 46 illustrates an exemplary initial intake questionnaire associated with the Illuminate™ device, showing both the "plain English" terms shown to a patient and the corresponding medical terms shown to providers.

DETAILED DESCRIPTION OF THE PREFERRED EMBODIMENTS

Figure 1:
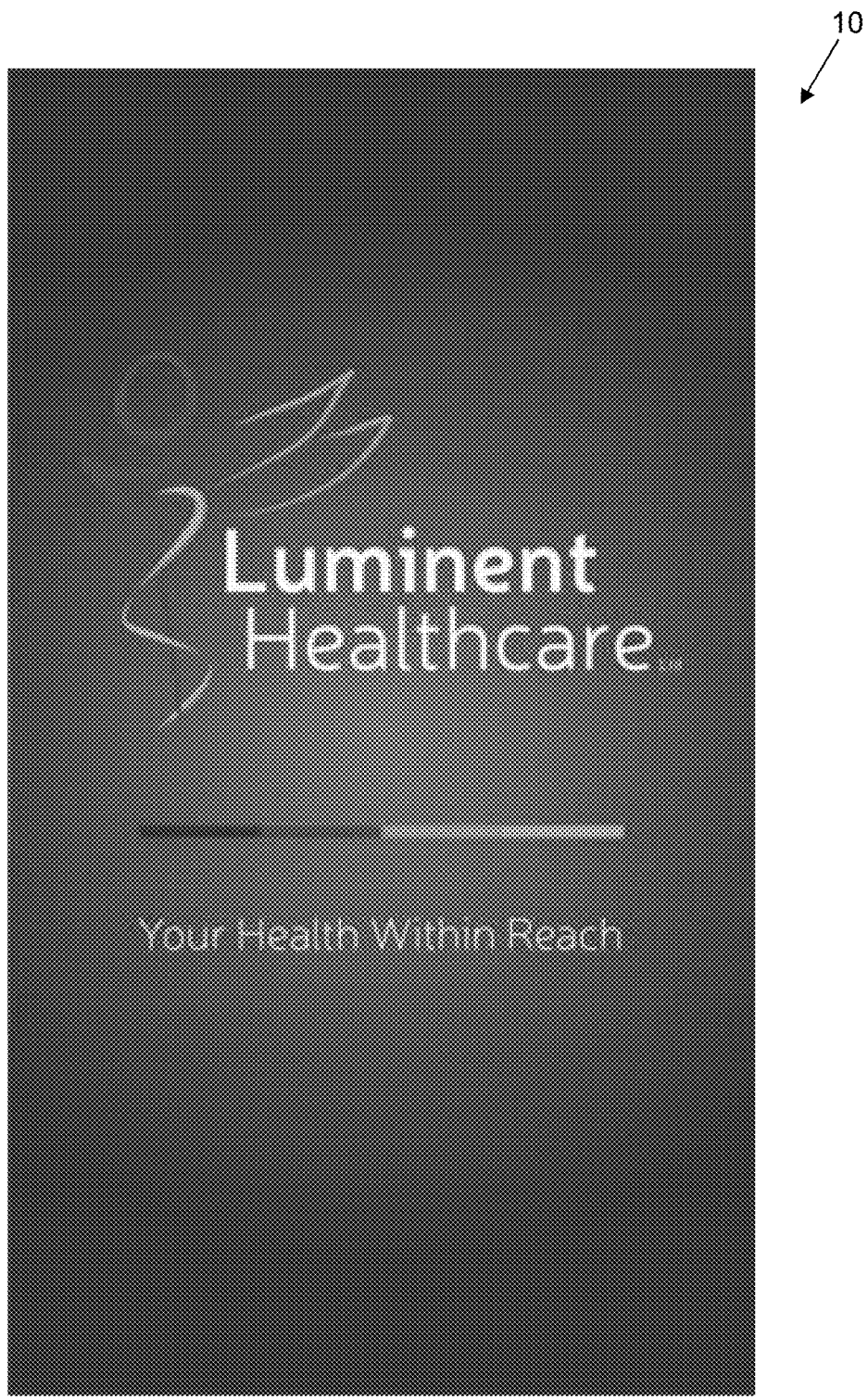
FIG. 1 is a schematic view showing the splash screen of the Illuminate™ smartphone app.

The present invention comprises the provision and use of a new and improved method and apparatus for remotely measuring/inspecting physiological characteristics, wherein the apparatus comprises at least one sensor that is configured to collect data and wirelessly transmit that data to a remote healthcare provider so as to assist the healthcare provider in making a remote diagnosis. The present invention also comprises new and improved software for prompting the user to report their symptoms in a systematic fashion so that appropriate physiological data can be obtained for making a diagnosis, and for prompting the patient to use one or more sensors to collect the desired physiological data (and for providing instructions and/or prompts for doing so), and for storing, analyzing, and facilitating the transfer of data to the healthcare provider.

In accordance with the present invention, and as will hereinafter be discussed in further detail, there is provided a novel device, which is sometimes hereinafter referred to as the Illuminate™ device, which comprises a plurality of modules which are physically mounted to a smartphone and which wirelessly communicate with the smartphone. The smartphone runs a smartphone app which controls operation of the smartphone, and which controls the plurality of modules connected to the smartphone, so as to provide the functionality of the Illuminate™ device as described herein. In this way, the modules can acquire data from the patient, and the smartphone can transmit that data to a remote healthcare provider or healthcare database. Data processing can be conducted at the modules, and/or at the smartphone, and/or at a remote healthcare site. The smartphone also provides teleconferencing capability with a remote healthcare provider using the smartphone's onboard cellular telephone unit, camera, speaker, etc.

Thus, the complete Illuminate™ device essentially comprises the plurality of modules for gathering patient data, and the smartphone for transmitting that patient data to a healthcare provider and for enabling teleconferencing with the healthcare provider, with the various components all working in combination with one another through the Illuminate™ smartphone app which is running on the smartphone.

In one preferred form of the invention, the plurality of modules of the Illuminate™ device preferably comprise:

(i) a sensor module equipped with an IR thermometer, a single lead ECG, a stethoscope, and a pulse oximeter unit;

(ii) an otoscope module equipped with a 3D printed macro lens holder (containing appropriate optics) for providing otoscope functionality to the camera of the smartphone; and (iii) a Bluetooth™ blood pressure cuff.

The plurality of modules of the Illuminate™ device are intended to work with various components and features of smartphone. It will be appreciated that the smartphone typically comprises a CPU, memory containing the software app, a display screen, a speaker/microphone, a cellular telephone unit/WiFi unit, a camera and flashlight unit, a Bluetooth unit and a charger.

1. Introduction

The present invention has three principal goals:
1. expand access to health care;
2. enhance continuity of care and outcomes using an intuitive and easy-to-use medical device; and
3. reduce workload on patients and providers using artificial intelligence (e.g., machine learning).

Figure 3:
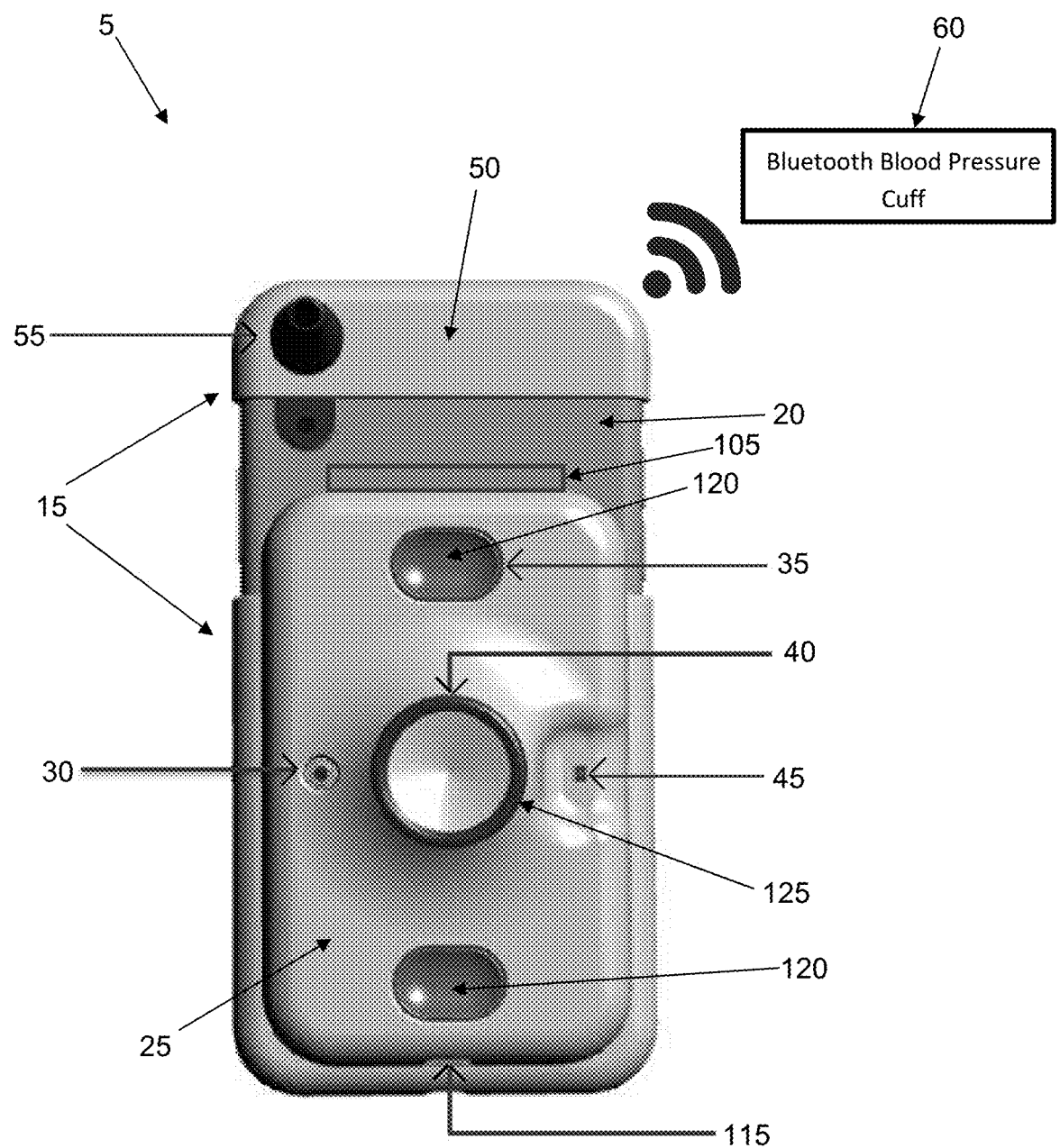
FIGS. 3-5 and 5A-5F are schematic views showing various aspects of the Illuminate™ device.
Figure 4:
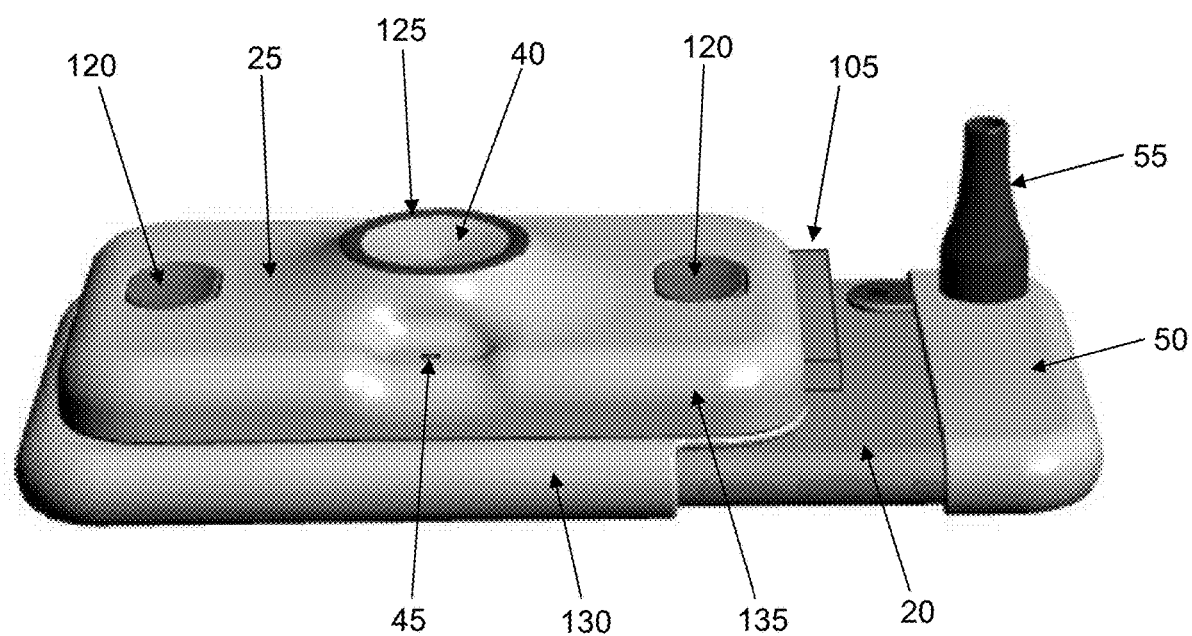

The approach takes telemedicine a step further than a video call and introduces a novel medical device, the Illuminate™ device 5 (see FIG. 3). Designed to be used by both patients and providers as an "electronic doctor's bag," the Illuminate™ device 5 augments office visits by providing an array of digital sensors that allow patient data to be captured in a fast and intuitive fashion. The captured data is then transmitted to a healthcare provider using the Illuminate™ device 5.

Through patients having the Illuminate™ device 5, there are fewer office visits taking up space for patients that need more urgent care. These office visits are replaced by virtual consultations that perform the same basic diagnostic exams that would happen in the physician's office. The Illuminate™ device 5 can also be used as a standalone device to measure diagnostics that chronic care patients need, such as blood pressure, all neatly recorded in the Illuminate™ device 5 for review by a physician upon request, as will hereinafter be discussed in further detail.

For providers, there are reduced costs in terms of the amount of equipment necessary for office spaces. No longer is the same equipment duplicated in multiple offices—instead, a single device (i.e., the Illuminate™ device 5) is provided which is small enough to fit in a pocket of a healthcare provider, and which has the same sensing equipment that can digitally record data, thereby providing for superior record-keeping compared to what is conventionally available.

As patients use the Illuminate™ device 5 and data is accumulated, with their express permission, data analytics are undertaken (using the sensor data captured by the Illuminate™ device 5) to analyze health factors and provide initial assessments of health risks. As more data is provided, these prognostic indicators become more accurate, and can inform healthcare providers and patients proactively of things that can be done to improve patient outcomes.

2. Exemplary Future Uses of the Illuminate™ Device 5

2.1 Physician in-Office

"Dr. Halsey" is a primary care physician that works at her own private family practice. She sees patients of every age. Being in a rural area, she often has patients who complain about the drive. Some patients do not even show up to their scheduled appointments. Wondering about potential solutions to this problem, her practice manager might learn about the Illuminate™ device 5 online. Curious, she might tell Dr. Halsey, who might trial the Illuminate™ device 5 with a few of her patients. Patients using the Illuminate™ device 5 might report greater satisfaction with care as they are able to record data and store it for a later date, without feeling as though they are bothering Dr. Halsey. Patients might also feel as though they are getting better care because, instead of canceling due to the inconvenience of the drive to the office, they can have a full virtual consult from the comfort of their own home. Dr. Halsey might end up recommending the Illuminate™ device 5 to all of her patients, as she finds the increased continuity of care, as well as the convenience of prescribing to pharmacies close to her patients, to be well worth it.

2.2 Physician in the Field

"Dr. Smith" works with Doctors Without Borders. He often finds himself frustrated when he is trying to evaluate patients in the field without essential supplies. When he arrives back in the United States, he might hear about the Illuminate™ device 5 from one of his colleagues using the technology. The high portability of the device, the convenience of it being at the back of his smartphone, and the full complement of sensors, might all appeal to him. When he returns to the field, he might find that he is able to see more patients and give them a more thorough and complete assessment in the field. The long-lasting battery of the Illuminate™ device 5 would enables him to go for several days without having to recharge, and the ease of cleaning with a simple alcohol wipe would keep the Illuminate™ device 5 ready for the next patient with no delay. Physicians in the field might notice Dr. Smith using the Illuminate™ device 5 and ask for more information so they can get one of their own.

2.3 Disaster Relief

The Bahamas is an archipelago of islands located in a "hot spot" for tropical cyclone activity. One year, a particularly strong Category 5 hurricane might tear through the islands, leaving many without power or transportation. The emergency relief teams around the islands, however, might prepare for this disaster by strategically stockpiling Illuminate™ devices 5 at shelters and clinics. Those patients requiring care and consultations would be able to use the battery-charged Illuminate™ devices 5 and interface with physicians remotely. Patients who become injured would be able to use the camera on board the Illuminate™ device 5 to document the wound and get treatment advice. Nurses in shelters would be able to monitor patients for any nefarious symptoms, such as a cough and fever, and promptly record symptoms for documentation.

2.4 Acute Patient Self-Care

"Jonathan" is a fresh-out-of-college intern at a major accounting firm. Recently at work, a nasty flu has been going around. Jonathan's long hours and poor diet results in him feeling "under the weather". One morning, he wakes up and has a severe sore throat, fever, muscle aches, and cough. He calls his doctor's office and is told that the wait time for an appointment is a few days out, and he should probably go to an urgent care center or stay home until he is feeling better. Jonathan is concerned that going to urgent care or the emergency room might be excessive. With seemingly no other option, he waits it out and returns to work as soon as he can after a few days. Feeling anxious about this happening again, he might scour the web and learn about the Illuminate™ device 5. He might decide that he would like to have the Illuminate™ device 5 on hand if this were to happen again. The following few weeks a cold is going around the office again, and sure enough he catches it. He could quickly take up the Illuminate™ device 5 and perform an exam on himself, for which he could promptly arrange a virtual consultation. The physician would look at his vitals and reassure him that he is just experiencing the cold that is going around his workplace environment. Feeling reassured, he would remain hydrated and would make a rapid recovery.

2.5 Traveling Patient

"Sarah" is a world traveler. She takes any and every opportunity she can to go abroad. Knowing that she has been in locations where a healthcare provider has been far out of range, or did not speak the same language as herself, she might procure an Illuminate™ device 5. Sure enough, on her trip to Ecuador, she starts feeling general malaise and severe stomach aches. She could then begin assessing herself using the Illuminate™ device 5, and she might discover that she has a low-grade fever. Sarah could then use the Illuminate™ device 5 to forward her medical data to a healthcare provider located at a medical facility. After a careful review of her symptoms and the data procured by the Illuminate™ device 5, the healthcare provider might conclude that she has a bad case of food poisoning. He might instruct her to take a dose of Pepto Bismol and continue that treatment until she can see a clinic for an antibiotic. Sarah could recover without the need for the antibiotic and, satisfied that she was able to be "seen" so quickly with all of the diagnostic data she needed for an exam, might ensure that she carries the Illuminate™ device 5 wherever she goes.

2.6 Chronic Patient Self-Care

"Eunice" is a sixty year old patient with diabetes. She lives a relatively active lifestyle and wants to stay ahead of the game in terms of handling her condition. To do this, she actively seeks out technology that helps her manage her medical condition most effectively. She might find the Illuminate™ device 5 from an internet search and conclude that it is just what she needs. She might like that the Illuminate™ device 5 can allow single tests, so she can measure her blood pressure, as well as document things like any wounds that are not healing properly, for a doctor to review. With the Illuminate™ device 5, Eunice might feel safer and happier knowing that help is only a phone call away.

2.7 Nursing/Advanced Care Homes

"Amy" is a nurse at a nursing home. She often finds herself inundated with patients that require more advanced care than her facility can offer. As a result, her patients often get sent to the hospital emergency department, where they are seen, assessed, and sent back—with significant cost, patient inconvenience and losses of information all along the way. Amy realizes that her patients have a disconnect in their care and wonders if there is a way to tackle that with existing solutions. She might come upon an ad about the Illuminate™ device 5 and see that it has diagnostic power and, unlike video conferencing alone, could provide physician guidance to interpret those results in real-time. She might also like the Review of Systems (ROS) feature (see below), especially as things can change in elderly individuals more quickly than those who are younger.

2.8 School Centers

"Sandra" is a Registered Nurse at St. Andrew's School. Though the complaints she receives often involve stomach aches and headaches, she sometimes gets kids coming in with a more insidious onset of symptoms. In cases like this she wishes she had more equipment to assess the children, but instead she has to send them to the emergency department for evaluation. While browsing the internet, she might notice an ad for the Illuminate™ device 5 and feels as though it might be just what she needs. She might order one and test it out—it would have everything she needs to perform a physical exam—allowing her to triage her patients far more effectively. As a result, Sandra notes that there are a lot fewer kids being shuttled to the hospital and parents who are happier they do not have to get a call that their child is in the hospital.

2.9 Airlines

"Eric" is a forty-three year old man who travels often for work. He finds himself at 30,000 feet with a sudden-onset chest pain. Profoundly anxious and not knowing what else to do, he pushes the button to call the flight attendant over. After the flight attendant arrives and hears what has been going on, she asks if any doctors are on board the flight. As there are none present, she calls a telemedical physician using the satellite phone. Not having enough information to make an informed decision, the physician suggests that the flight immediately divert and get the man to the hospital. The captain acts swiftly, and upon the final descent, Eric starts to feel better. An ambulance meets them on the taxiway and takes Eric to the emergency department, where he was diagnosed with trapped gas. If this scenario were played out differently, with an Illuminate™ device 5 onboard, Eric could have had his vitals immediately assessed and an ECG taken and transmitted to the physician using onboard Wi-Fi, and the whole situation could have been avoided.

3. Themes

3.1 Splash Screen

Figure 7:
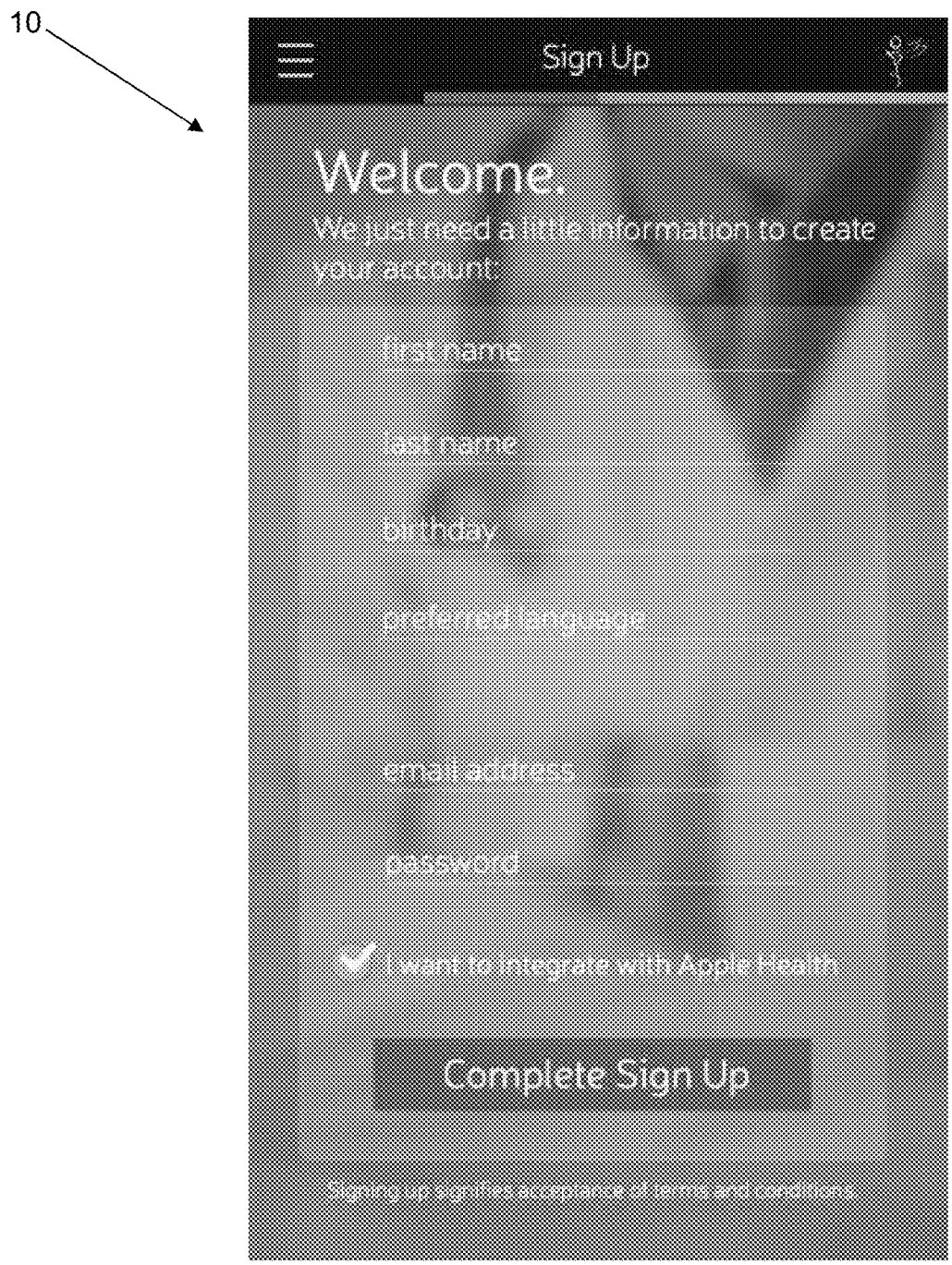
FIGS. 7-12 are schematic views showing exemplary screen displays for patient registration using the Illuminate™ device.
Figure 8:
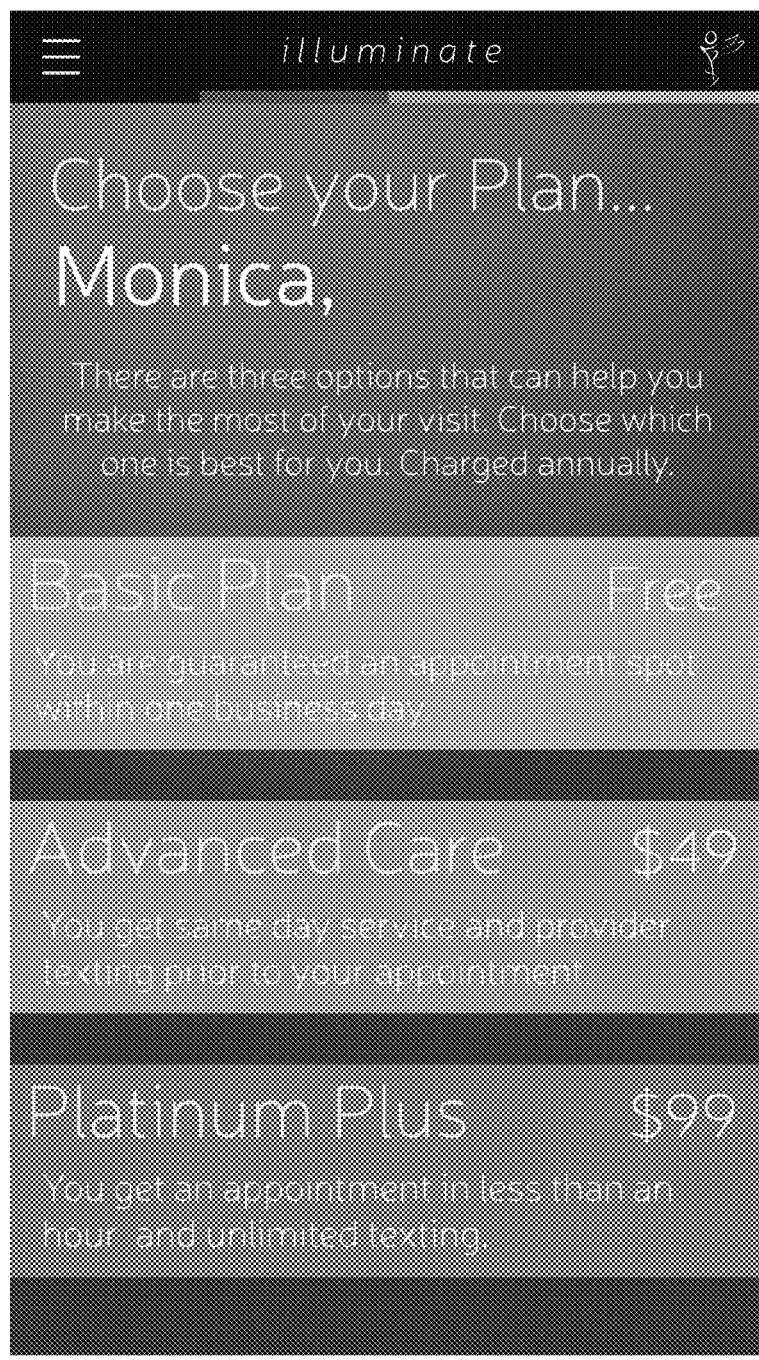
Figure 9:
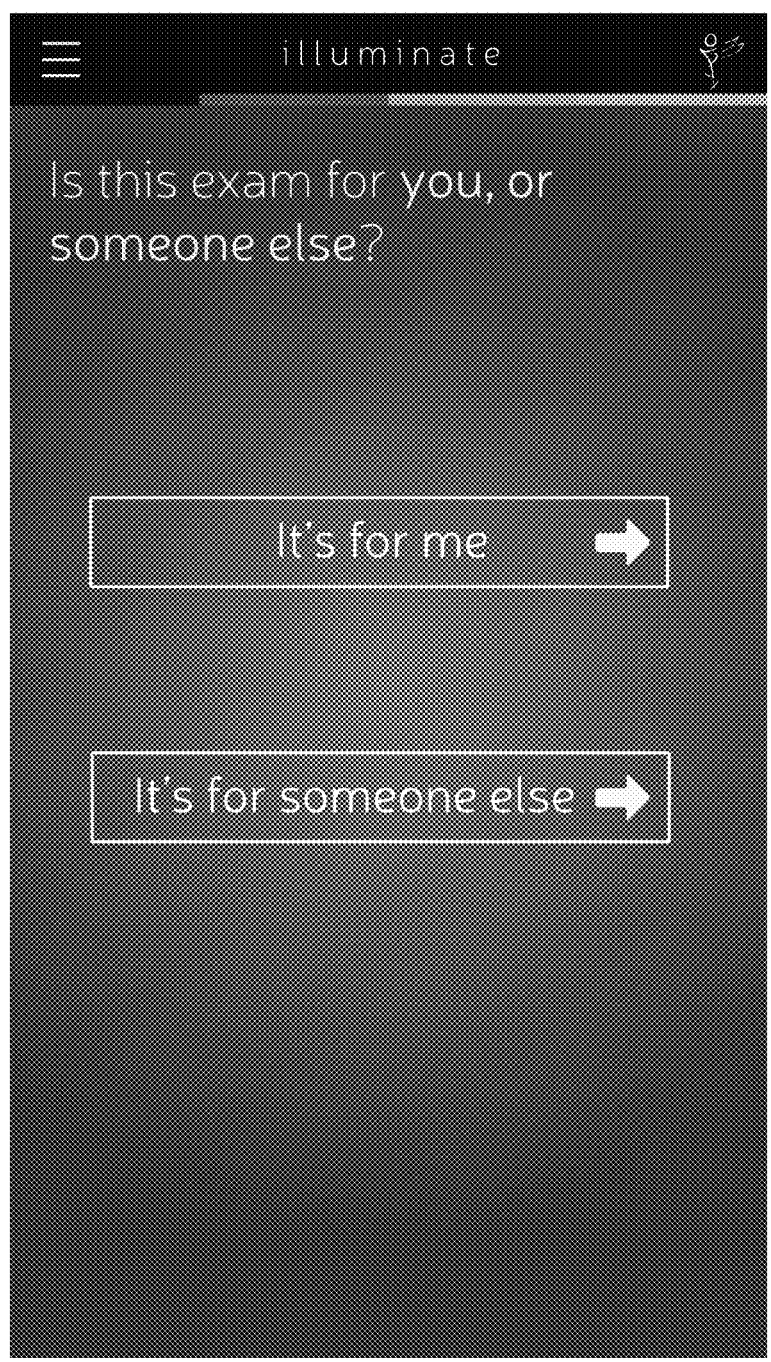
Figure 10:
Figure 11:
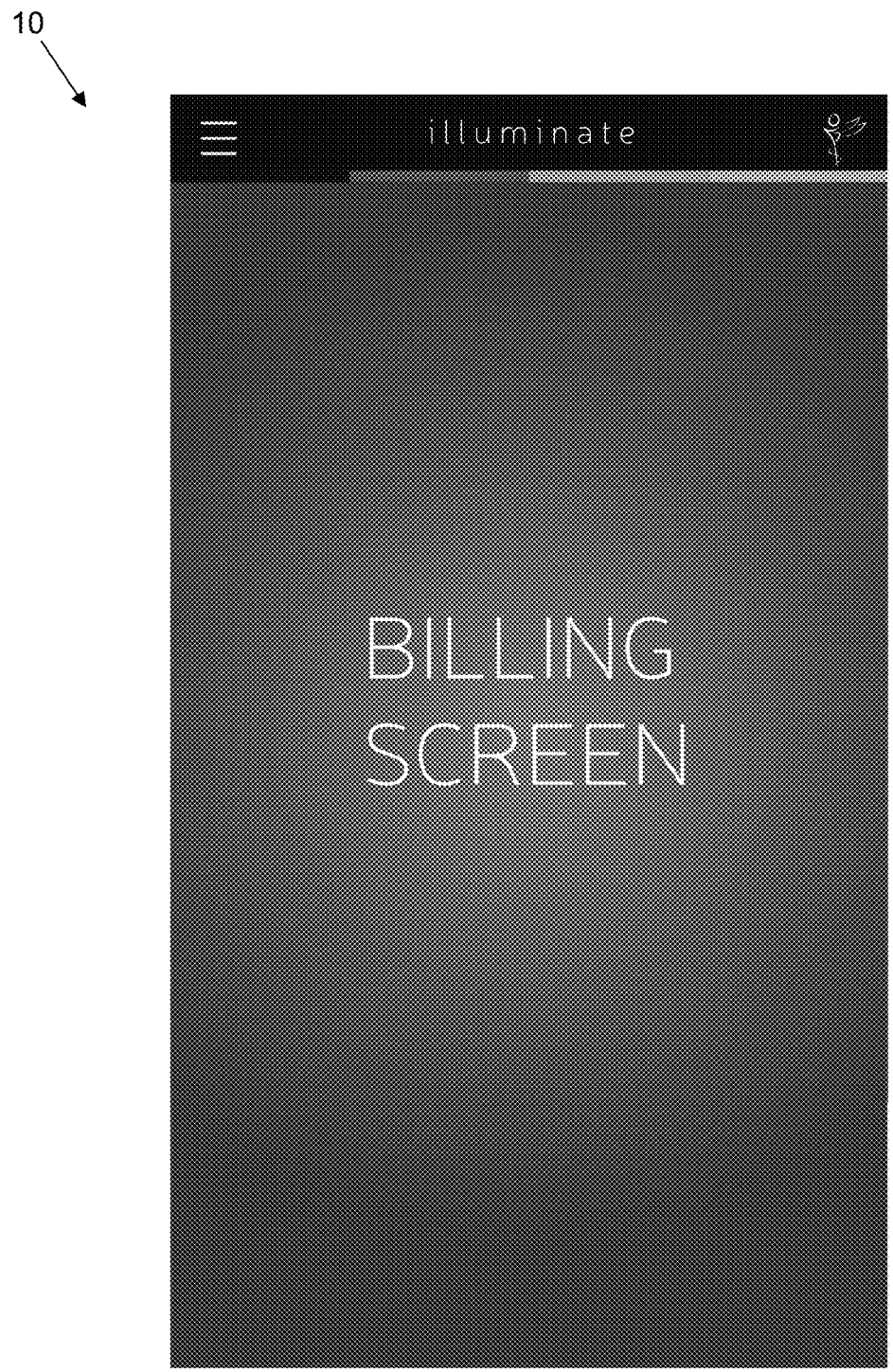
Figure 12:
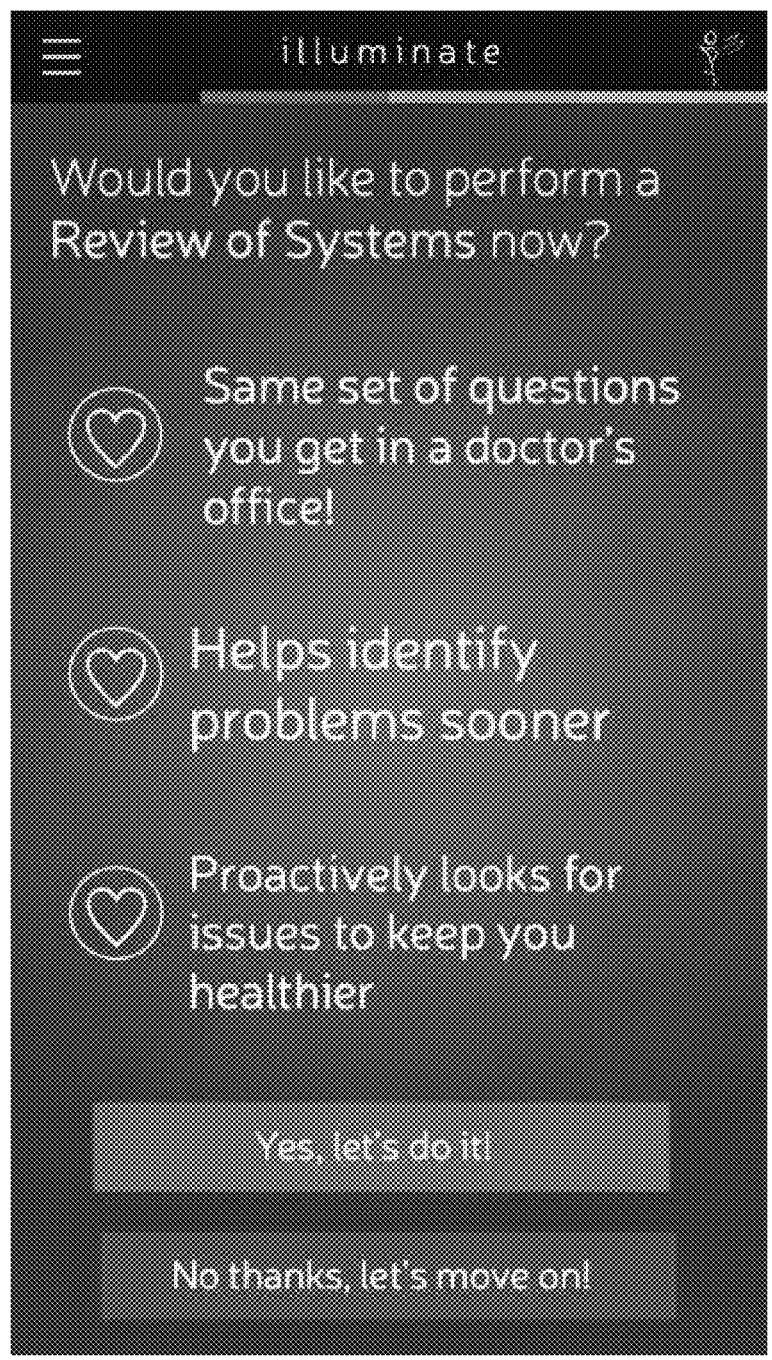

The splash screen shown in FIG. 1 preferably has an animated color bar while the app 10 (see FIG. 7) loads on the Illuminate™ device 5 (i.e., a smartphone app running on the smartphone component of the Illuminate™ device 5).

3.2 Color Theme

The color theme for the Illuminate™ device 5 is preferably the simple four-color combination shown in FIG. 2.

3.4 Text Theme

The text used for the Illuminate™ device 5 throughout the smartphone app is preferably "Neris" (https://www.fontsquirrel.com/fonts/neris).

4. The Illuminate™ Device 5

4.1 Core Use

The Illuminate™ device 5, though designed for eventual use by every individual desiring rapid and efficient primary medical care from the comfort of their own home, is principally targeted towards those in rural areas as well as primary care providers. The arrays of sensors (see below) on board the Illuminate™ device 5 are designed to allow efficient and accurate data collection and transfer to healthcare providers, whether activated by the patient or the provider themselves. The ability to videoconference after performing an exam further differentiates this product from others, as it is currently the only telemedicine device that has both features integrated in the same platform (i.e., onboard data sensing and transmission, and videoconferencing).

4.2 Secondary Use

The Illuminate™ device 5 also possesses features that enhance use by providers and patients. These features include, but are not limited to:

EasyAnalyze™—A smart triage system (implemented in app 10) designed to take the burden off the patient for choosing the medical tests to be run.

Dynamic Review of Systems (DROS)—After a patient fills in a typical initial intake review of various anatomical systems (i.e., the patient provides an initial set of information about their medical history), the app 10 running on the smartphone will ping the patient every so often to review answers taken from the review, including prompting the patient with subsets of questions relevant to the answers previously given. This process continues over time, keeping the information in the ROS updated without having to have the patient complete the form over and over again. As physicians identify conditions and update diagnoses, the ROS will identify subsets of questions that should be updated more frequently, keeping the physician abreast of any changes that need attention.

SmartSense™—Using machine learning, the accelerometer and gyroscope on board the Illuminate™ device 5 (i.e., contained in the smartphone component of Illuminate™ device 5 and accessed by app 10), as well as the camera input from the smartphone incorporated into the Illuminate™ device 5 (i.e., the smartphone component of Illuminate™ device 5 and accessed by app 10), the Illuminate™ device 5 will let the patient know when they are performing the exam correctly. This allows for automatic sensor data acquisition and increased accuracy of the results. By way of example but not limitation, the accelerometer and gyroscope work with app 10 to ensure that the Illuminate™ device 5 is in the proper orientation for specific tests and to allow proper measurements. For example, certain lung and heart sounds are easier to hear if someone is sitting up versus laying down or on their side. The Illuminate™ device 5 will know what position the device is in (upright versus lateral) by having app 10 read accelerometer and gyroscope data from the smartphone component of Illuminate™ device 5, and app 10 will prompt the user to make changes if needed. An exemplary physiological data acquisition might include an ultrasound, wherein the Illuminate™ device 5 is able to detect the progressive movement of the device across a limb or body part.

Of Note™—This feature of app 10 updates providers when there are certain conditions that place the patient at a greater likelihood of illness or require more thorough attention. This may include lab results, sensor data, or input from the patients themselves. This feature highlights small but important things that a provider might miss. An example might be a prescription medication interaction: if a patient who is suffering from a congenital heart disease takes certain antibiotics (e.g., a macrolide), they may be at higher risk for a fatal heart rhythm. Conventional telemedical consumer software does not scan for these things and telemedical providers often do not have the requisite history to be able to foresee these things. The Of Note™ feature of app 10 cross-references situations like these to let providers know if there is anything that could be an issue during treatment or later on. Other examples besides drug interactions may include abnormal patient input (arrhythmia noted on home scans without physician call, but highlighted on next visit with provider even if not prompted for the data) and the like.

Prelim AI™—The Prelim AI™ feature of app 10 uses library data to identify "fingerprint" regions in sensor data to preliminarily suggest diagnoses for medical conditions (e.g., "fingerprint" regions in audio waveforms for pulmonary and cardiac sounds obtained from the patient using the onboard stethoscope of the Illuminate™ device 5 could suggest pulmonary or cardiac conditions). Data from the sensors are assessed and where the data from the system suggests a potential condition, based on an algorithm output, this is recorded. Prelim AI™ works for any sensor output. Each sensor will require a working library to determine patterns for guiding potential diagnoses. This feature requires significant data that the Illuminate™ device 5 must procure before it will work.

5. The Illuminate™ Device 5 Hardware

The Illuminate™ device 5 is shown in FIGS. 3-5, 5A and 5B, and comprises a plurality of modules 15 which are physically mounted to a smartphone 20 and which wirelessly communicate with the smartphone 20. The smartphone 20 is running a smartphone app 10 (see FIG. 7) which controls operation of the smartphone 20, and which controls the plurality of modules 15 connected to the smartphone 20, so as to provide the functionality of the Illuminate™ device 5 as described herein. In this way, the modules 15 can acquire data from the patient, and the smartphone 20 can transmit that data to a remote healthcare provider or healthcare database. Data processing can be conducted at the modules 15, and/or at the smartphone 20, and/or at a remote healthcare site. The smartphone 20 also provides teleconferencing capability with a remote healthcare provider using the smartphone's onboard cellular telephone unit, camera, speaker, etc.

Thus, the complete Illuminate™ device 5 essentially comprises the plurality of modules 15 for gathering patient data, and the smartphone 20 for transmitting that patient data to a healthcare provider and for enabling teleconferencing with the healthcare provider, with the various components all working in combination with one another through the Illuminate™ smartphone app 10 which is running on the smartphone 20.

The plurality of modules 15 of the Illuminate™ device 5 preferably comprise:

(i) a sensor module 25 equipped with an IR thermometer 30, a single lead ECG 35, a stethoscope 40, and a pulse oximeter unit 45;

(ii) an otoscope module 50 equipped with a 3D printed macro lens holder 55 (containing appropriate optics) for providing otoscope functionality to the camera of the smartphone 20; and (iii) a Bluetooth™ blood pressure cuff 60.

The plurality of modules 15 of the Illuminate™ device 5 are intended to work with various components and features of smartphone 20. It will be appreciated that smartphone 20 typically comprises a CPU 65, memory 70 containing the software app 10, a display screen 75, a speaker/microphone 80, a cellular telephone unit/WiFi unit 85, a camera and flashlight unit 90, a Bluetooth unit 95 and a charger 100.

5.1 The Sensor Module 25

The sensor module 25 preferably comprises an IR thermometer 30, a single lead ECG 35, a stethoscope 40, and a pulse oximeter unit 45. These sensors are those most commonly used during a physical checkup with a healthcare provider. These sensors are easy to use and represent a step forward in moving data collection from the office into the home.

In one preferred form of the invention, the sensor module 25 also comprises an ultrasound unit 105 (see FIGS. 3, 4, 5A and 5B).

The sensor module 25 also comprises a Bluetooth™ unit 110 for enabling the various sensors to wirelessly communicate with the smartphone 20, and a USB-C charging port 115 for charging the sensor module 25.

(i) The IR thermometer 30 is designed to be placed next to the forehead of the patient. The IR thermometer sensor is recessed and needs to be close to the forehead of the patient in order to record the temperature accurately. The user places the device on the forehead of the patient with the stethoscope 40 touching the forehead of the patient (it is the most protruding part of the Illuminate™ device 5) and presses a button on the smartphone screen 75 to record the temperature of the patient. Note that the sensor module 25 is attached to the back of the smartphone 20 so that the sensors of the sensor module 25 face the patient while the display screen 75 of the smartphone 20 (which displays instructions, operating buttons and data results) faces the user. The IR thermometer 30 uses a special lens to focus infrared light from an object onto a detector. In this case, the object is the forehead of the patient and the light emitted from an individual gets concentrated onto a thermopile detector to get a reading. The reading is within 0.1 degree Celsius. The data page for one preferred form of the IR thermometer 30 is accessible at:
https://www.melexis.com/media/files/documents/product-flyers/mlx90614-product-flyer-melexis.pdf.

(ii) The single lead ECG 35 records the electrical rhythm of the heart. A patient can tap a button on the smartphone screen 75 and place one finger from each hand on the two stainless-steel ECG sensor pads 120 and the Illuminate™ device 5 records the patient's heart rhythm over 15 seconds. The ECG information is stored in the patient file of the Illuminate™ smartphone app 10 running on the smartphone 20 and sent to a physician for analysis.

(iii) The stethoscope 40 is used to listen to heart and lung sounds. This feature may be reserved for physician use only, but is intended to eventually be used by patients to record their own heart and lung sounds (with a friend/caretaker holding the device to the appropriate parts of the patient's body if necessary). The stethoscope 40 uses a microphone assembly to record and amplify the heart and lung sounds. The sounds, and the waveforms of the sounds, are collected and stored in the Illuminate™ smartphone app 10 running on the smartphone 20, and both audio recordings and waveforms are available for a physician to analyze in the patient file. The stethoscope 40 is preferably powered using a MEMS microphone. The MEMS microphone picks up sound waves condensed from the bell of the stethoscope, which makes an isolated seal with the patient's skin using a black silicone band 125 at the edge of the bell ring of stethoscope 40. The component data sheet for one preferred form of stethoscope is accessible at:
https://www.mouser.com/ds/2/218/SPW2430HR5H-B-1290924.pdf.

(iv) The pulse oximeter unit 45 measures the levels of oxygen in the blood. The patient taps a button on the display screen 75 of smartphone 20 and then places their finger comfortably on the pulse oximeter sensor 45 in the depression. The sensor then uses IR and red light to determine the levels of oxygen in the blood and records the data in the patient file of the Illuminate™ smartphone app 10 running on the smartphone 20. The pulse oximeter unit 45 is reflective, and when the patient touches the sensor, gets data sent back as a function of reflectance versus transmittance. The data sheet for one preferred form of pulse oximeter is available at:
https://www.mouser.com/new/maximsensors/maxim-max30102efd-sensor/.

(v) The ultrasound unit 65 on the sensor module 25 uses sound waves at high frequencies to generate images of the inside of the body without the use of ionizing radiation. In one preferred method of use, sensor module 25 is dismounted from smartphone 20 so that the emitter/receiver of ultrasound unit 65 can be conveniently placed against the tissue of the patient, with data from sensor module 25 being wirelessly transmitted to smartphone 20 (see below). The patient taps a button on the display screen 75 of smartphone 20 to activate the ultrasound unit 65, then chooses the area (using an anatomical representation of the human body shown on the display screen 75 of the smartphone 20) where they intend to scan. The choice of body location determines the scanning pattern which the patient will be advised to use to scan the area appropriately. The ultrasound unit 65 will store images locally and transmit them to the smartphone over the Bluetooth (e.g., BLE™) connection. The data from the images will correlate with certain sensors for assessment of conditions (e.g., both ECG and stethoscope output for cardiac echocardiography and thermometer output for assessment of deep vein thromboses, also commonly referred to as DVTs).

(vi) The Bluetooth™ unit 110 on the sensor module 25 is configured to wirelessly communicate with the Bluetooth™ unit 95 on the smartphone 20 so that the various sensors on the sensor module 25 can wirelessly communicate with the smartphone 20.

(vii) A USB-C port 115 for charging the sensor module 25 (which preferably also includes one or more batteries, not shown).

In one preferred form of the invention, the sensor module 25 also comprises:

(viii) an accelerometer (not shown, but similar to the accelerometer commonly provided on smartphone 20): for one preferred form, see http://www.st.com/resource/en/datasheet/Ism6ds33.pdf;

(ix) a gyroscope (not shown, but similar to the gyroscope commonly provided on smartphone 20);

(x) an LED light ring (not shown) that glows around the edge of the sensor module 25 from the inside to show status of sensor module 25 (e.g., such as when data is being recorded);

(xi) an encoder and audio codec (not shown): for one preferred form, see http://www.vlsi.figileadmin/datasheets/vs1063ds.pdf;

(xii) a voltage regulator (not shown): for one preferred form, see https://www.digikey.com/product-detail/en/microchip-technology/MIC55283.3YMT-TR/576-4766-1-ND/4864030;

(xiii) a linear amplifier (not shown): for one preferred form, see https://www.digikey.com/product-detail/en/diodes-incorporated/LMV358SG13/LMV358SG-13DICT-ND/2182572;

(xiv) a flash memory (not shown) for audio data storage: for one preferred form, see https://www.digikey.com/product-detail/en/adesto-technologies/AT25SF161-MHD-T/1265-1257-1-ND/6827210;

(xv) an On/Off toggle switch (not shown); and (xvi) a Wireless Charging Pad (not shown).

In one preferred form of the invention, the sensor module 25 comprises two sections: (i) an adapter body 130 (see FIG. 5A) for mechanically connecting to the smartphone 20, and (ii) a sensor body 135 for mechanically connecting to the adapter body 130. The sensor body 135 carries all of the aforementioned sensors, and is mechanically connected to the smartphone 20 via the adapter body 130. This arrangement allows for appropriate adapter bodies to be provided for a range of different smartphones, and a single universal sensor body 135 to be used with any of the various adapter bodies 130. In this way, a universal sensor body 135 can be provided which will work with a range of different smartphones via appropriate adapter bodies 130. In addition, if desired, different sensor bodies 135 can be provided for providing different sensor functionality. Where the sensor module 25 comprises two sections (e.g., the adapter body 130 and the sensor body 135), the two sections preferably mate in such a way as to minimize locations where germs might reside (e.g., the two sections mate with such high precision as to essentially constitute a singular element).

In one preferred form of the invention, the adapter body 130 comprises edge flanges 140 which make a close sliding fit to the edges of the smartphone 20, whereby to mechanically connect the adapter body 130 to the smartphone 20. The adapter body 130 also comprises a plurality of connector pins 145 which are mechanically secured to the adapter body 130. The sensor body 135 comprises a plurality of recesses (not shown) on the underside of the sensor body 135 for receiving the connector pins 145 of the adapter body 130 and for mechanically connecting the sensor body 135 to the adapter body 130 (and hence mechanically connecting the sensor body 135 to the smartphone 20). In practice, the sensor body 135 is left mounted to the adapter body 130. The sensor module 25 can be charged using its USB-C port 115, or the wireless charging pad (see above) using the smartphone 20 as an energy source, and the smartphone 20 can be charged using its onboard charging port 100. When the sensor module 25 is to be used, it is preferably mounted as a unit (i.e., with the sensor body 135 already attached to the adapter body 130) to the smartphone 20.

Note that when ultrasound unit 105 is to be used, and ultrasound unit 105 is to be dismounted from smartphone 20 so as to facilitate convenient positioning the emitter/receiver of ultrasound unit 65 against the tissue of the patient, sensor body 135 may be detached from adapter body 130 (with adapter body 130 remaining attached to smartphone 20). Alternatively, sensor body 135 may remain attached to adapter body 130, and adapter body 130 and sensor body 135 may be detached as a unit from smartphone 20, whereby to facilitate convenient positioning the emitter/receiver of ultrasound unit 65 against the tissue of the patient.

In another preferred form of the invention, the sensor module is formed with a singular construction (i.e., the functionality of the sensor body 135 and the adapter body 130 are provided in a single, integral housing).

Also, if desired, sensor body 135 may be connected to the adapter body 130 using means other than connector pins 145, e.g., sensor body 135 may be connected to the adapter body 130 through the use of magnets (not shown) which are recessed in both the sensor body 135 and adapter body 130.

5.2 The Otoscope Module 50

The otoscope is a tool used to look in the ears, nose, and throat of a patient. The otoscope module comprises a 3D printed macro lens holder 55 (containing appropriate optics) for providing otoscope functionality to the camera and flashlight unit 90 of the smartphone 20 (a disposable specula, not shown, is positioned over 3D printed macro lens holder 55 during use of otoscope module 50). The otoscope module 50 fits on the top of the smartphone 20 and uses the built-in smartphone camera and flashlight unit 90 to get pictures of the patients' eardrums, nose, and throat/tonsils. The 3D printed macro lens holder 55 has a lens that allows the camera on the smartphone to zoom in and out, and to focus properly, at such a close distance.

5.3 The Bluetooth™ Blood Pressure Cuff 60

Blood pressure cuff 60 is of the sort well known in the art for obtaining readings of the patient's blood pressure, and comprises a blood pressure sensor which is Bluetooth™ compatible, and a blood pressure cuff which is a Bluetooth™ compatible.

5.4 System Schematic

Figure 5:
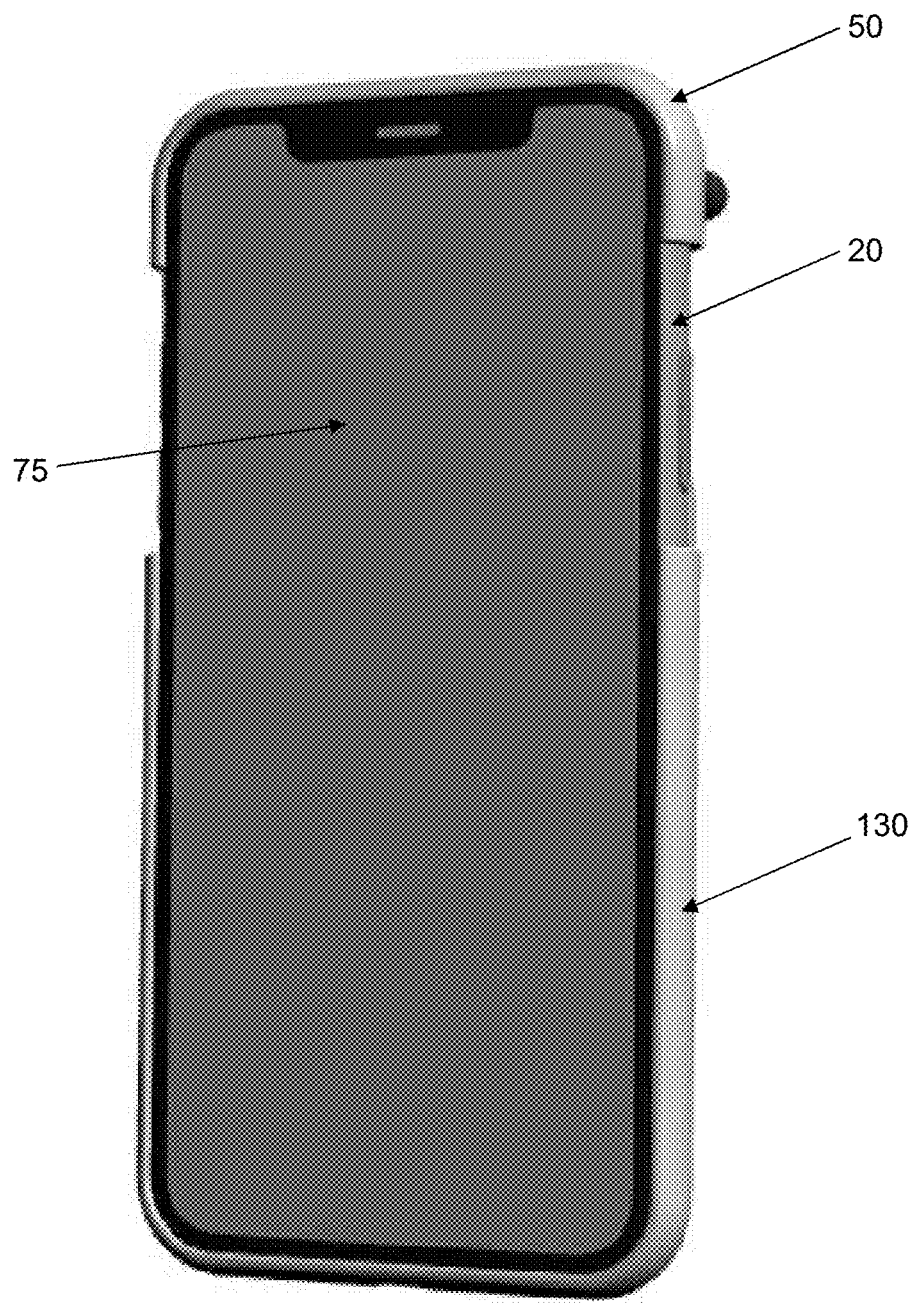
Figure 5A:
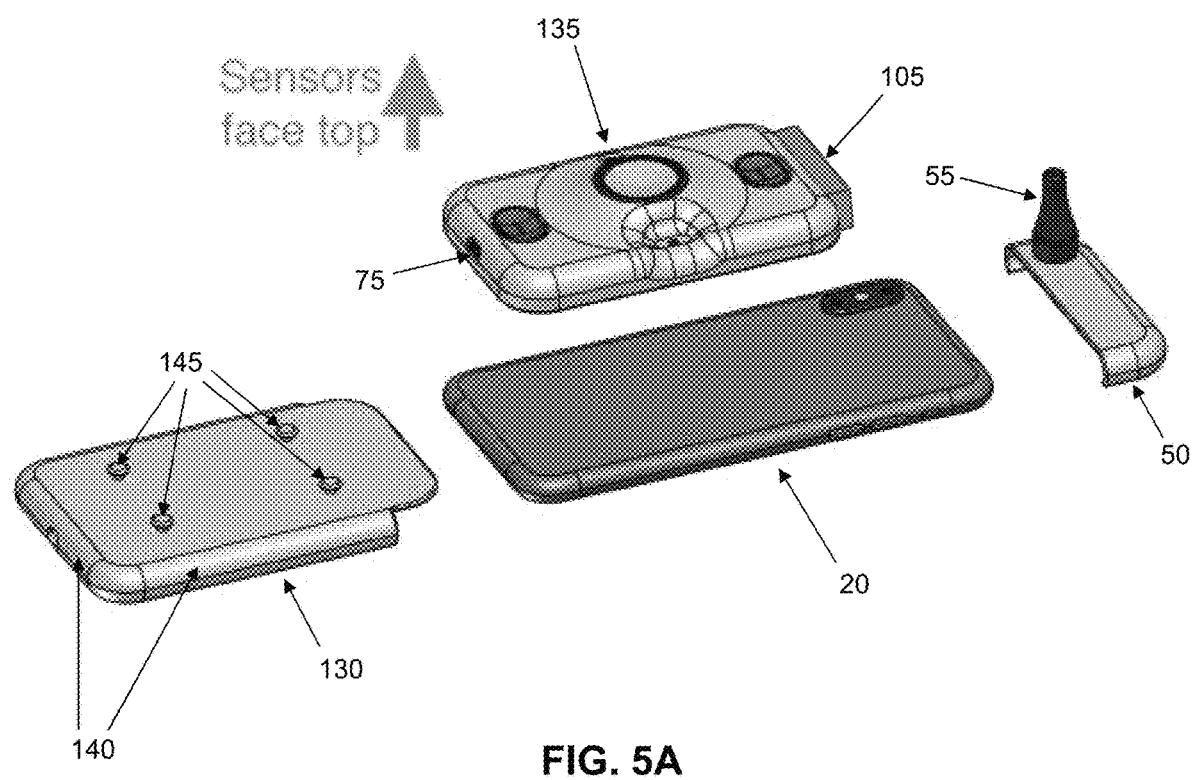
Figure 5B:
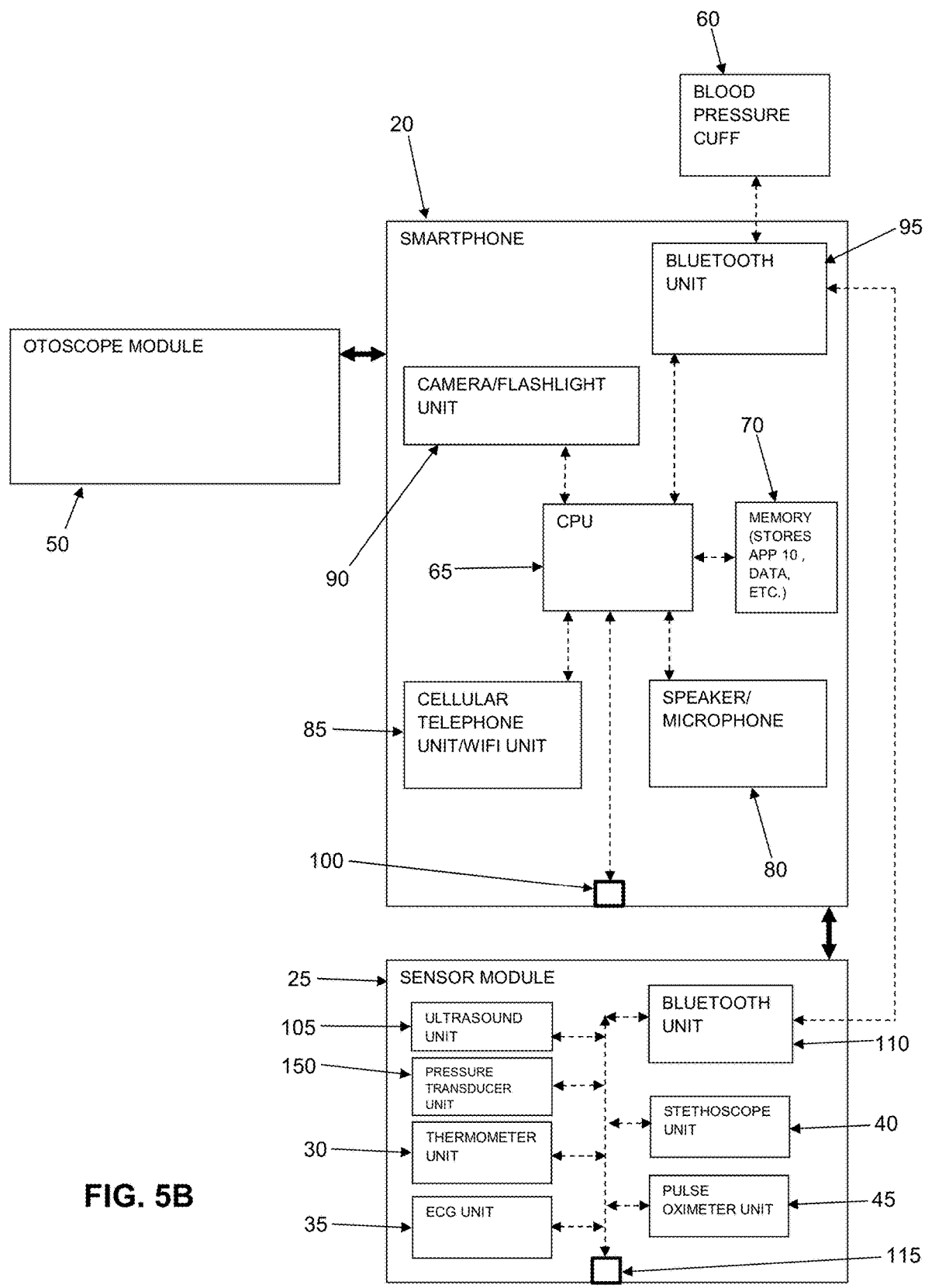
Figure 5C:
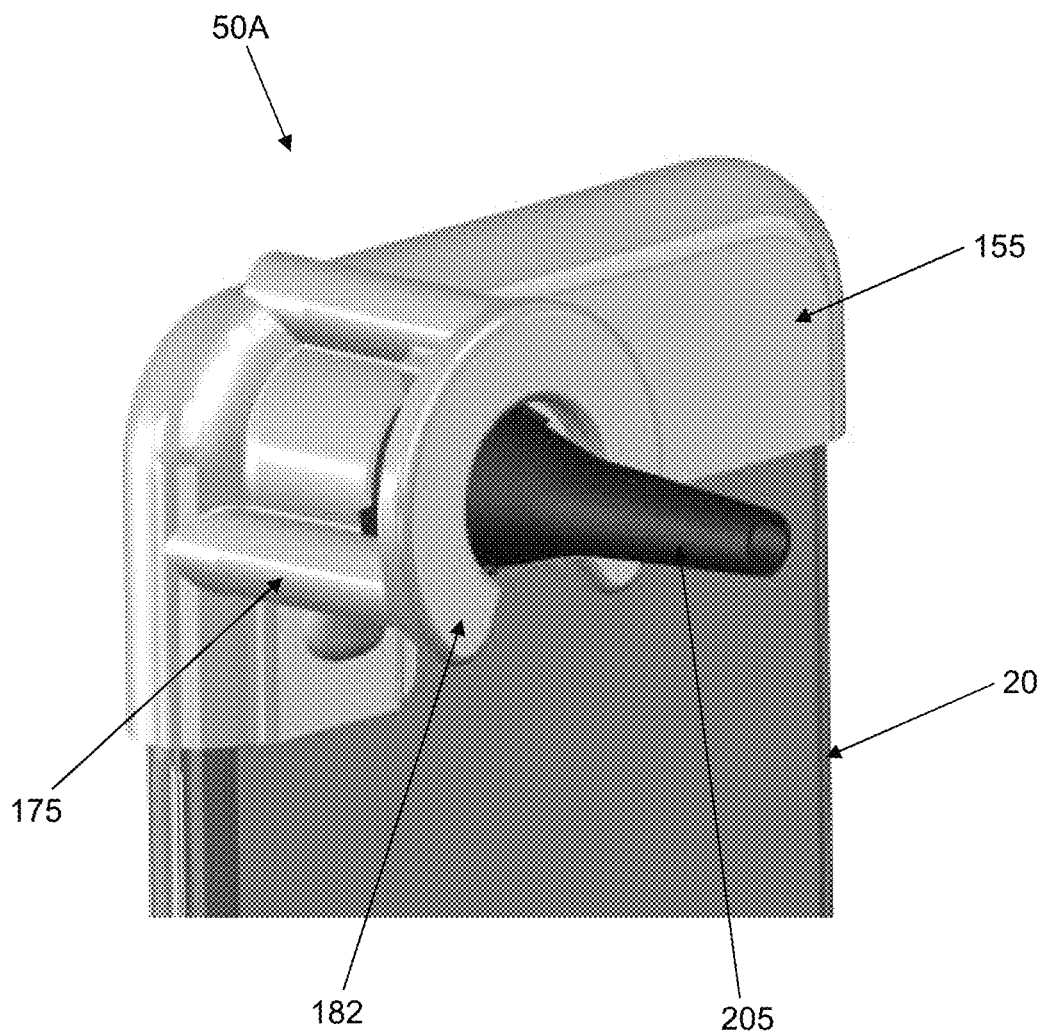
Figure 5D:
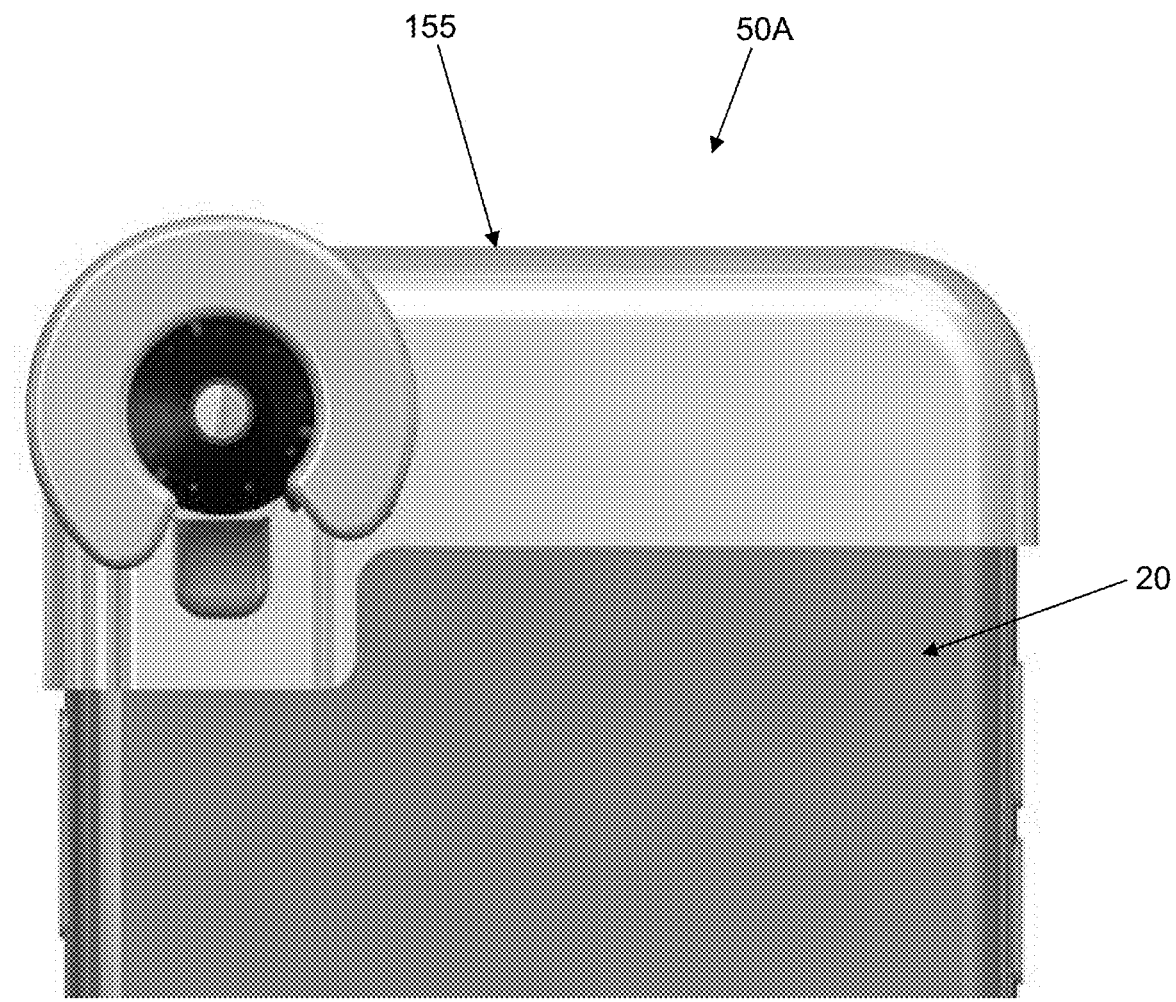
Figure 5E:
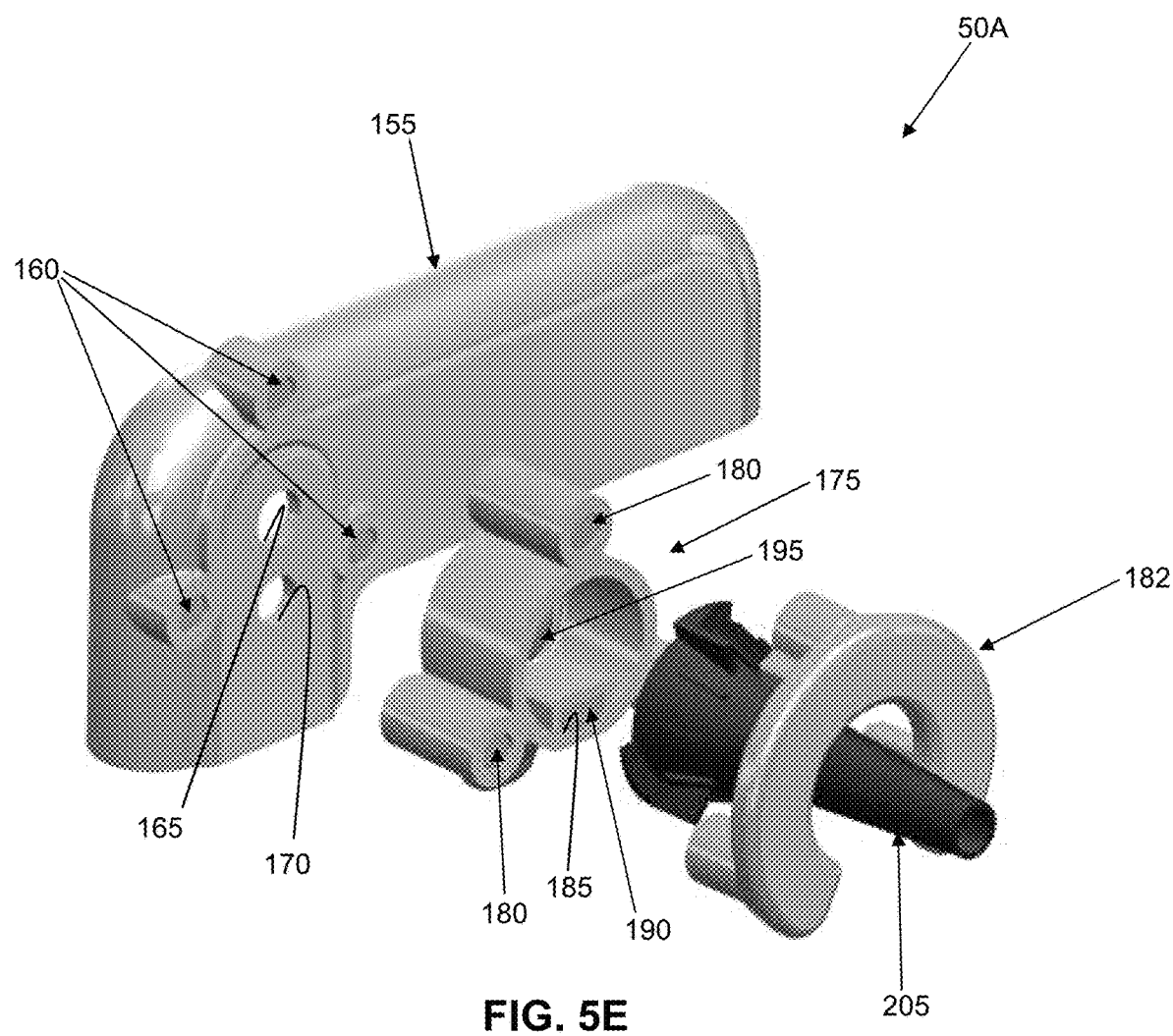
Figure 5F:
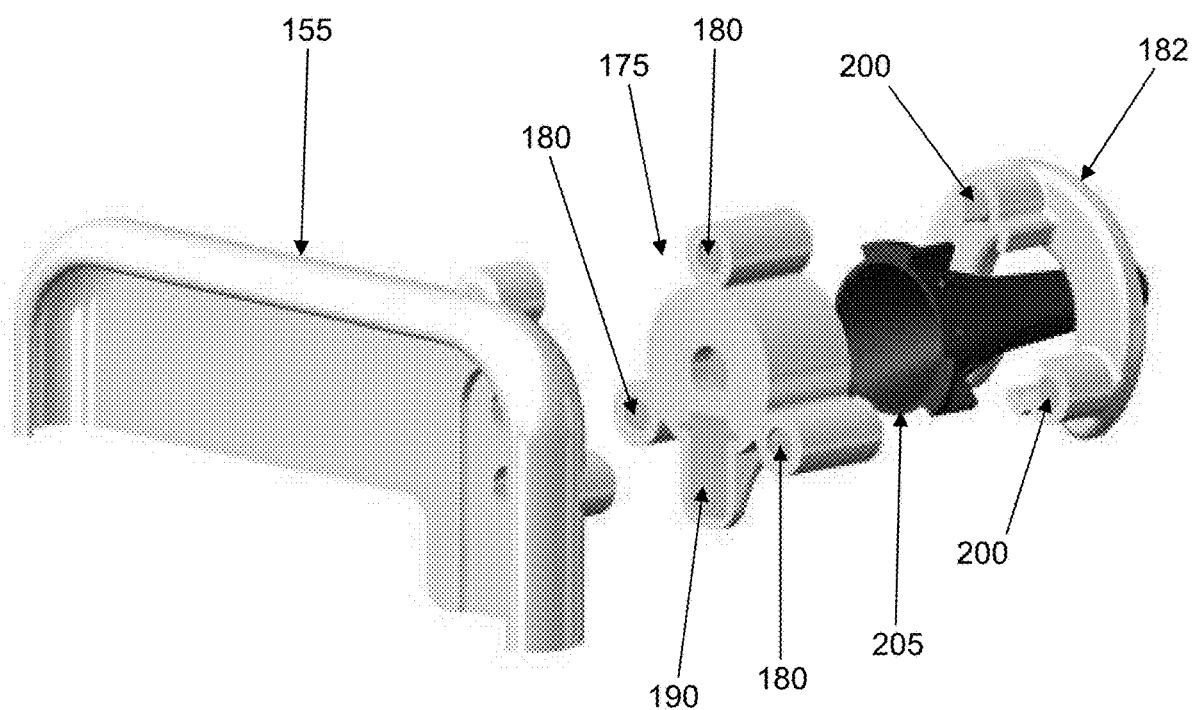

FIG. 5B is a high-level system schematic showing how the sensor module 25, otoscope module 50 and Bluetooth™ blood pressure cuff 60 communicate with the smartphone 20 using the Illuminate™ smartphone app 10 running on the smartphone 20.

5.5 Alternative Ultrasound Unit for Measuring Blood Pressure

As discussed above, Illuminate™ device 5 preferably comprises an ultrasound unit 105 for imaging the anatomy of the user, and a blood pressure cuff 60 for measuring the blood pressure of the user. However, if desired, the ultrasound module 105 may be used to measure the blood pressure of the user.

More particularly, in this form of the invention, and looking now at FIG. 5B, sensor module 25 further comprises a pressure transducer unit 150 which is disposed against the base of the ultrasound unit 105 so as to measure the pressure which may be applied by ultrasound unit 105 against tissue.

This allows the pressure applied against tissue by the ultrasound unit 105 to be correlated with images simultaneously acquired by the ultrasound unit 105 at discrete and instantaneous time points. In view of the foregoing, ultrasound unit 105 may be pressed against the minor axis of a muscular artery and images generated by ultrasound unit 105 may be used to determine when the artery is fully closed. The pressure read by pressure transducer unit 150 is recorded when the artery is fully closed. Then the user can progressively relax the force with which ultrasound unit 105 is pressed against the tissue, and images generated by ultrasound unit 105 may be used to determine when the artery is fully open. The pressure read by pressure transducer unit 150 is recorded when the artery is fully open. Thus, the systolic and diastolic blood pressure of the user can be determined using ultrasound unit 105 and pressure transducer unit 150.

5.6 Alternative Otoscope Module

As discussed above, if desired, Illuminate™ device 5 preferably comprises an otoscope module for visualizing the interior of a body orifice (e.g., the ear). If desired, and looking now at FIGS. 5C-5F, in an alternative form of the invention, there is provided an otoscope module 50A configured to mount to cameras of various sizes and camera configurations. More particularly, in this form of the invention, the otoscope module 50A comprises three different components: (i) an otoscope adapter body 155 which comprises a plurality of magnetic mounts 160, the otoscope adapter body 155 being sized to mount to a smartphone of a particular size and having openings 165, 170 to align with a particular smartphone's camera and LED light source, respectively, (ii) an otoscope optic body 175, which is universal and contains magnets 180 at the front and back sides of the otoscope optic body (i.e., for mounting the otoscope optic body to the otoscope adapter body 155 and a speculum holder body 182, see below) as well as a channel 185 for a fiber optic 190 and a lens 195 for focusing light emitted by the LED light source of the smartphone toward the area imaged by the camera of the smartphone, and (iii) the speculum body holder 182, which is mounted via one or more magnets 200 to the front of the otoscope optic body 175, the speculum body holder 182 being configured to allow for easy mounting and removal of a speculum 205 (e.g., a single-use, disposable speculum) for examination purposes.

In one preferred form of the invention, the otoscope adapter body 155 is configured to mount to most smartphones, while the otoscope optic body 175 comes in a variety of different configurations so as to accommodate the varying camera and LED light configurations of various smartphones.

6. The Illuminate™ Software (i.e., the Illuminate™ Software App 10)

6.1. Registration

When patients or providers download the Illuminate™ app 10 onto their smartphone 20, they are prompted to register for an account. Provider accounts require verification prior to being allowed to interact with patients.

6.1.1. Patient Registration

Figure 6:
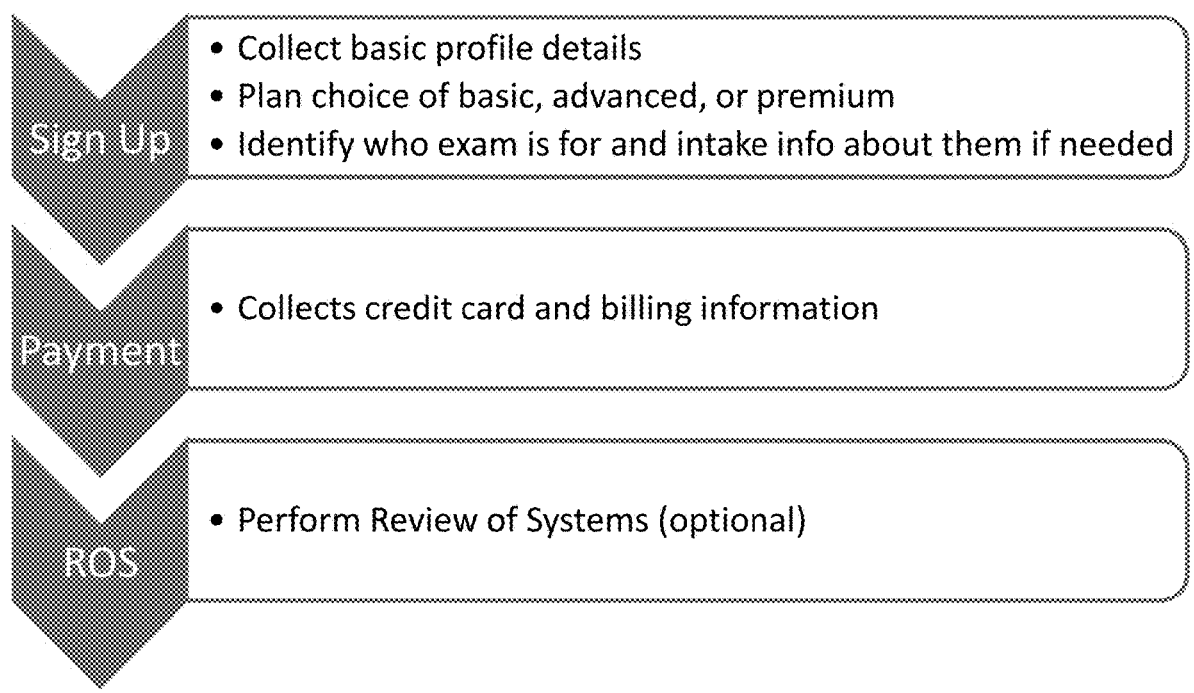
FIG. 6 is a schematic view showing an exemplary workflow for patient registration using the Illuminate™ device.

The workflow for the patient registration is shown in FIG. 6.

Exemplary screen displays for patient registration are shown in FIGS. 7-12.

6.1.2 Provider Registration

Providers follow a similar registration process, with the option to link to a payment-receiving processor at the time of sign-up. Before any exams are performed, ID and practice verification must be performed manually in a superadmin portal.

Figure 13:
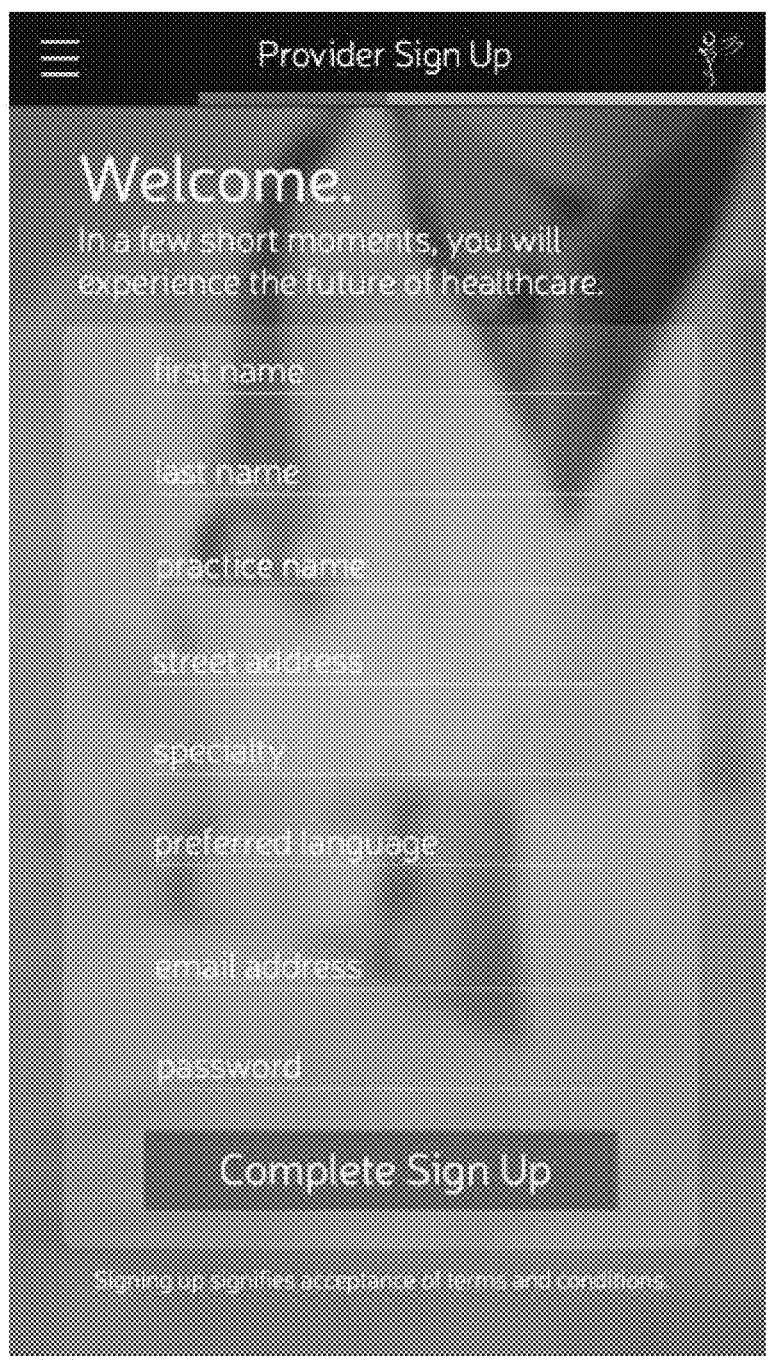
FIGS. 13 and 14 are schematic views showing exemplary screen displays for provider registration using the Illuminate™ device.
Figure 14:
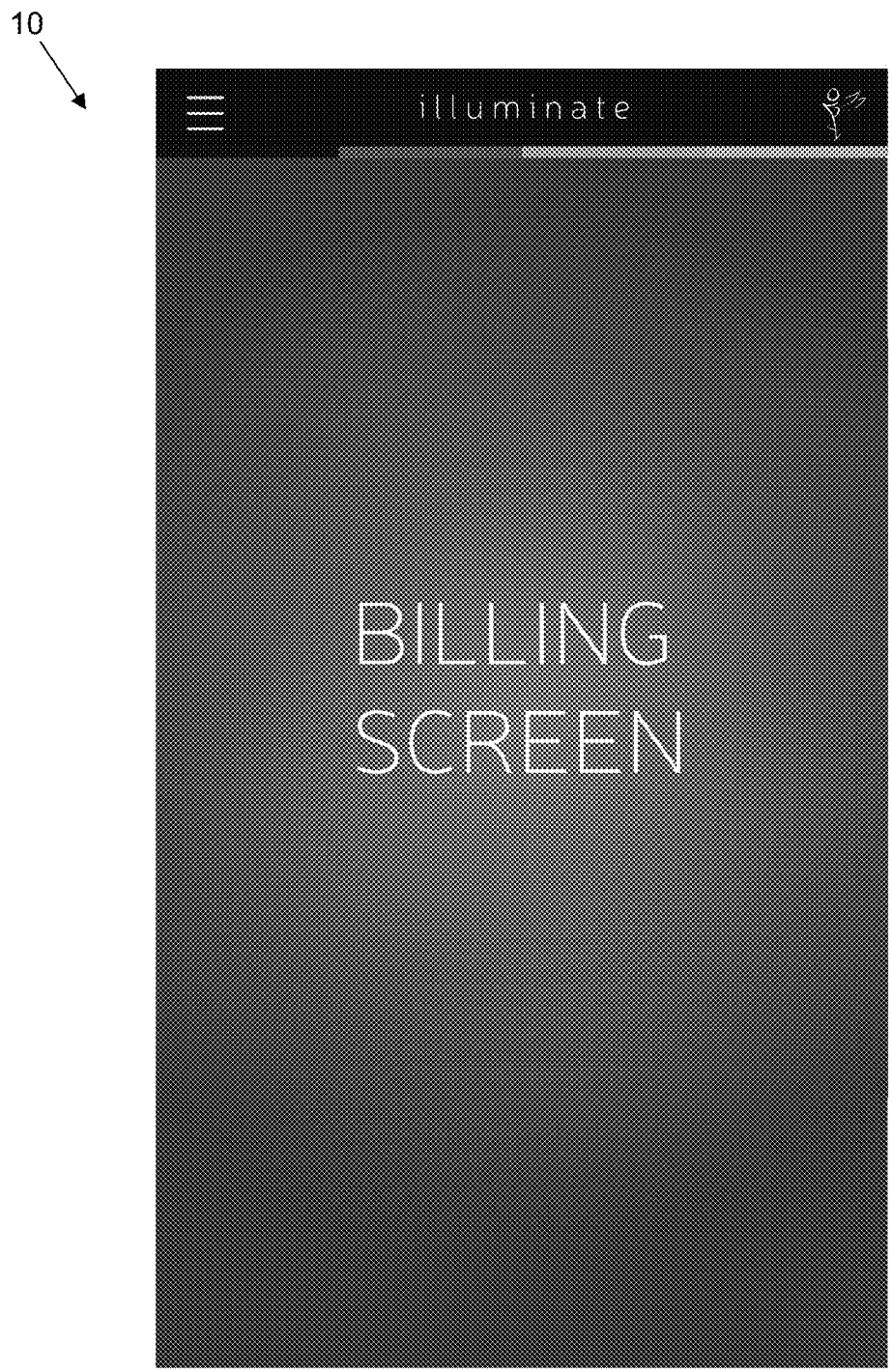

Exemplary screen displays for provider registration are shown in FIGS. 13 and 14.

6.2 Performing an Exam—Patient Side

After the patient registers an account on the Illuminate™ device smartphone app 10, they can go to their profile, perform an exam using EasyAnalyze™, or perform a specific test using the manual selection of tests. This is all done through the Illuminate™ smartphone app 10 which is running on their smartphone 20.

6.2.1 EasyAnalyze™

The EasyAnalyze™ decision tree (implemented through the EasyAnalyze™ feature of the Illuminate™ smartphone app 10) simplifies things for the patient by removing the workload of determining which tests to run, and provides for more rapid analysis of patient data by healthcare providers by aggregating information by relevant body system and highlighting issues for the providers (e.g., in the Of Note™ section of the provider screen). In addition to selecting which tests should be run for patient assessment (and which sensors should be used for those tests) and guiding patients through the tests, the follow-up function of the EasyAnalyze™ feature reminds the patient to take further tests to analyze trends in patient recovery and aid in completing the diagnostic picture for the physician. The ultimate goal for EasyAnalyze™ is to take reported patient symptoms, suggest a set of tests, identify which sensors will be used for those tests and guide the patient through those tests, and assess the results of those tests by comparing them to the reported symptoms to create a preliminary diagnosis that can then be reviewed by a physician for interpretation.

6.2.1.1 How EasyAnalyze™ Works

When the patient selects the EasyAnalyze™ option, they are taken to a 3D, gendered representation of an outline of a human body. The patient touches on the outline of the human body at those locations where they are feeling unwell, and a submenu (specific to that area of the body) opens with pointers to more specific symptoms. These pointers may then be selected as appropriate by the patient. Then the patient can return to the outline of the human body to indicate other areas of the body where they are experiencing symptoms, and again follow a submenu specific to the area of the body selected to identify more specific symptoms. Based on the symptoms selected, individual sensor tests are identified and queued until the patient signals that they are finished inputting their symptoms. Upon completion, the Illuminate™ device begins the cycle of tests via sensor acquisition by showing the patient a prompt with a 3D representation of how to perform the test.

The specific symptoms from the submenues are logged along with the acquired sensor data and compiled into the patient's list of complaints—allowing easy transfer of the data to a physician for diagnosis without the patient or physician having to unnecessarily type in data.

6.2.1.2 Workflows for EasyAnalyze™

In one form of the invention, EasyAnalyze™ uses a pre-defined list of tests when a given symptom is selected. For each of the sensors used in a particular test, the specified follow-up period is listed if applicable. FIG. 15 shows an exemplary pre-defined list of tests when a given symptom is selected, including the specific follow-up period where appropriate.

Figure 16:
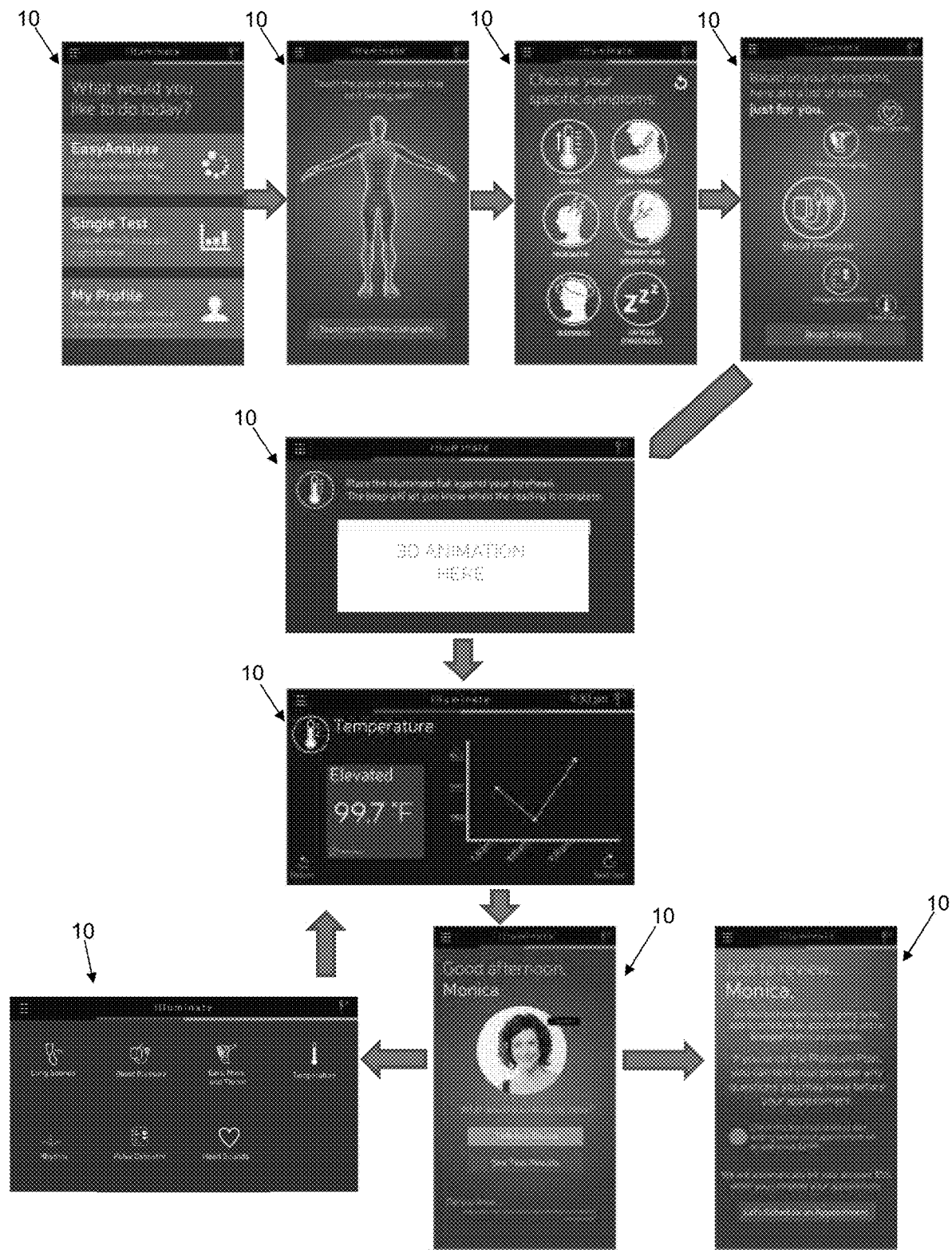
FIG. 16 is a schematic view showing an exemplary workflow for the EasyAnalyze™ feature of the software of the Illuminate™ smartphone app.
Figure 17:
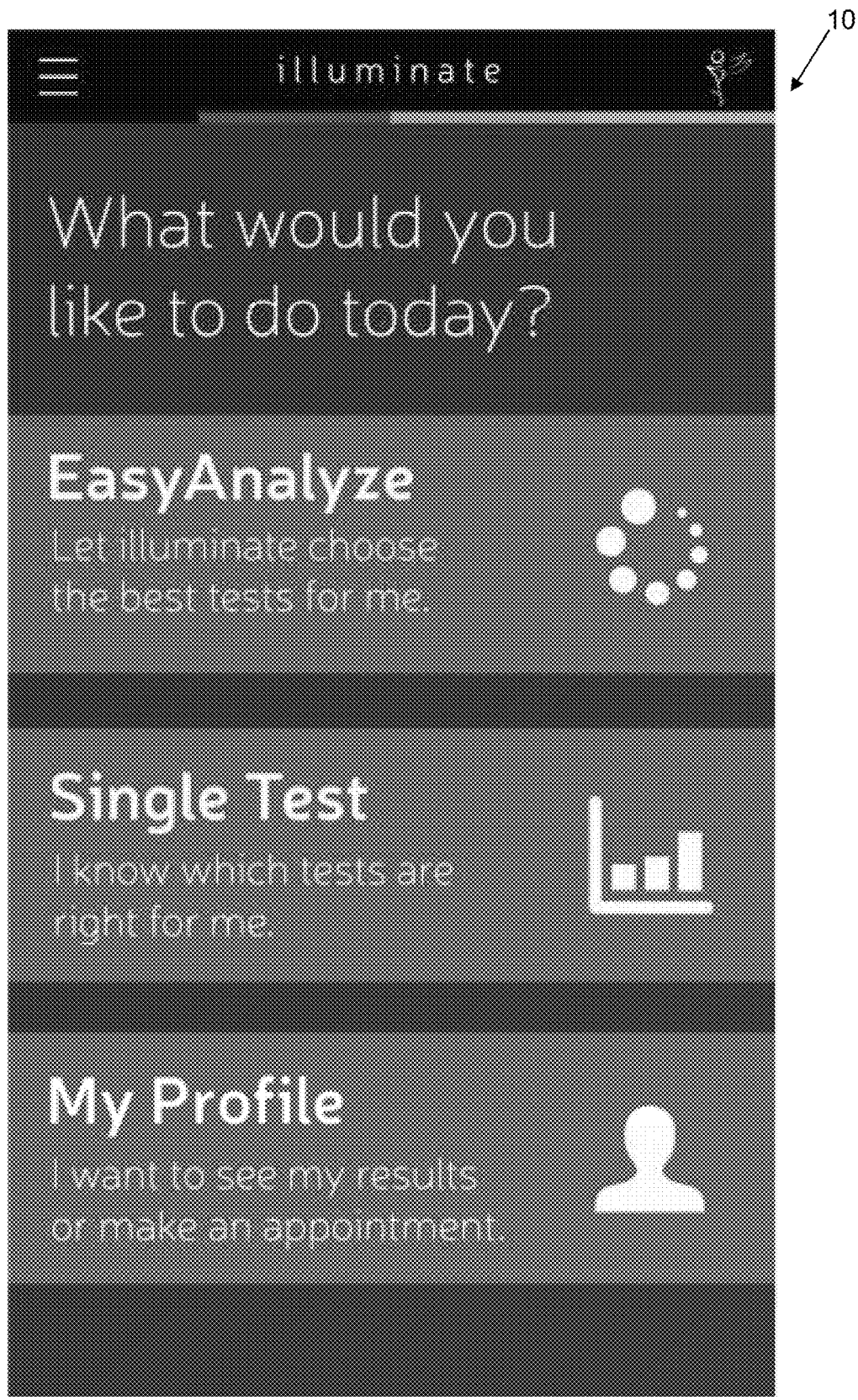
FIGS. 17-25 are schematic views showing enlargements of each of the screen displays in FIG. 16.
Figure 18:
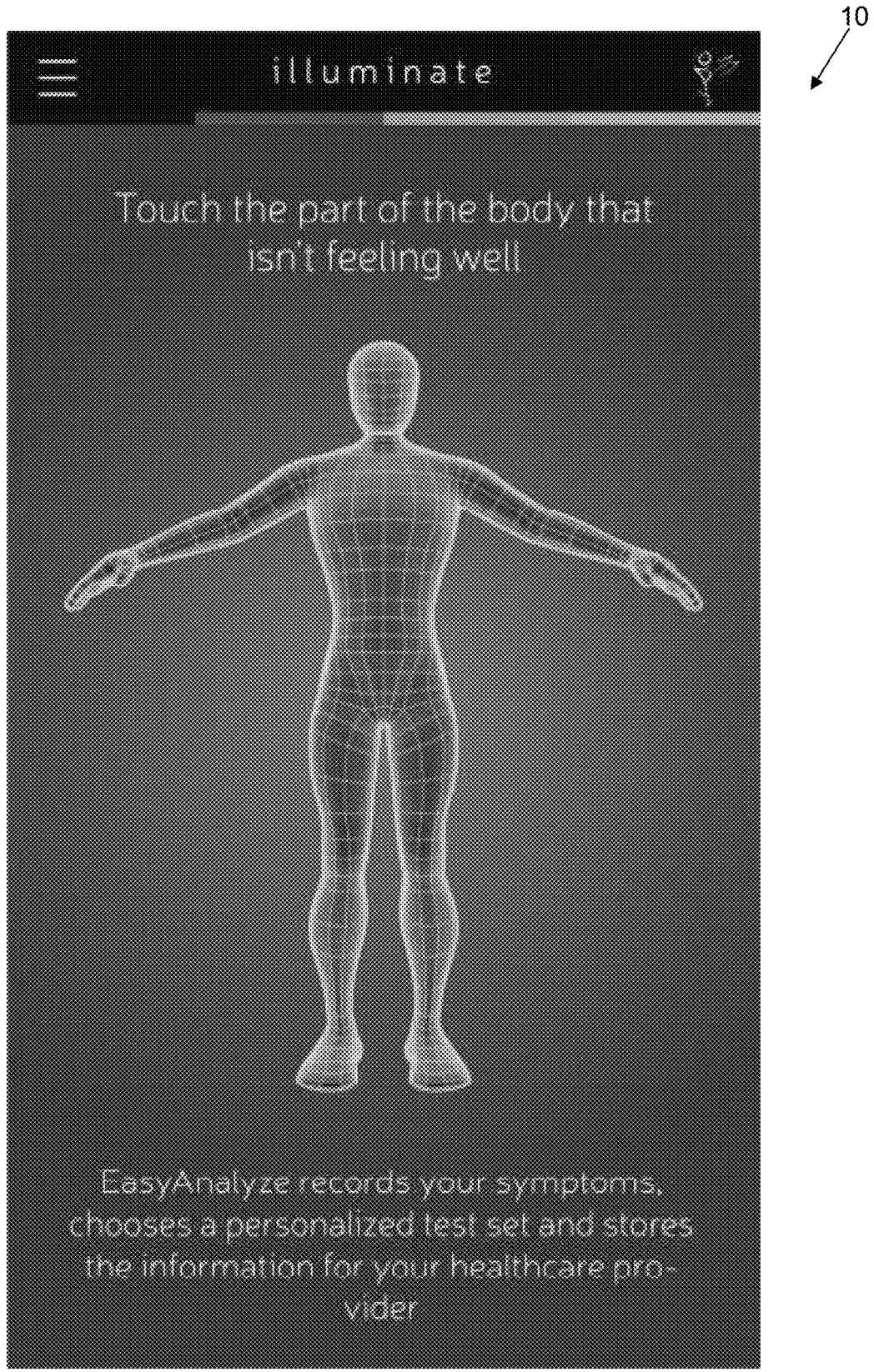
Figure 19:
Figure 20:
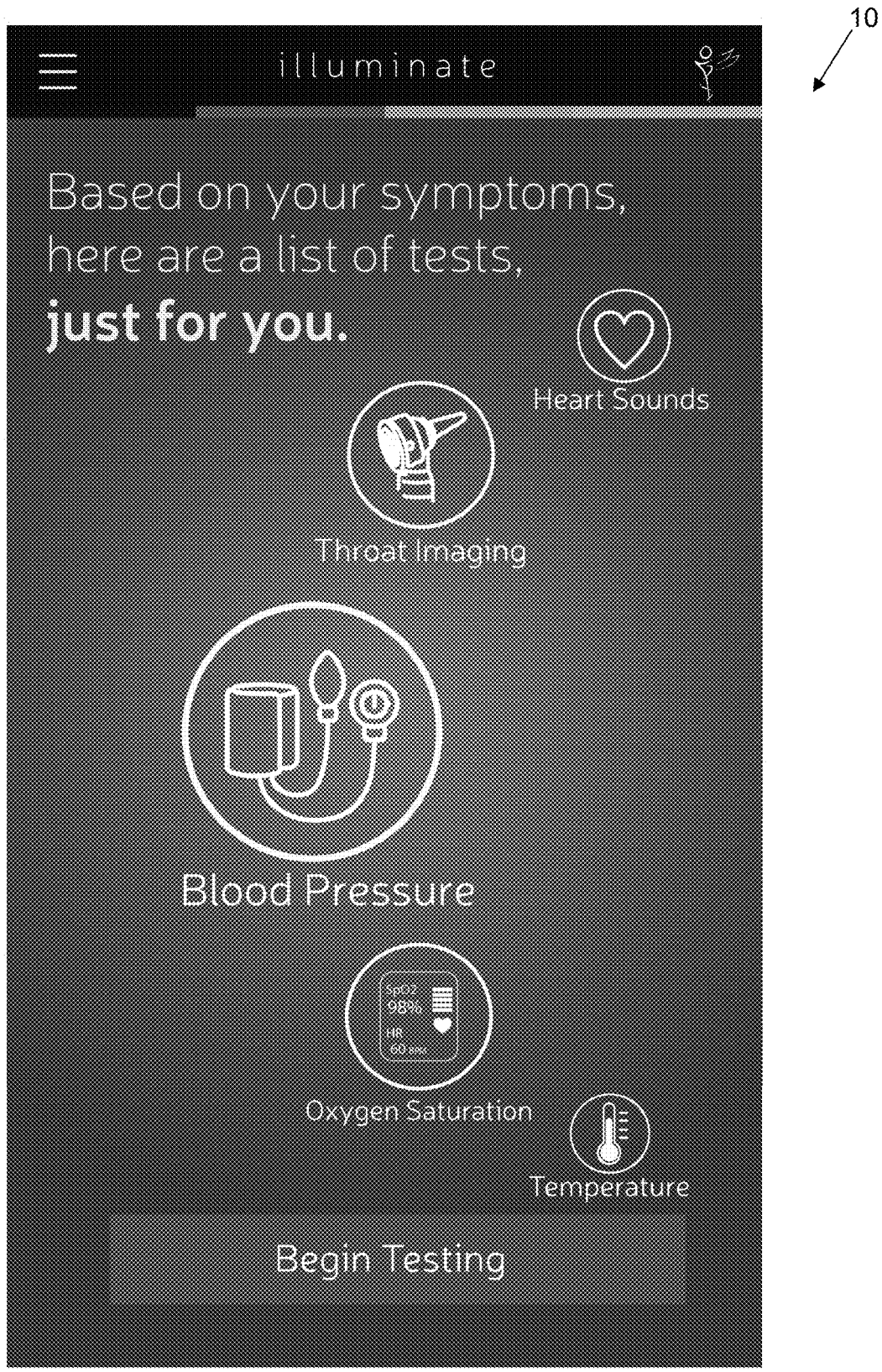
Figure 21:
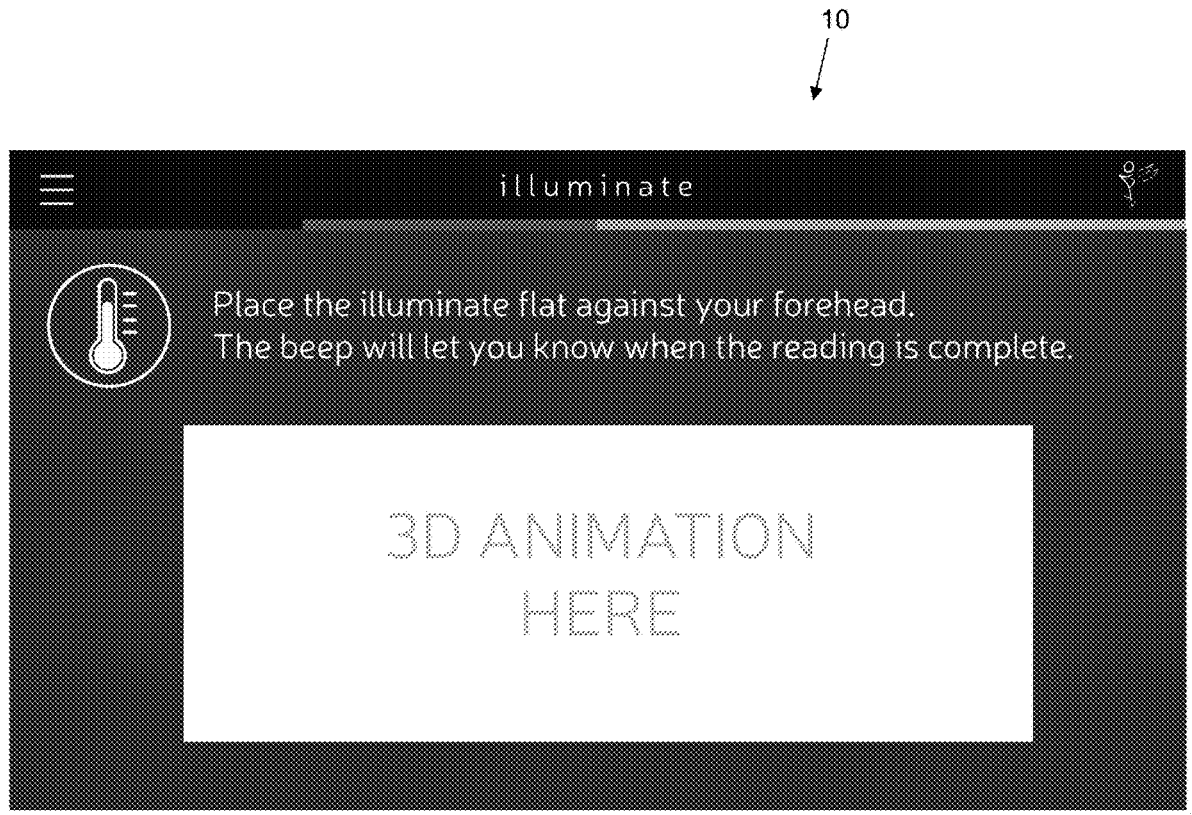
Figure 22:
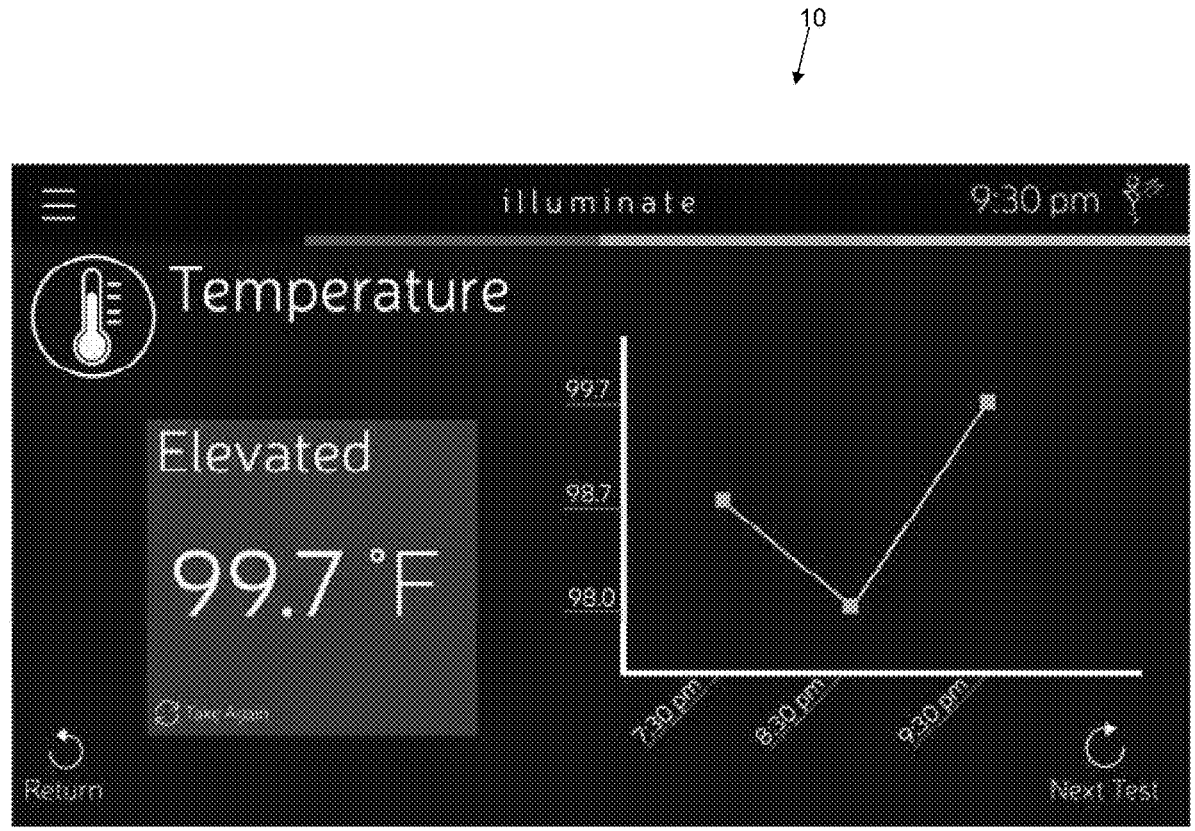
Figure 23:
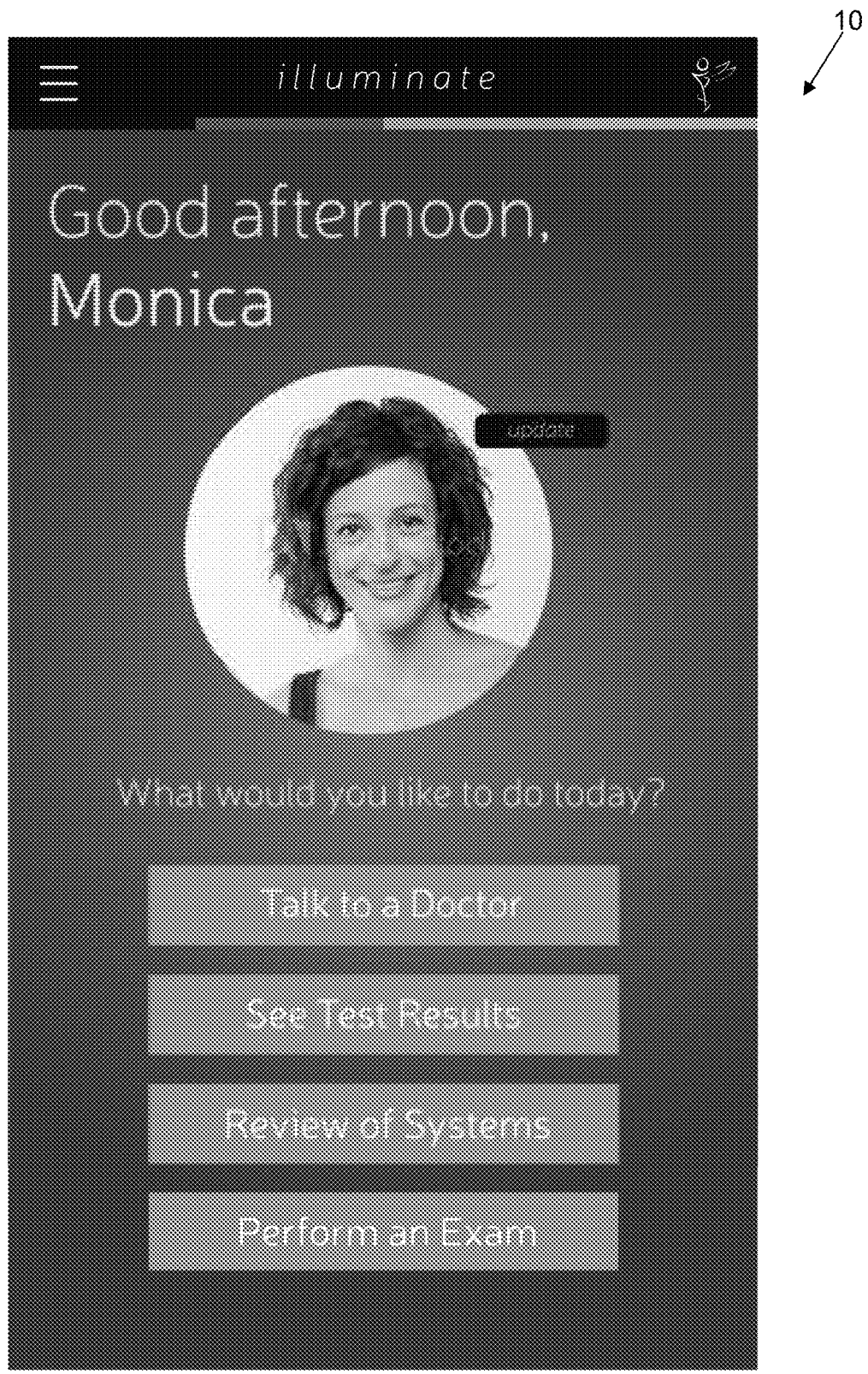
Figure 24:
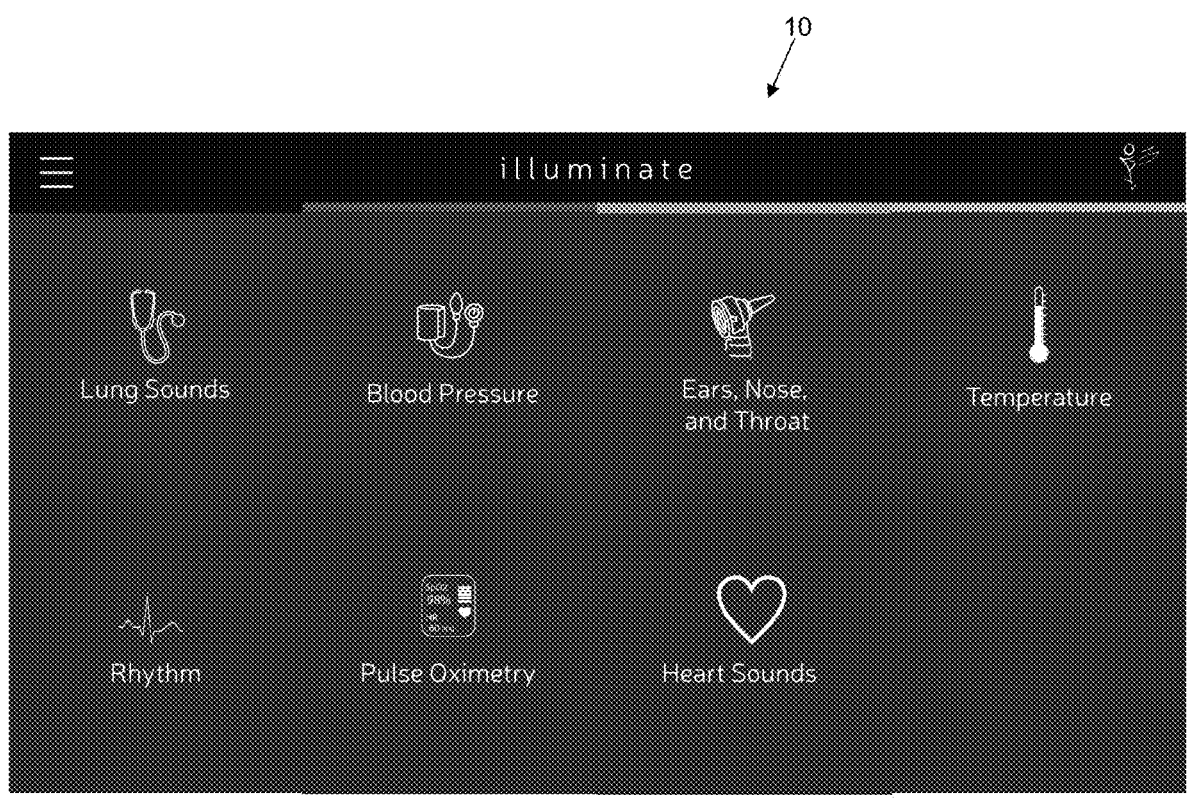
Figure 25:
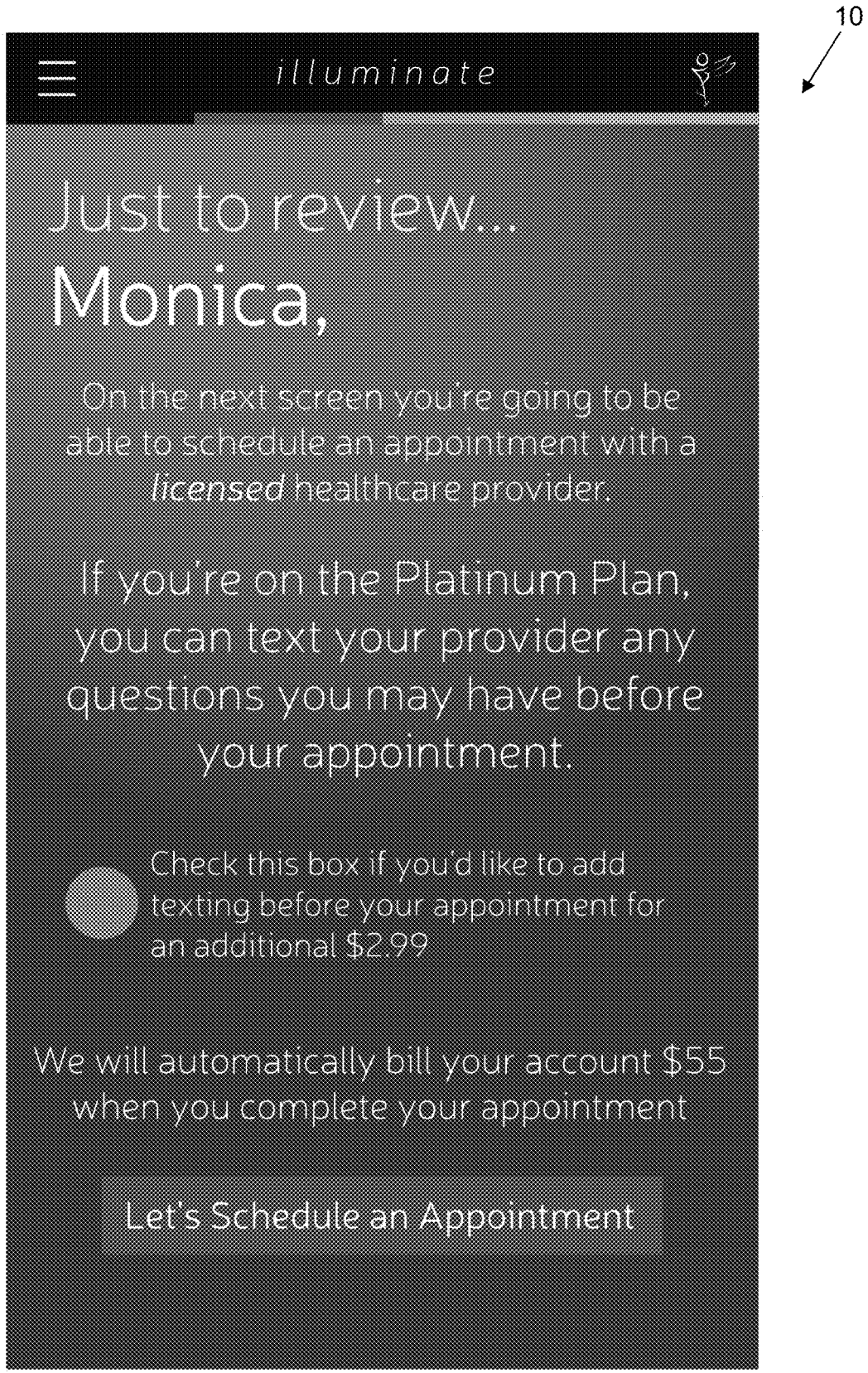

FIG. 16 shows an exemplary workflow for EasyAnalyze™, with FIGS. 17-25 showing enlargements of each of the screen displays in FIG. 16.

6.2.2 Single Test

The single test mode of the Illuminate™ smartphone app 10 is designed for use with chronic care conditions, acute conditions where the patient knows exactly what they want, or the provider is on a call with them and would like them to perform another test that was not assessed by EasyAnalyze™. In this form of the invention, the user selects a single test to be run, and the Illuminate™ smartphone app 10 walks the user through the steps for the test.

6.2.2.1 Single Test Parameters

Exemplary single test parameters are shown in FIG. 26.

6.2.3 Profile

After a patient creates an account with the Illuminate™ device 5 (i.e., using the Illuminate™ smartphone app 10 running on their smartphone 20), they will be prompted to take a profile picture (or use an already existing one) to allow for easy identification.

Figure 27:
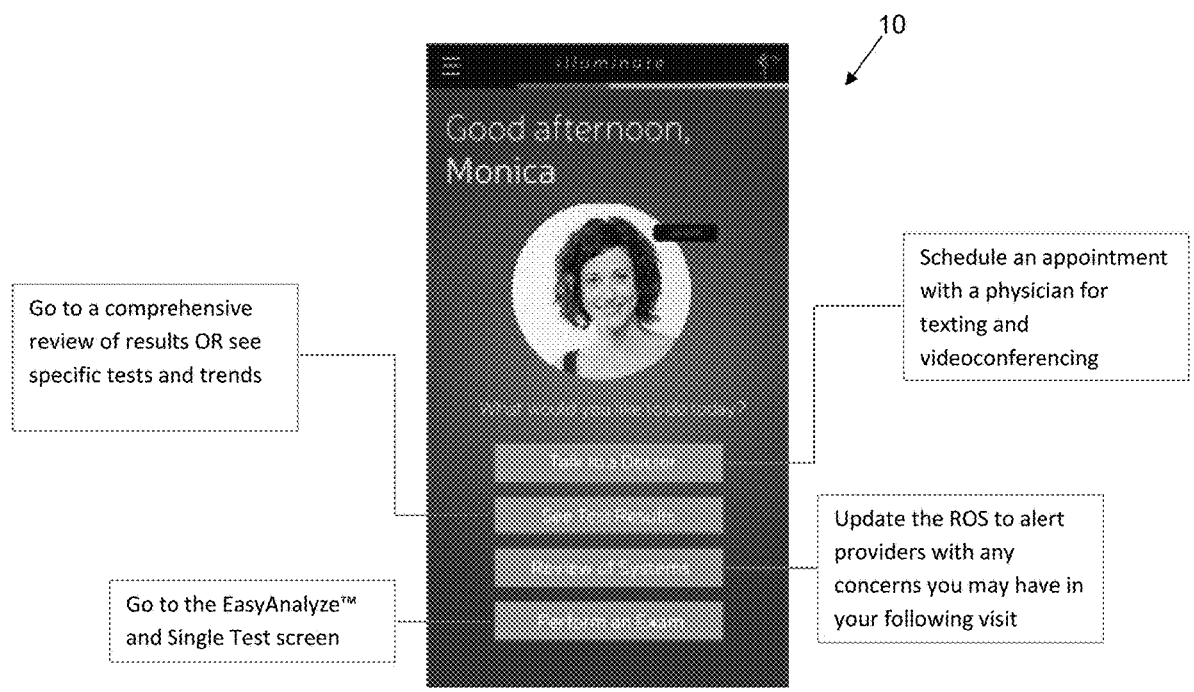
FIG. 27 is a schematic view showing categories of activities which may be undertaken by a user using the Illuminate™ device.

The patient profile preferably comprises four categories of activities which may be undertaken:
(i) talk to a doctor;
(ii) see test results;
(iii) update the Review of System (ROS); and
(iv) perform an exam.
See FIG. 27.

6.2.4 After the Assessment and Before Provider Visit

Figure 28:
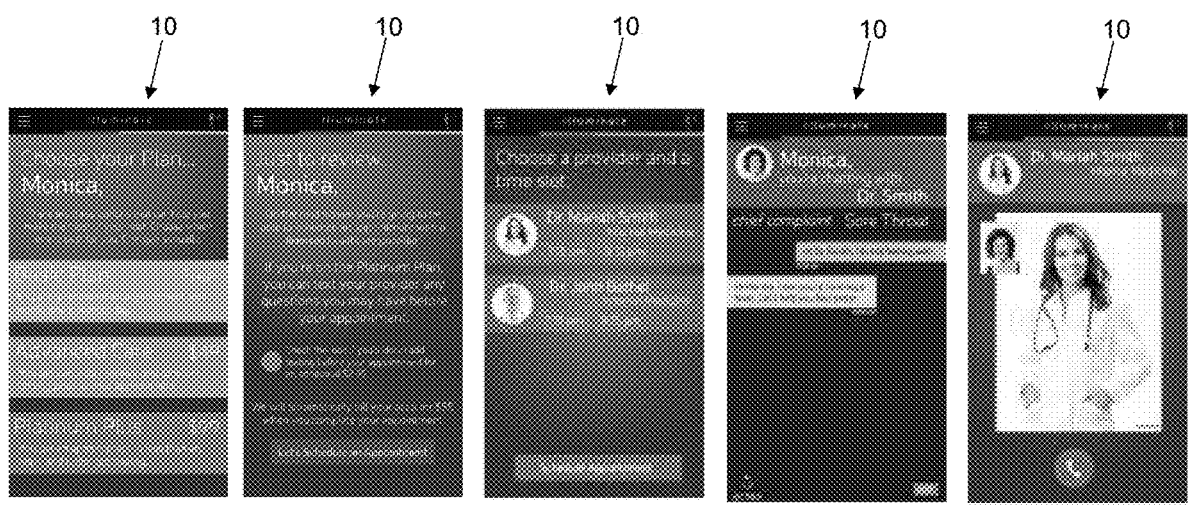
FIG. 28 is a schematic view showing exemplary services which can be obtained using the Illuminate™ device.
Figure 29:
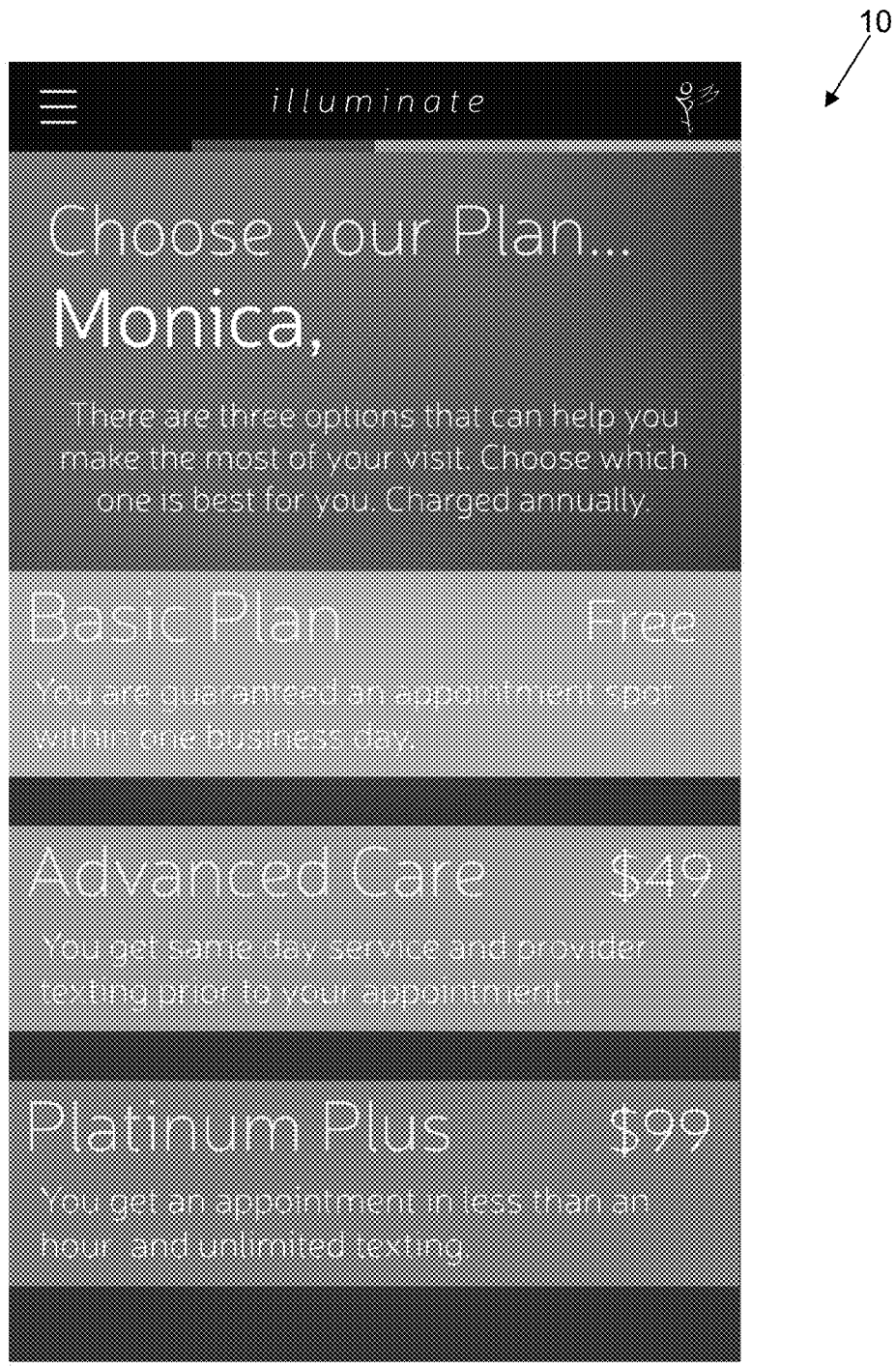
FIGS. 29-33 are schematic views showing enlargements of each of the screen displays in FIG. 28.
Figure 30:
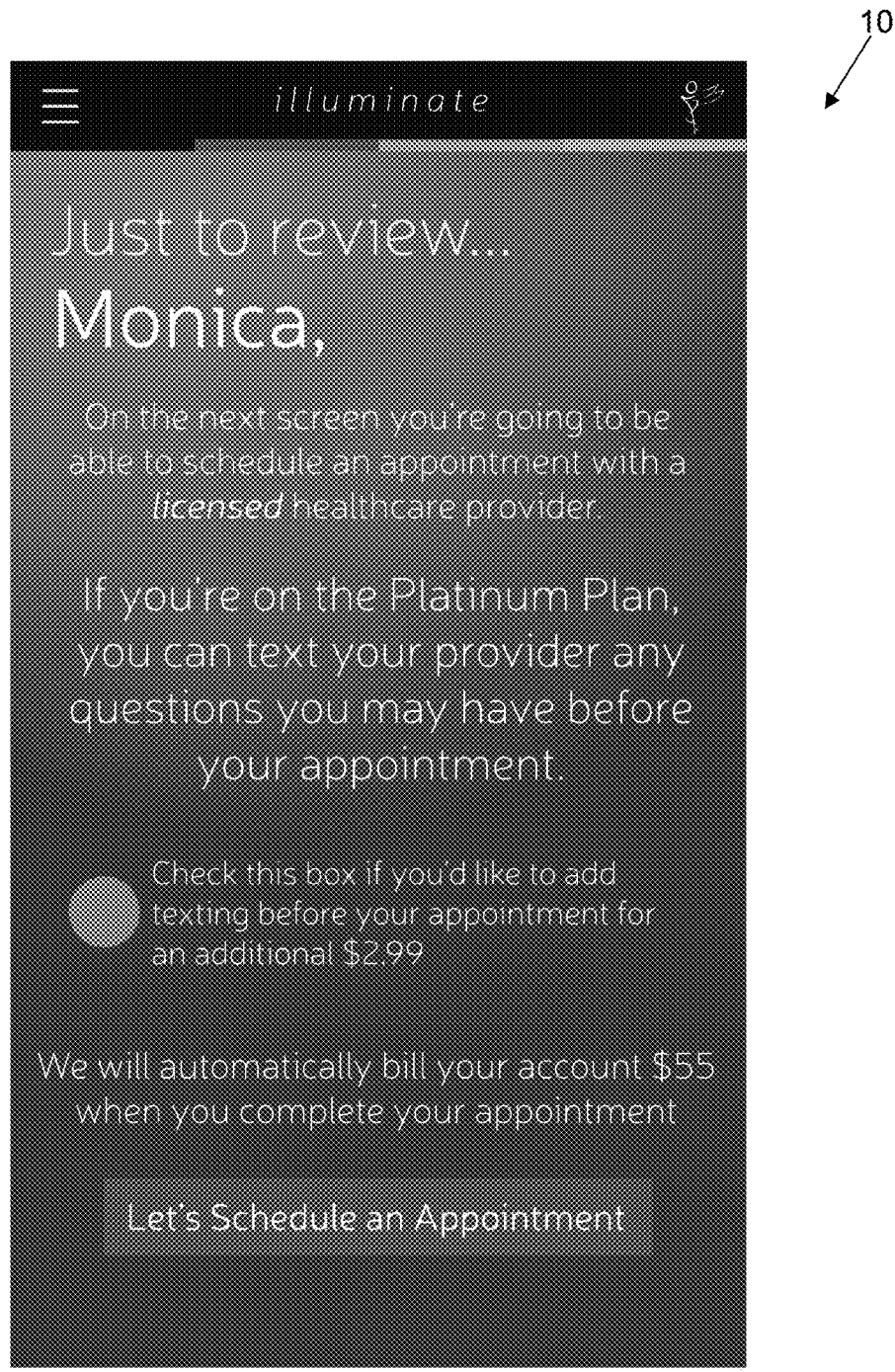
Figure 31:
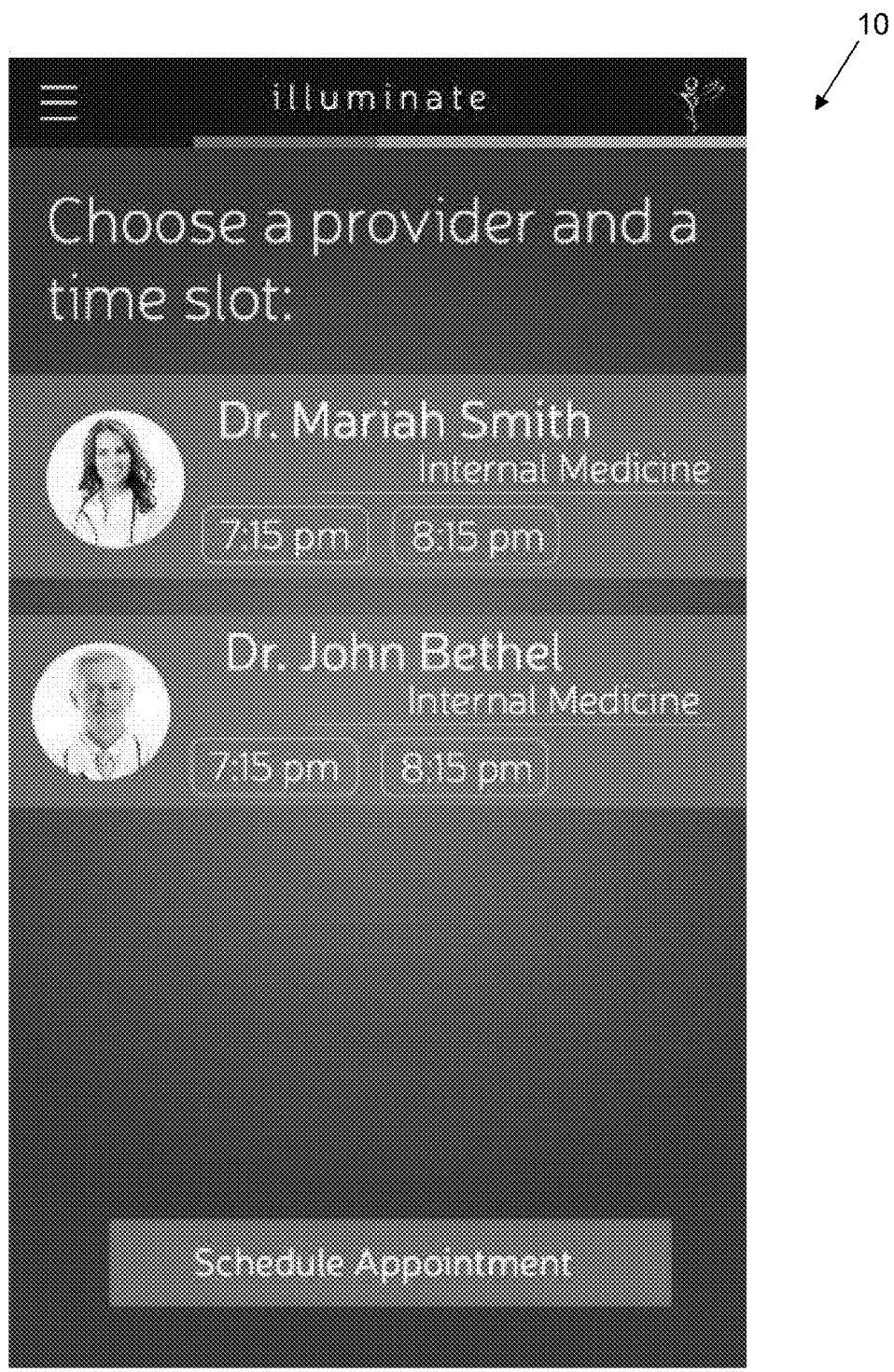
Figure 32:
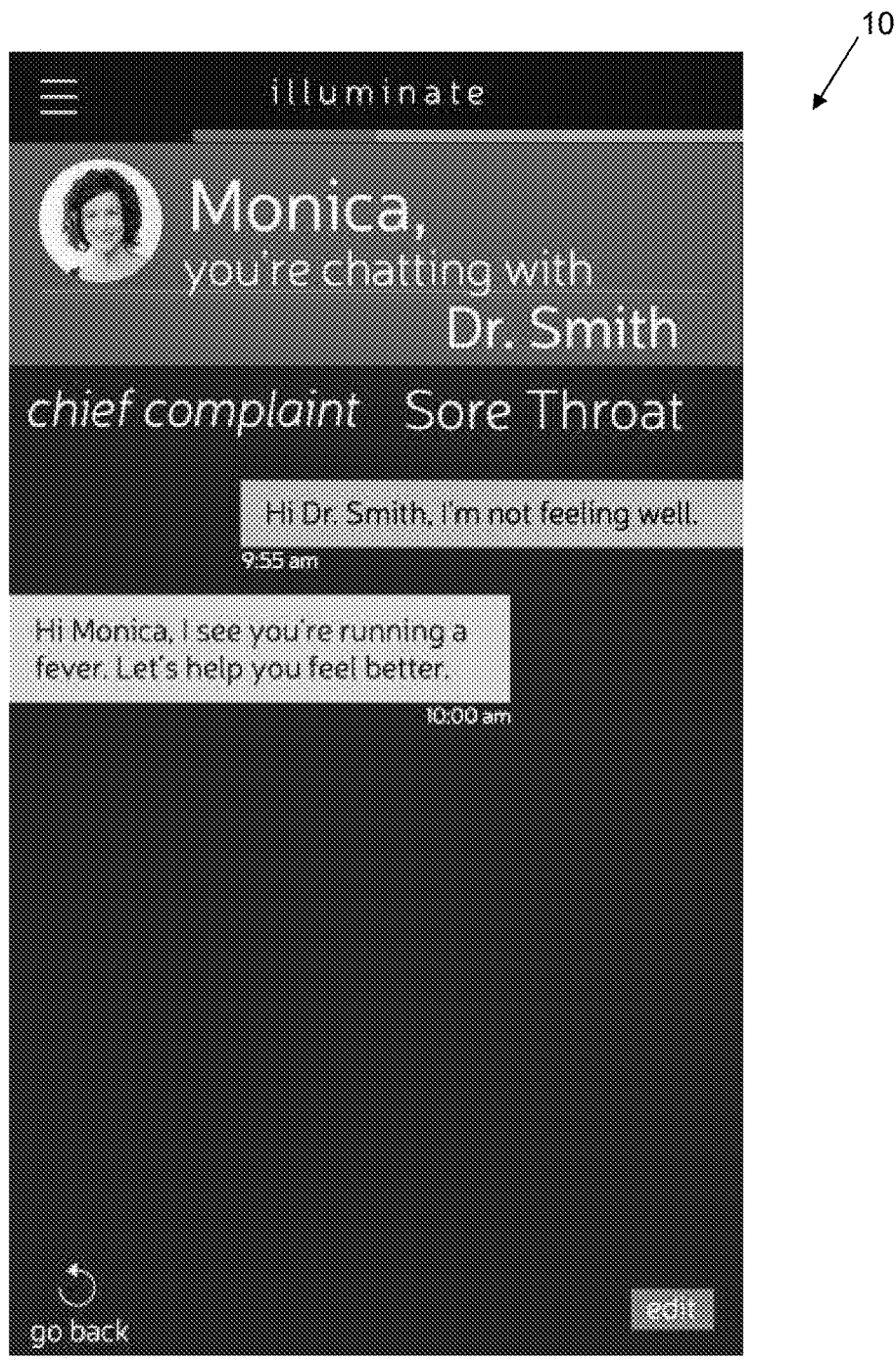
Figure 33:
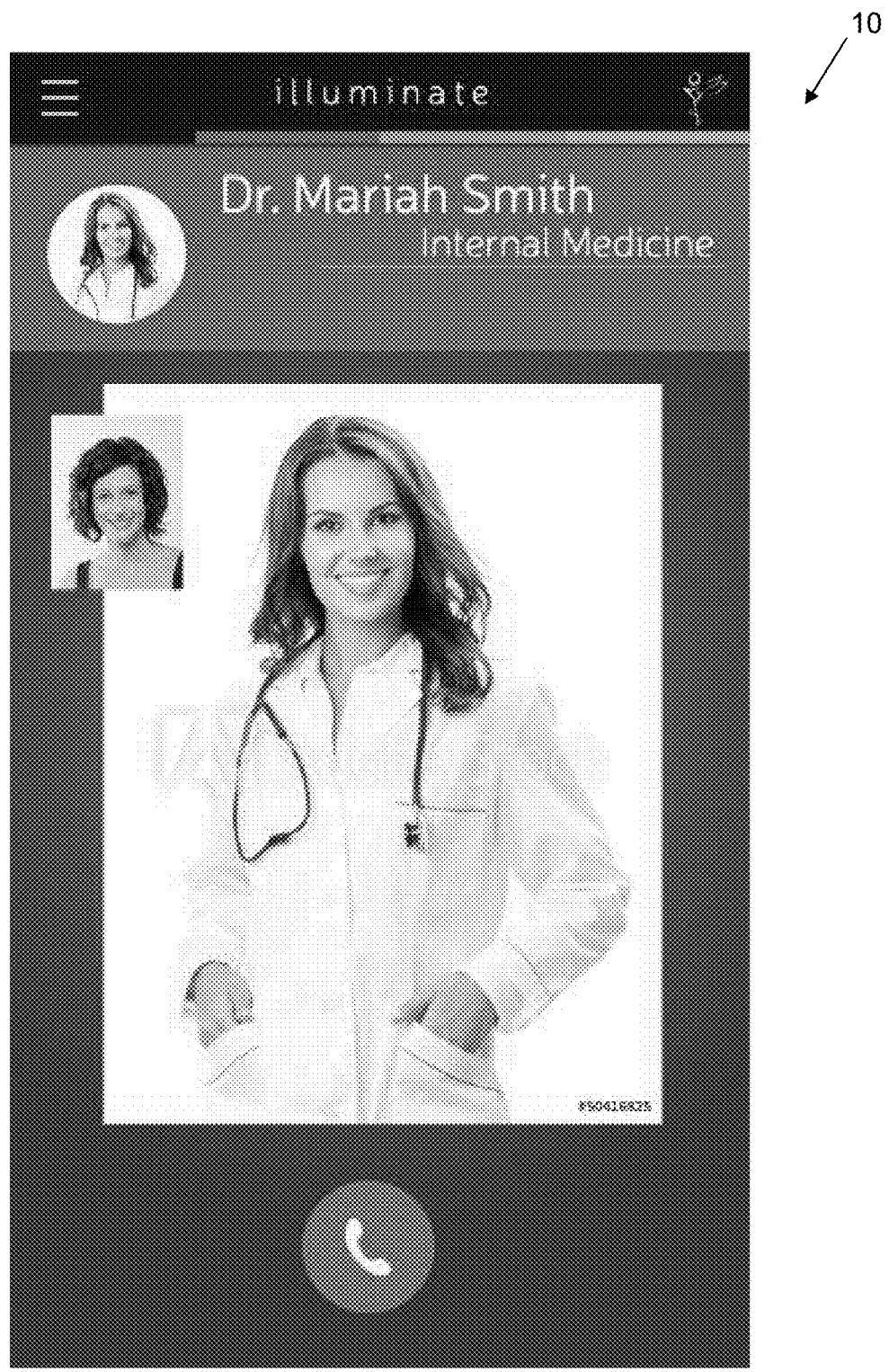

Upon completing their assessment (i.e., running one or more tests and acquiring sensor data, etc.), the patient will likely want to create an appointment (e.g., a teleconference) with a provider. When providers sign up, they have a calendar in which they can set and edit dates and times for their availabilities. This schedule is dynamically updated and allows a patient to see what provider is available at which times to schedule an appointment. See FIG. 28, with FIGS. 29-33 showing enlargements of each of the screen displays in FIG. 28.

Patients are billed at a rate that allows for competitive pricing in the markets at the time of the appointment and are prompted to accept the terms and conditions of the appointment without having to re-enter any payment details. In one preferred form of the invention, there are three tiers of service which a patient can elect to choose:
Basic—allows patients to see a provider within at least 24 hours of scheduling an appointment.
Advanced Care—allows same day service and same day texting after the exam was performed and prior to the appointment.
Platinum Plus—allows for appointments within an hour window and texting before and after performing an exam.

Providers are able to prescribe medication, check lab results, and request updated testing from the patient during and after the exam for follow up. After the appointment (i.e., after the telemedicine call) is completed, the patient is taken back to the main screen, where they have access to their updated record and provider notes.

6.3 Provider Side—Patient Videoconference

6.3.1 Setting a Schedule

Figure 34:
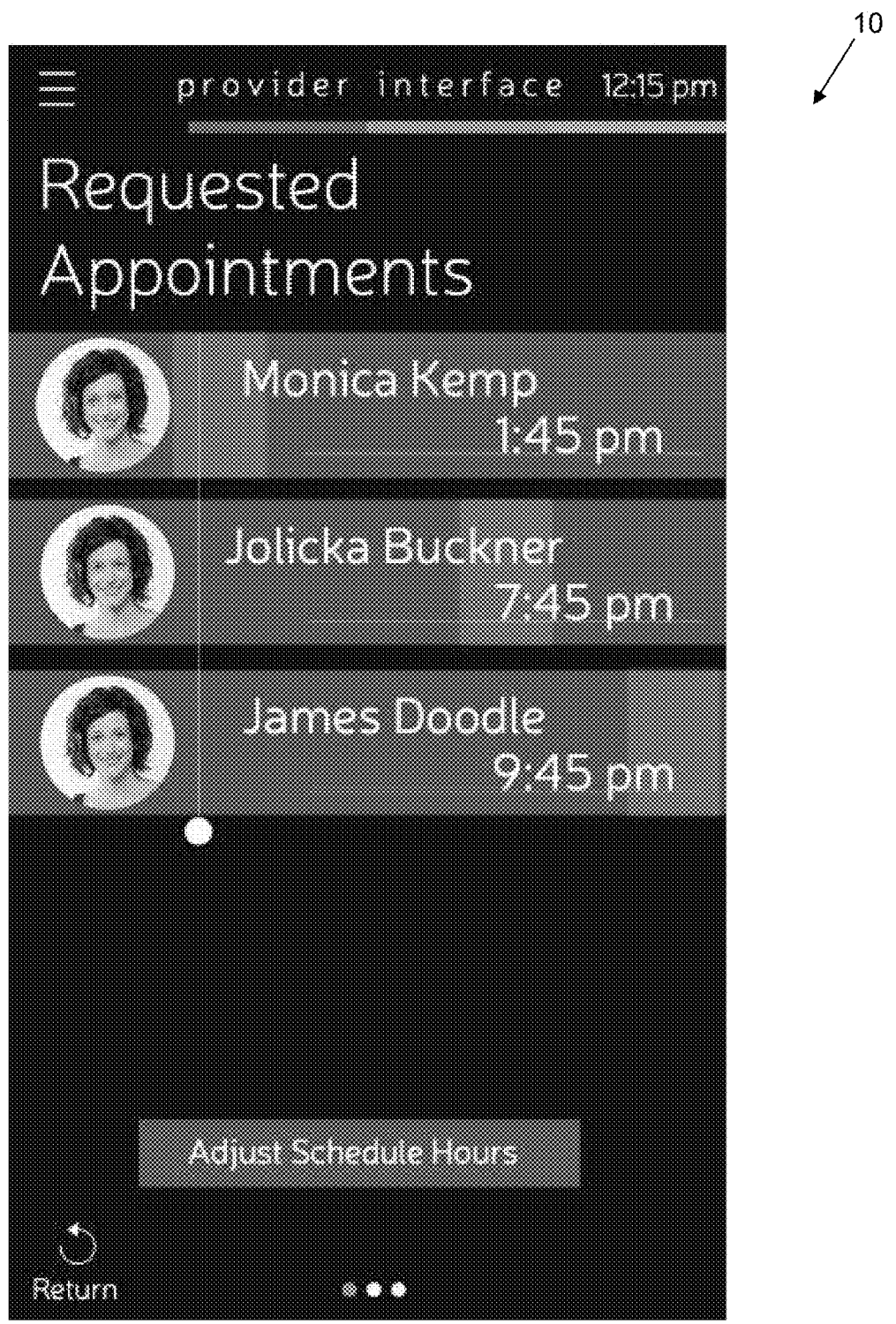
FIG. 34 is a schematic view showing exemplary appointments which may be requested of a healthcare provider using the Illuminate™ device.

Upon registration and approval, physicians are taken to a screen where they are able to see a calendar and set a schedule. Appointments that are requested with that provider automatically fill if there is free time available in the provider schedule. See FIG. 34.

6.3.2 Approaching and Initiating the Appointment

Figure 35:
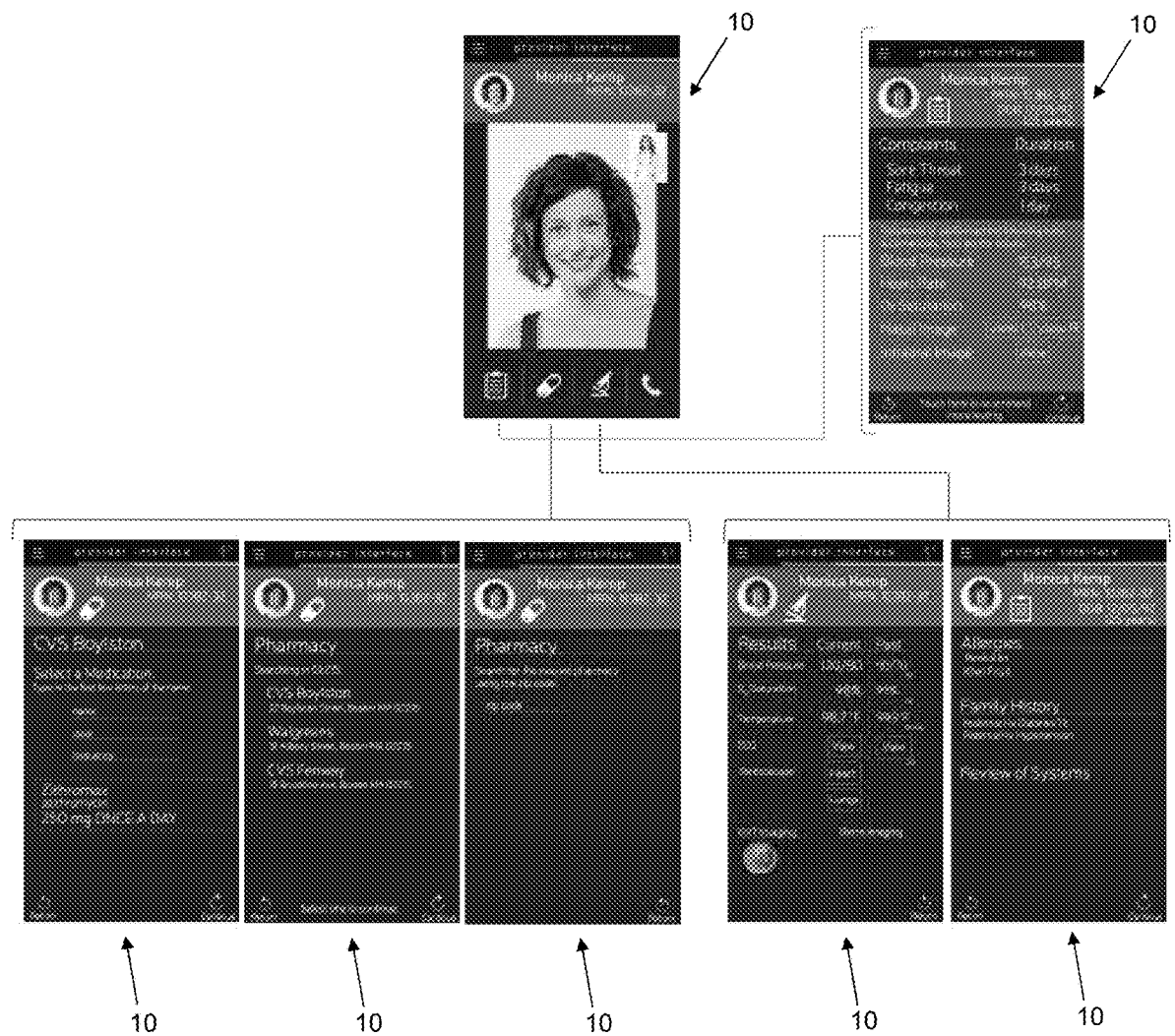
FIG. 35 is a schematic view showing exemplary interactions between a healthcare provider and a patient using the Illuminate™ device.
Figure 36:
FIG. 36-42 are schematic views showing enlargements of each of the screen displays in FIG. 35.
Figure 37:
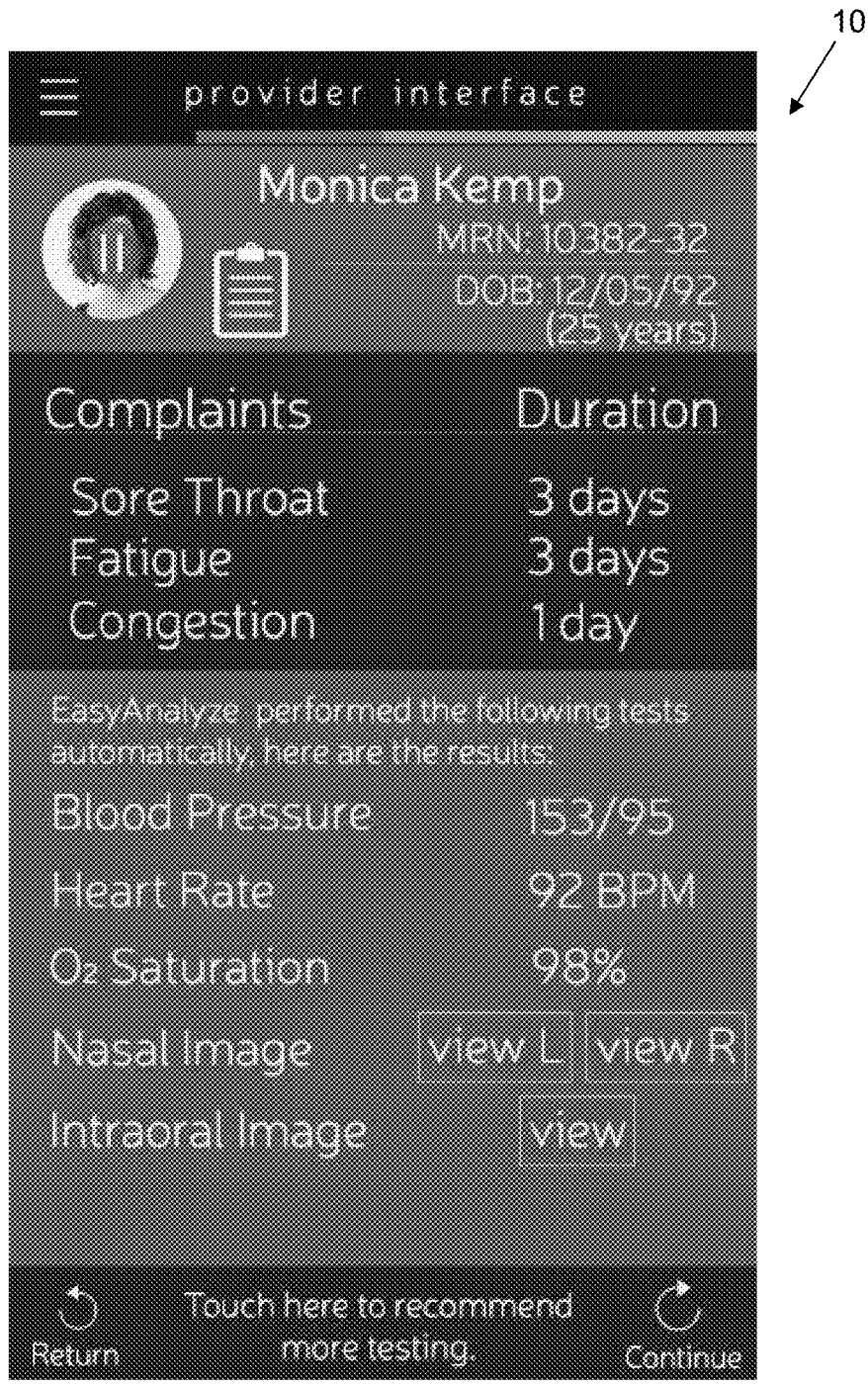
Figure 38:
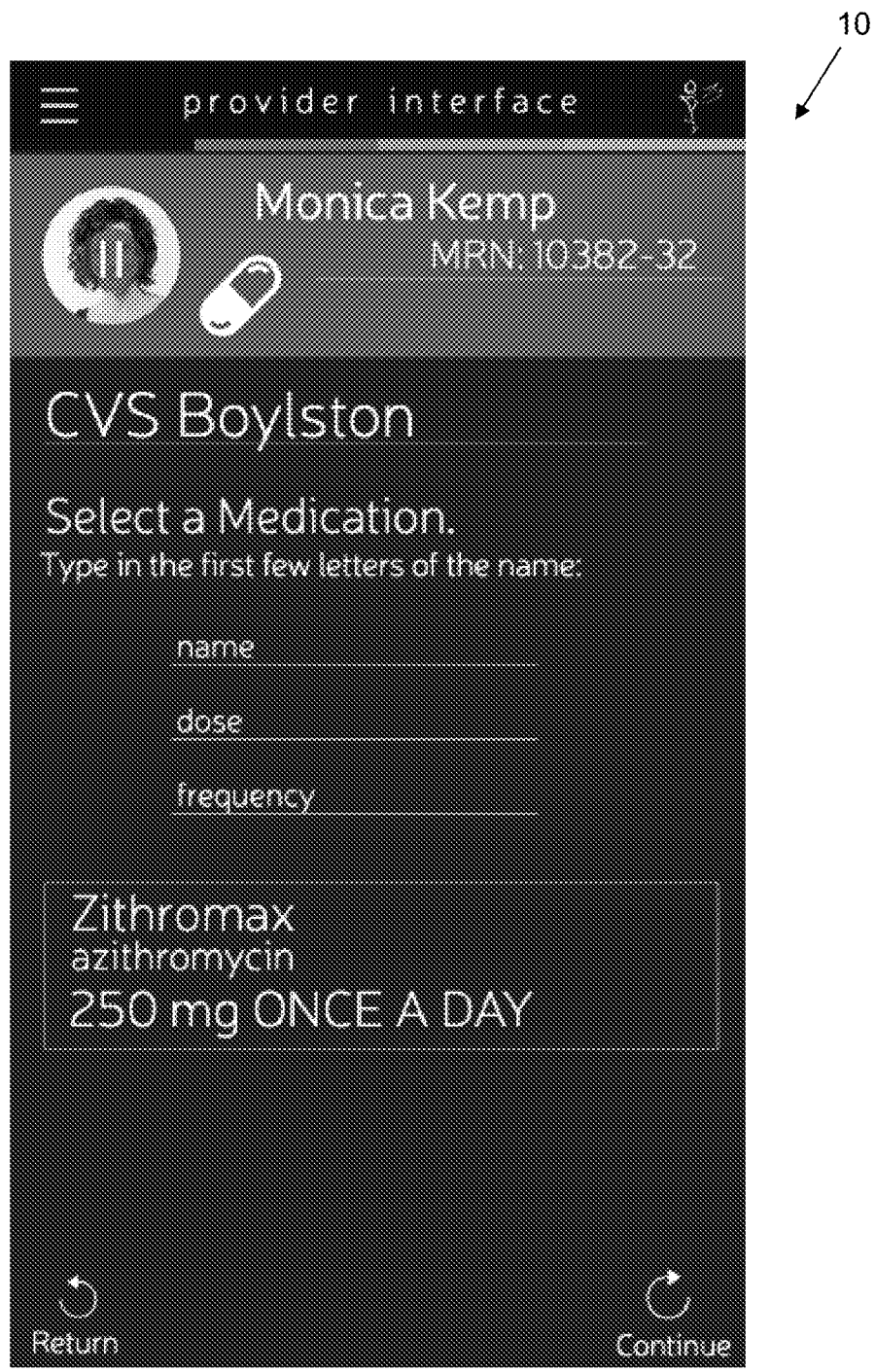
Figure 39:
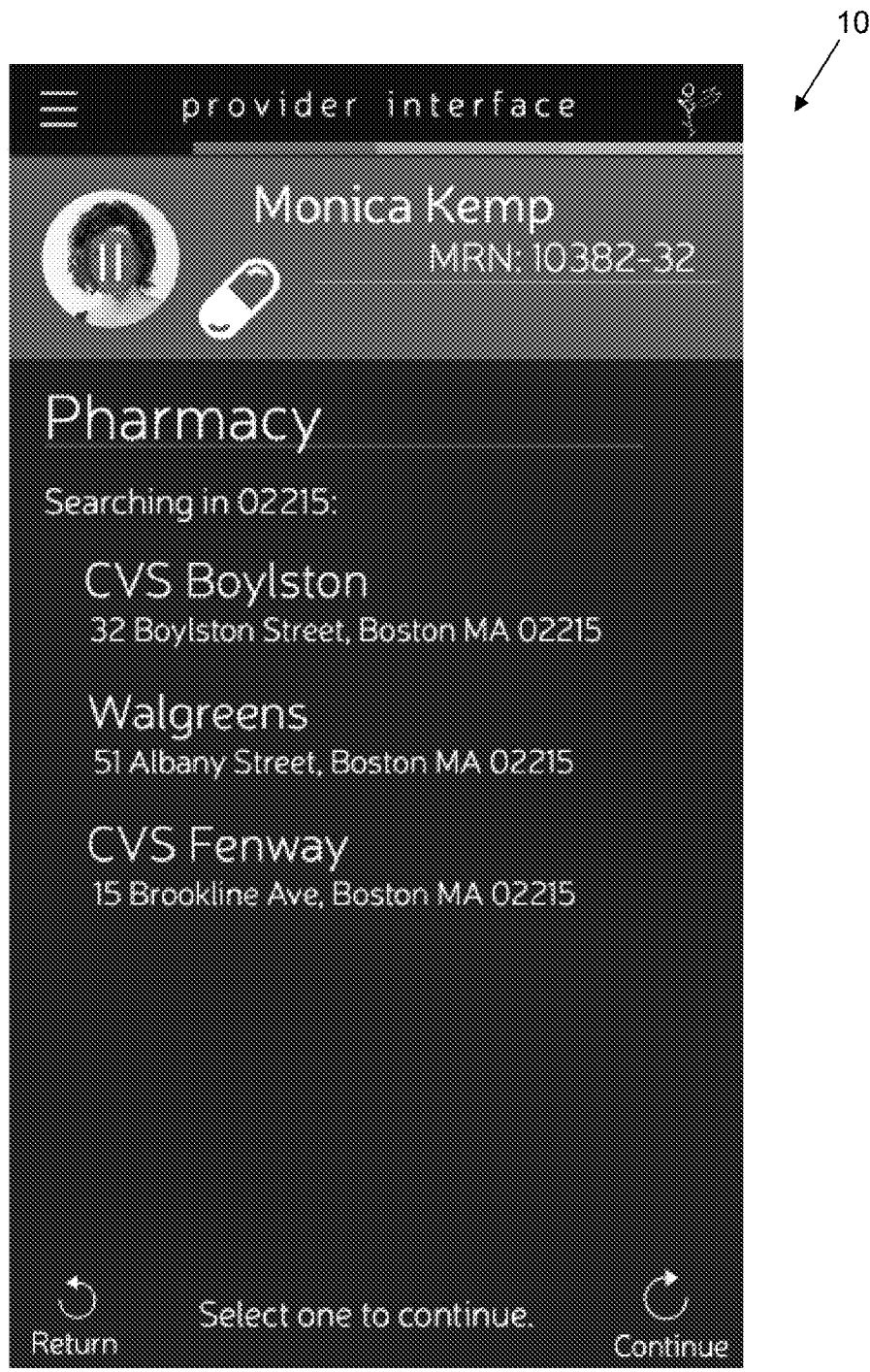
Figure 40:
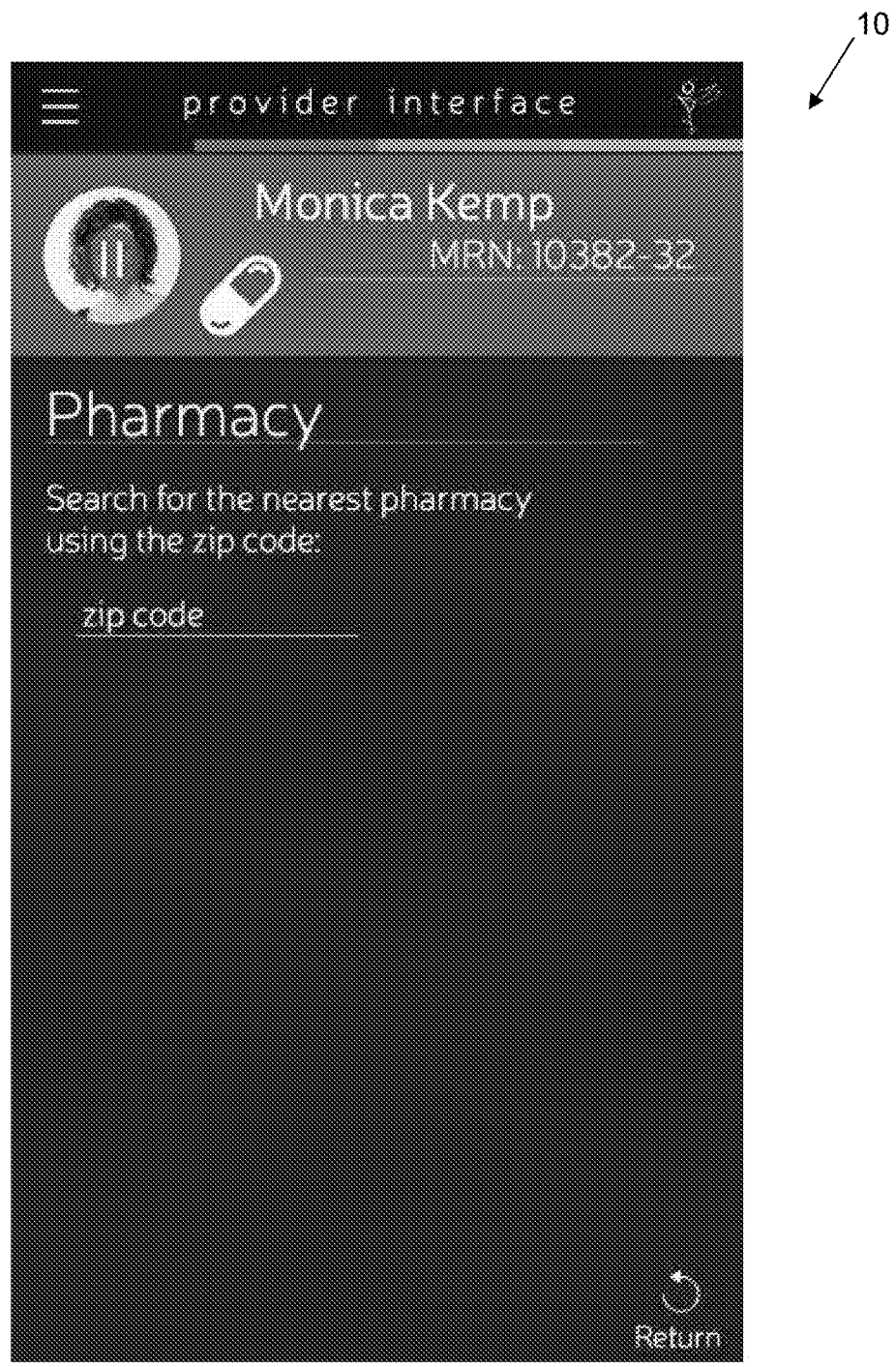
Figure 41:
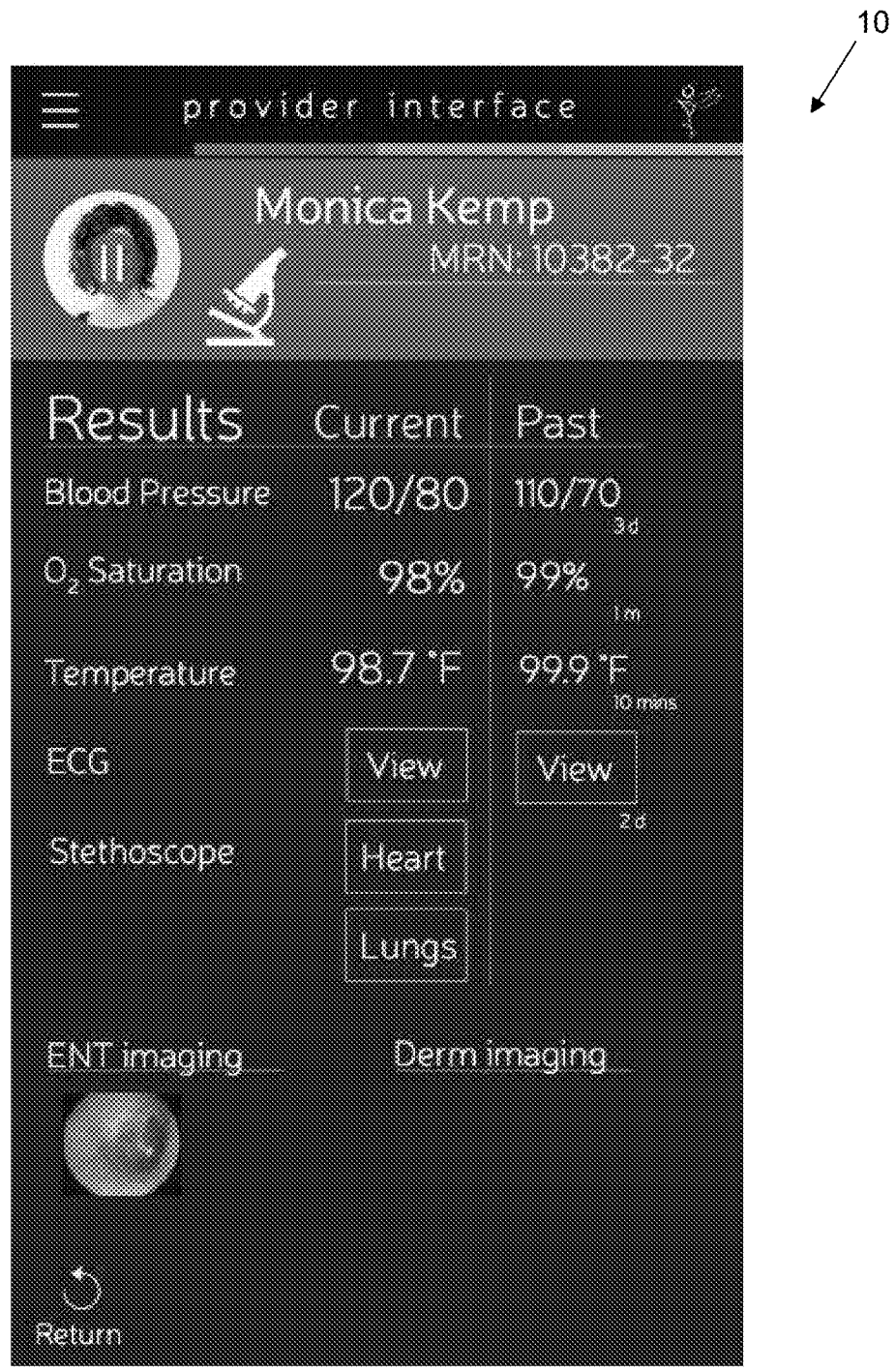
Figure 42:
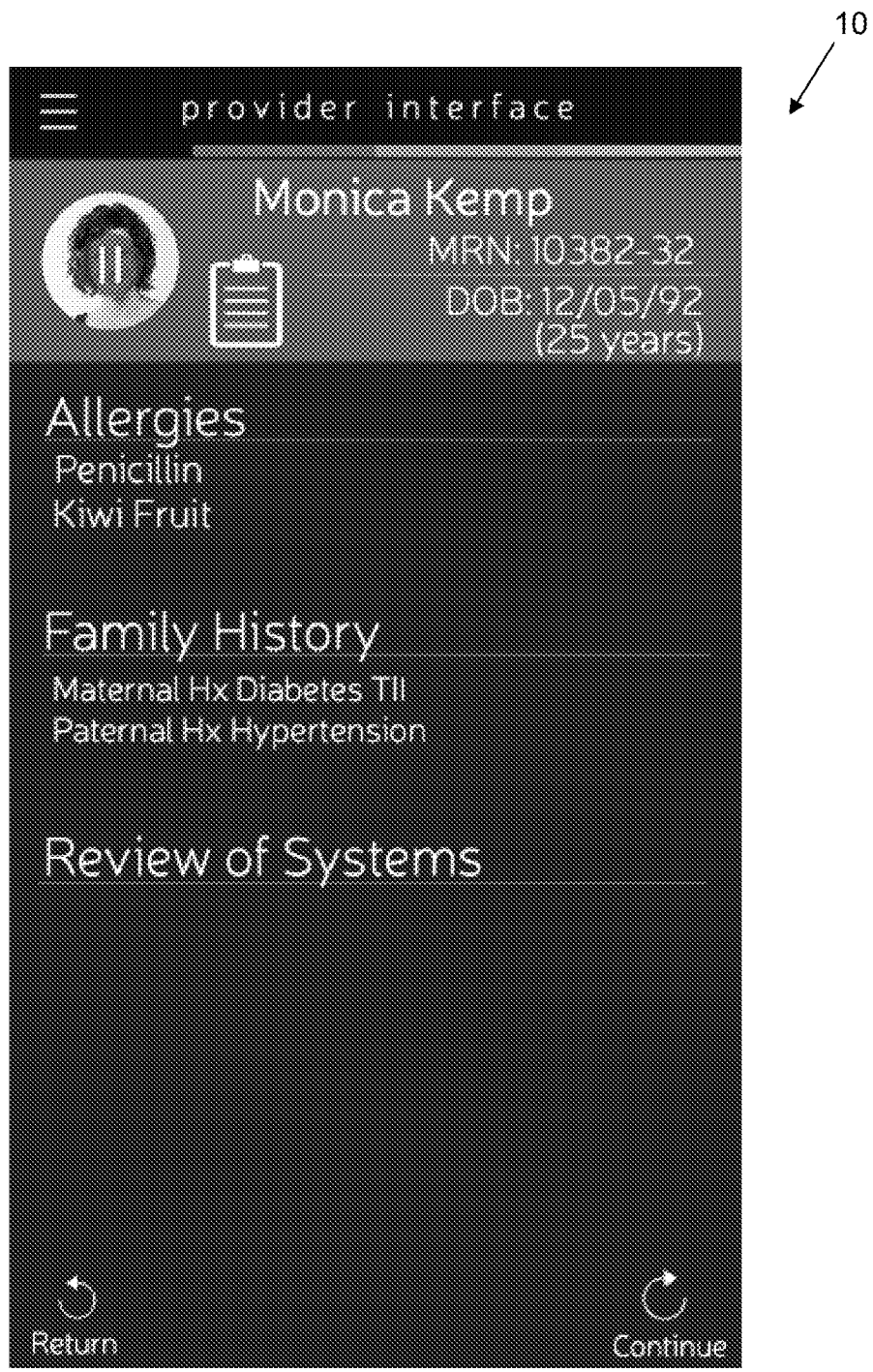

Once an appointment approaches, the provider is able to open a chat dialog with the patient if they wish to do so. Exam results from the Illuminate™ device 5 are sent over as soon as the appointment is scheduled and, if the exam was performed such that too much time has passed for the provider to be comfortable interpreting the results, the provider can request that the patient perform another exam prior to the appointment. Once the call is initiated between the provider and the patient, they have a variety of options, as seen in FIG. 35, with FIGS. 36-42 showing enlargements of each of the screen displays in FIG. 35.

6.4 Provider Side—Performing an Exam

One of the benefits of the Illuminate™ device 5 is that it helps providers stay more efficient. Instead of having duplicate equipment in each room, they can carry the Illuminate™ device 5 in their pocket. Instead of having only written text recorded for documentation purposes, they can visually record medical information instantly as it is gathered, in the form that it is gathered in (e.g., sounds, photographs, etc.). Instead of having to wait for an administrator to enter information into the Review of Systems (ROS) that is often hard to read and photocopied beyond comprehension, it is automatically entered in by the patient (if the patient is operating the Illuminate™ device 5) or by the provider (if the provider is operating the Illuminate™ device 5) and only pertinent information is shown.

Figure 43:
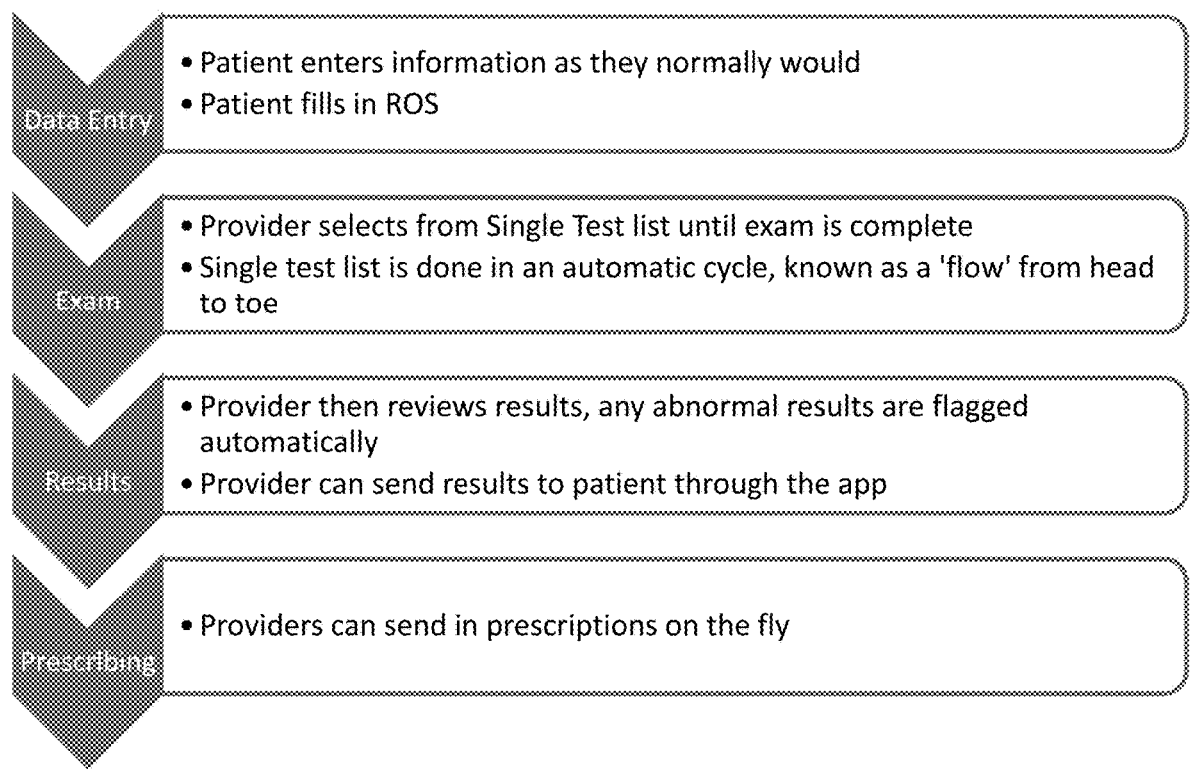
FIG. 43 is a schematic view showing an exemplary treatment process associated with the Illuminate™ device.

FIG. 43 is a schematic view showing an exemplary treatment process using the Illuminate™ device 5.

6.5 Of Note™

The Of Note™ feature of the Illuminate™ smartphone app 10 automatically flags any worrisome symptoms identified on the Review of Systems (ROS) done at patient intake (i.e., at the time of acquiring information from the patient). This saves the time of physicians reading through a traditional list of patient data (frequently not organized in any particular fashion) and also reduces the risk of the physician overlooking important signs and symptoms.

7. Appendix A

7.1 Acute Conditions Assessable by the Illuminate™ Device 5

FIG. 44 is a table showing exemplary acute conditions assessable by the Illuminate™ device 5.

7.2 Chronic Conditions Assessable by the Illuminate™ Device 5

FIG. 45 is a table showing exemplary chronic conditions assessable by the Illuminate™ device 5.

8. Appendix B

8.1 Review of Systems (ROS)

The Illuminate™ device 5 provides a solution to the problem of traditional telemedical consultations where the focus is on an immediate and acute condition and where the data acquired relates solely to that immediate and acute condition. While the Illuminate™ device 5 can be used in this manner, it offers much more: it can be used to provide a complete medical experience in the home, essentially mimicking an in-office visit, acquiring information on a range of anatomical systems (including anatomical systems unrelated to an immediate or acute condition) via sensor-acquired data as well as patient-answered questionnaires. Significantly, the Illuminate™ device 5 can be used for monitoring chronic health conditions (examples of such are patients with diabetes, who are able to record images of wounds, measure blood pressure, and upload blood sugar values, as well as patients with atrial fibrillation, who can record an ECG regularly and combine that data with their input patient information and the ROS to provide better management of their condition than recording their ECG alone).

Obtaining a thorough history of a patient is essential in the maintenance of good health. The feature by which the illuminate does this is known as the Dynamic Review of Systems.

A Review of Systems (ROS) is not essential for the assessment of a patient in every case but is extremely useful to assess changes in a patient's health over a given time frame. The full and complete Review of Systems (ROS) performed is intended to be an initial event, with periodic updates requested to be completed by the patient in order to identify earlier-on whether any disease processes may be starting. As time goes on, the Review of Systems (ROS) is dynamically updated with provider diagnoses and with patient symptom reporting. This dynamic updating is designed to alert the provider if at any time there appears to be a degrading of the patient's health.

To make it easier for patients to identify the pertinent symptoms that they have been experiencing, the Review of Systems (ROS) is mapped to plain English, with the corresponding medical term being presented to providers in the "Of Note™" section of the Illuminate™ smartphone app 10. Patients have the ability to opt out of the Review of Systems (ROS) feature if they wish.

8.2. Initial Intake Questionnaire

FIG. 46 illustrates an exemplary initial intake questionnaire, showing both the "plain English" terms shown to a patient and the corresponding medical terms shown to providers.

8.3 Subsequent Visit Intake Update Questionnaire

The Illuminate™ device 5 also provides for subsequent intake update questions, e.g., "You reported you were experiencing X symptom on [DATE], Do you still have X symptom?".

9. Some Significant Aspects of the Illuminate™ Device 5

(i) The Illuminate™ device 5 provides a portable medical device that allows point-of-care testing using an array of diagnostic sensors coupled to a smartphone for rapid assessment.

(ii) The modules 15 of Illuminate™ device 5 use the onboard processor 65 of the smartphone to hand off intensive processing requirements of the sensors —audio files, data transformation and filtering, and machine learning— instead of leaving the modules 15 of the Illuminate™ device 5 to do so, which would limit the capabilities of the device. Devices on the market currently acquire data and send that data to a phone, where it is packaged and sent off to a provider. Any modification to the acquired data, however, happens on the device itself, and not on the phone. In order to handle the complex demands that modern machine learning algorithms use, the devices would require high power processors that would need cooling and drain the battery needlessly. The Illuminate™ device 5, however, takes advantage of the fact that data processing after acquisition is done using the high-power processor 65 of the smartphone 20 to which it is connected. As an example, the iPhone A11 processor performs similarly to Intel desktop processors, though they are optimized for different tasks. This allows for complex data analysis to be done right on the smartphone, in real time. This simplifies the need for providers to spend time analyzing the data itself, as it will already be in a presentable and final format, ready for use by the provider.

(iii) The Illuminate™ device 5 duplicates equipment found in a physician's office, reducing the need to purchase unnecessary equipment and stock each examination room.

(iv) The Illuminate™ device 5 has a surface configuration that is smooth, with each module being in one continuous piece, which is able to be sanitized with simple sanitizing solutions such as hypochlorous acid or quaternary ammonia compounds.

(v) The Illuminate™ device 5 uses, in addition to other features, an algorithm to triage a patient to minimize the workload on the provider and reduce the risk of missing important patient symptoms.

(vi) The smartphone app 10 of Illuminate™ device 5 uses natural language processing to identify key words during a videoconference and to create a word network for the patient and provider. This word network helps identify the chief complaints of a patient and how it evolves over time. Patients and providers often use the same sets of words when describing specific conditions. For example, if a patient has a cold, they will mention things like congestion, fever, and aches. If they have a stomach virus, they might mention how often they go to the bathroom, or how badly they are having abdominal cramps. These words can be picked up by a natural language processor monitoring the teleconference between the patient and provider and, after a specific threshold of the number times the word is said, be placed as a note in their electronic file. This information can be used for a variety of purposes later on, including alerting new physicians of previous complaints, advertising OTC medicines to patients for relief of symptoms they're experiencing, and updating the ROS.

(vii) The natural language processing algorithm of smartphone app 10 of the Illuminate™ device 5 also takes key words from videoconferences between the patient and the provider and interactions from the patient (including texting) to pre-fill fields and update incomplete information in the patient file. This reduces the need for administrative staff to fill out these forms as they normally would be charged with doing in a provider office, increases accuracy, and provides immediate information for the provider to review. There are sections while filling in a patient file that a patient might elect to ignore. This may be because of their perceived urgency in getting to see a provider, or they might not feel the need to fill it in because they don't see the necessity behind it. A natural language processor may be used to enter data into fields of a patient file that have been ignored or entered incorrectly. This passive filling-in of data fields ensures that data is complete and up to date. An example might be that a patient has not filled out their weight, but during a call with a provider, the provider asks for their weight in order to prescribe a drug. Prior to the call, the missing data fields may be flagged for the natural language processor to listen for the keywords which would be appropriate to fill in the missing data field. When the patient mentions their weight, the keyword is activated and the value is then placed into the field where it was initially missing.

(viii) The smartphone app 10 of Illuminate™ device 5 uses a smart algorithm to begin acquiring data regarding reported patient symptoms, acquired sensor data, provider diagnosis, and prescribed medication to learn prescribing habits of providers, conditions which are able to be treated with over-the-counter (OTC) medications, suggestions of the OTC medications to providers and patients, and enhancing the triage algorithm. This algorithm is designed to collect data to "teach" another machine learning algorithm on how information collected, from the start of a patient using the device to the physician consult and prescribed drugs, can be used to guide clinical decisions and, in lieu of a provider, offer patients relief using OTC medications. An example of this might be a patient suffering from a cold who may not want to speak with a provider, as they don't feel their condition is severe enough to warrant it. With enough prerequisite information collected, the device may suggest a decongestant, pain reliever, and fever reducer that is safe and effective considering the patients prior conditions and medications they may be on already.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A system for acquiring physiological data from a patient, the system comprising:
    a smartphone configured for wireless communication;
    an adapter for releasably mounting to the smartphone;
    a sensor module for releasably mounting to the adapter, the sensor module comprising a gyroscope, an accelerometer and at least one physiological sensor for acquiring physiological data from the patient; and
    a software app running on the smartphone for (i) using data acquired from the gyroscope, the accelerometer and the physiological sensor to confirm that the sensor module is in the correct orientation for acquiring physiological data from the patient, (ii) prompting a user to change at least one of the orientation of the sensor module and the orientation of the user when the sensor module is not in the correct orientation, (iii) wirelessly controlling operation of the sensor module and wirelessly receiving the physiological data from the sensor module, and (iv) wirelessly communicating the physiological data acquired from the patient to a remote location.

2. The system according to claim 1 wherein the software app running on the smartphone is configured to process the physiological data acquired by the sensor module and communicate the results of such processing to at least one of (i) a display screen on the smartphone, and (ii) a remote location.

3. The system according to claim 1 wherein the sensor module comprises at least one of an IR thermometer, a single lead ECG, a stethoscope, a pulse oximeter unit and an ultrasound unit.

4. The system according to claim 1 further comprising a wireless blood pressure cuff for wirelessly communicating with the smartphone.

5. The system according to claim 1 wherein the sensor module comprises an ultrasound unit and a pressure transducer unit configured to measure the pressure applied by the ultrasound unit against tissue.

6. The system according to claim 1 wherein the adapter comprises an adapter body, the sensor module comprises a sensor body, and the sensor module is releasably mounted to the adapter body by at least one of mechanical connector pins and magnets.

7. A system for acquiring physiological data from a patient, the system comprising:
    an adapter for releasably mounting to a smartphone;
    a sensor module for releasably mounting to the adapter, the sensor module comprising a gyroscope, an accelerometer and at least one physiological sensor for acquiring physiological data from the patient; and
    a software app running on a smartphone for (i) using data acquired from the gyroscope, the accelerometer and the physiological sensor to confirm that the sensor module is in the correct orientation for acquiring physiological data from the patient, (ii) prompting a user to change at least one of the orientation of the sensor module and the orientation of the user when the sensor module is not in the correct orientation, (iii) wirelessly controlling operation of the sensor module and wirelessly receiving the physiological data from the sensor module, and (iv) wirelessly communicating the physiological data acquired from the patient to a remote location.

8. A method for acquiring physiological data from a patient, the method comprising:
    providing a system comprising:
        an adapter for releasably mounting to a smartphone;
        a sensor module for releasably mounting to the adapter, the sensor module comprising a gyroscope, an accelerometer and at least one physiological sensor for acquiring physiological data from the patient; and
        a software app running on the smartphone for (i) using data acquired from the gyroscope, the accelerometer and the physiological sensor to confirm that the sensor module is in the correct orientation for acquiring physiological data from the patient, (ii) prompting a user to change at least one of the orientation of the sensor module and the orientation of the user when the sensor module is not in the correct orientation, (iii) wirelessly controlling operation of the sensor module and wirelessly receiving the physiological data from the sensor module, and (iv) wirelessly communicating the physiological data acquired from the patient to a remote location;
    using the software app to control operation of the sensor module so as to acquire physiological data from the patient and transfer the physiological data from the sensor module to the smartphone.

9. The method according to claim 8 wherein the software app running on the smartphone is configured to process the physiological data acquired by the sensor module and communicate the results of such processing to at least one of (i) a display screen on the smartphone, and (ii) a remote location.

10. The method according to claim 8 wherein the sensor module comprises at least one of an IR thermometer, a single lead ECG, a stethoscope, a pulse oximeter unit and an ultrasound unit.

11. The method according to claim 8 wherein the system further comprises a wireless blood pressure cuff for wirelessly communicating with the smartphone.

12. The method according to claim 8 wherein the sensor module comprises an ultrasound unit and a pressure transducer unit configured to measure the pressure applied by the ultrasound unit against tissue.

13. The method according to claim 8 wherein the adapter comprises an adapter body, the sensor module comprises a sensor body, and the sensor module is releasably mounted to the adapter body by at least one of mechanical connector pins and magnets.

* * * * *